United States Patent
Schwartz et al.

(10) Patent No.: US 9,823,250 B2
(45) Date of Patent: Nov. 21, 2017

(54) CRYSTAL STRUCTURES OF HUMAN TORSIN-A AND METHODS OF DETERMINING AND USING THE SAME

(71) Applicant: Massachusetts Institute of Technology, Cambridge, MA (US)

(72) Inventors: Thomas U. Schwartz, Brookline, MA (US); F. Esra Demircioglu, Boston, MA (US); Brian A. Sosa-Alvarado, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/442,639

(22) Filed: Feb. 25, 2017

(65) Prior Publication Data

US 2017/0248601 A1    Aug. 31, 2017

Related U.S. Application Data

(60) Provisional application No. 62/330,683, filed on May 2, 2016, provisional application No. 62/299,699, filed on Feb. 25, 2016.

(51) Int. Cl.
| | | |
|---|---|---|
| *G01N 33/573* | (2006.01) | |
| *C12N 9/14* | (2006.01) | |
| *G01N 23/20* | (2006.01) | |
| *G06F 19/16* | (2011.01) | |
| *G06F 19/18* | (2011.01) | |
| *C40B 30/02* | (2006.01) | |

(52) U.S. Cl.
CPC ............ *G01N 33/573* (2013.01); *C12N 9/14* (2013.01); *C12Y 306/04* (2013.01); *C40B 30/02* (2013.01); *G01N 23/20* (2013.01); *G06F 19/16* (2013.01); *G06F 19/18* (2013.01); *G01N 2333/914* (2013.01); *G01N 2500/04* (2013.01)

(58) Field of Classification Search
None
See application file for complete search history.

(56) References Cited

PUBLICATIONS

Adams, P. D. et al. Phenix: a comprehensive Python-based system for macromolecular structure solution. Acta Crystallogr. D Biol. Crystallogr. 66, 213-221 (2010).
Altschul, S. F. et al. Gapped BLAST and PSI-BLAST: a new generation of protein database search programs. Nucleic Acids Res. 25, 3389-3402 (1997).
Andersen, K. R., Leksa, N. C. & Schwartz, T. U. Optimized *E. coli* expression strain LOBSTR eliminates common contaminants from His-tag purification. Proteins 81, 1857-1861 (2013).
Breakefield, X. O. et al. The pathophysiological basis of dystonias. Nat. Rev. Neurosci. 9, 222-234 (2008).
Brown, R. S. H., Zhao, C., Chase, A. R., Wang, J. & Schlieker, C. The mechanism of TorsinATPase activation. Proc. Natl. Acad. Sci. U.S.A. 111, E4822-31 (2014).
Calakos, N. et al. Functional evidence implicating a novel TOR1A mutation in idiopathic, late-onset focal dystonia. J. Med. Genet. 47, 646-650 (2010).
Chen, V. B. et al. MolProbity: all-atom structure validation for macromolecular crystallography. Acta Crystallogr. D Biol. Crystallogr. 66, 12-21 (2010).
Cheng, F.-B. et al. Combined occurrence of a novel TOR1A and a THAP1 mutation in primary dystonia. Mov. Disord. 29, 1079-1083 (2014).
Crooks, G. E., Hon, G., Chandonia, J.-M. & Brenner, S. E. WebLogo: a sequence logo generator. Genome Res. 14, 1188-1190 (2004).
Dobričić, V. et al. Phenotype of non-c.907_909delGAG mutations in TOR1A: DYT1 dystonia revisited. Parkinsonism Relat. Disord. 21, 1256-1259 (2015).
Dorboz, I. et al. Severe dystonia, cerebellar atrophy, and cardiomyopathy likely caused by a missense mutation in TOR1AIP1. Orphanet J Rare Dis 9, 174 (2014).
Edgar, R. C. Muscle: a multiple sequence alignment method with reduced time and space complexity. BMC Bioinformatics 5, 113 (2004).
Emsley, P., Lohkamp, B., Scott, W. G. & Cowtan, K. Features and development of Coot. Acta Crystallogr. D Biol. Crystallogr. 66, 486-501 (2010).
Erzberger, J. P. & Berger, J. M. Evolutionary relationships and structural mechanisms of AAA+ proteins. Annu Rev Biophys Biomol Struct 35, 93-114 (2006).
Glaser, F. et al. ConSurf: identification of functional regions in proteins by surface-mapping of phylogenetic information. Bioinformatics 19, 163-164 (2003).
Goodchild, R. E. & Dauer, W. T. Mislocalization to the nuclear envelope: an effect of the dystonia-causing torsinA mutation. Proc. Natl. Acad. Sci. U.S.A. 101, 847-852 (2004).
Goodchild, R. E. & Dauer, W. T. The AAA+ protein torsinA interacts with a conserved domain present in LAP1 and a novel ER protein. J. Cell Biol. 168, 855-862 (2005).
Goodchild, R. E. et al. Access of torsinA to the inner nuclear membrane is activity dependent and regulated in the endoplasmic reticulum. J. Cell. Sci. 128, 2854-2865 (2015).

(Continued)

*Primary Examiner* — Suzanne M Noakes
*Assistant Examiner* — Jae W Lee
(74) *Attorney, Agent, or Firm* — Bryan D. Zerhusen; Locke Lord LLP

(57) ABSTRACT

A protein composition including TorsinA or TorsinA mutant, LULL1, and a nanobody obtained by immunization using TorsinA and LULL1 is used to grow complex crystals, and three dimensional structures are determined using x-ray data of the crystals. A screening platform is built based on the determined three dimensional structures for designing a drug lead to cure dystonia.

8 Claims, 18 Drawing Sheets

(56) References Cited

PUBLICATIONS

Goodchild, R. E., Kim, C. E. & Dauer, W. T. Loss of the dystonia-associated protein torsinA selectively disrupts the neuronal nuclear envelope. Neuron 48, 923-932 (2005).

Granata, A. & Warner, T. T. The role of torsinA in dystonia. Eur. J. Neurol. 17 Suppl 1, 81-87 (2010).

Granata, A., Koo, S. J., Haucke, V., Schiavo, G. & Warner, T. T. CSN complex controls the stability of selected synaptic proteins via a torsinA-dependent process. EMBO J. 30, 181-193 (2011).

Hanson, P. I. & Whiteheart, S. W. AAA+ proteins: have engine, will work. Nat. Rev. Mol. Cell Biol. 6, 519-529 (2005).

Iyer, L. M., Leipe, D. D., Koonin, E. V. & Aravind, L. Evolutionary history and higher order classification of AAA+ ATPases. J. Struct. Biol. 146, 11-31 (2004).

Jokhi, V. et al. Torsin mediates primary envelopment of large ribonucleoprotein granules at the nuclear envelope. Cell Rep 3, 988-995 (2013).

Jungwirth, M., Dear, M. L., Brown, P., Holbrook, K. & Goodchild, R. Relative tissue expression of homologous torsinB correlates with the neuronal specific importance of DYT1 dystonia-associated torsinA. Hum. Mol. Genet. 19, 888-900 (2010).

Kamm, C. et al. Susceptibility to DYT1 dystonia in European patients is modified by the D216H polymorphism. Neurology 70, 2261-2262 (2008).

Kayman-Kurekci, G. et al. Mutation in TOR1AIP1 encoding LAP1B in a form of muscular dystrophy: a novel gene related to nuclear envelopathies. Neuromuscul. Disord. 24, 624-633 (2014).

Kelley, L. A. & Sternberg, M. J. E. Protein structure prediction on the Web: a case study using the Phyre server. Nat Protoc 4, 363-371 (2009).

Kim, C. E., Perez, A., Perkins, G., Ellisman, M. H. & Dauer, W. T. A molecular mechanism underlying the neural-specific defect in torsinA mutant mice. Proc. Natl. Acad. Sci. U.S.A. 107, 9861-9866 (2010).

Kock, N. et al. Effects of genetic variations in the dystonia protein torsinA: identification of polymorphism at residue 216 as protein modifier. Hum. Mol. Genet. 15, 1355-1364 (2006).

Laudermilch, E. & Schlieker, C. TorsinATPases: structural insights and functional perspectives. Curr. Opin. Cell Biol. 40, 1-7 (2016).

Leung, J. C. et al. Novel mutation in the TOR1A (DYT1) gene in atypical early onset dystonia and polymorphisms in dystonia and early onset parkinsonism. Neurogenetics 3, 133-143 (2001).

Liang, C.-C., Tanabe, L. M., Jou, S., Chi, F. & Dauer, W. T. TorsinA hypofunction causes abnormal twisting movements and sensorimotor circuit neurodegeneration. J. Clin. Invest. 124, 3080-3092 (2014).

McCullough, J. & Sundquist, W. I. Putting a finger in the ring. Nat. Struct. Mol. Biol. 21, 1025-1027 (2014).

Morin, A. et al. Collaboration gets the most out of software. Elife 2, e01456 (2013).

Muyldermans, S. Nanobodies: natural single-domain antibodies. Annu. Rev. Biochem. 82, 775-797 (2013).

Naismith, T. V., Dalal, S. & Hanson, P. I. Interaction of torsinA with its major binding partners is impaired by the dystonia-associated DeltaGAG deletion. J. Biol. Chem. 284, 27866-27874 (2009).

Nery, F. C. et al. TorsinA binds the KASH domain of nesprins and participates in linkage between nuclear envelope and cytoskeleton. J. Cell. Sci. 121, 3476-3486 (2008).

Nery, F. C. et al. TorsinA participates in endoplasmic reticulum-associated degradation. Nat Commun 2, 393 (2011).

Olivares, A. O., Baker, T. A. & Sauer, R. T. Mechanistic insights into bacterial AAA+ proteases and protein-remodelling machines. Nat. Rev. Microbiol. 14, 33-44 (2016).

Otwinowski, Z. & Minor, W. [20] Processing of X-ray diffraction data collected in oscillation mode. Methods in Enzymology 276, 307-326 (Elsevier, 1997).

Ozelius, L. J. et al. The early-onset torsion dystonia gene (DYT1) encodes an ATP-binding protein. Nat. Genet. 17, 40-48 (1997).

Rose, A. E., Brown, R. S. H. & Schlieker, C. Torsins: not your typical AAA+ ATPases. Crit. Rev. Biochem. Mol. Biol. 50, 532-549 (2015).

Sauer, R. T. & Baker, T. A. AAA+ proteases: ATP-fueled machines of protein destruction. Annu. Rev. Biochem. 80, 587-612 (2011).

Soding, J., Biegert, A. & Lupas, A. N. The HHpred interactive server for protein homology detection and structure prediction. Nucleic Acids Res. 33, W244-8 (2005).

Sosa, B. A. et al. How lamina-associated polypeptide 1 (LAP1) activates Torsin. Elife 3, e03239 (2014).

Steeves TD, Day L , Dykeman J et al. The prevalence of primary dystonia: a systematic review and meta-analysis . Mov. Disord. 27 (14) , 1789-1796 (2012) . |CrossRef] [Medline].

Tusnády, G. E. & Simon, I. The HMMTOP transmembrane topology prediction server. Bioinformatics 17, 849-850 (2001).

Vander Heyden, A. B., Naismith, T. V., Snapp, E. L., Hodzic, D. & Hanson, P. I. LULL1 retargets TorsinA to the nuclear envelope revealing an activity that is impaired by the DYT1 dystonia mutation. Mol. Biol. Cell 20,2661-2672 (2009).

Vulinovic, F. et al. Unraveling cellular phenotypes of novel TorsinA/TOR1A mutations. Hum. Mutat. 35, 1114-1122 (2014).

Waterhouse, A. M., Procter, J. B., Martin, D. M. A., Clamp, M. & Barton, G. J. Jalview Version 2—a multiple sequence alignment editor and analysis workbench. Bioinformatics 25,1189-1191 (2009).

Wendler, P., Ciniawsky, S., Kock, M. & Kube, S. Structure and function of the AAA+ nucleotide binding pocket. Biochim. Biophys. Acta 1823,2-14 (2012).

Zeymer, C., Barends, T. R. M., Werbeck, N. D., Schlichting, I. & Reinstein, J. Elements in nucleotide sensing and hydrolysis of the AAA+ disaggregation machine ClpB: a structure-based mechanistic dissection of a molecular motor. Acta Crystallogr. D Biol. Crystallogr. 70,582-595 (2014).

Zhao, C., Brown, R. S. H., Chase, A. R., Eisele, M. R. & Schlieker, C. Regulation of TorsinATPases by LAP1 and LULL1. Proc. Natl. Acad. Sci. U.S.A. 110, E1545-54 (2013).

Zhu, L., Millen, L., Mendoza, J. L. & Thomas, P. J. A unique redox-sensing sensor II motif in TorsinA plays a critical role in nucleotide and partner binding. J. Biol. Chem. 285,37271-37280 (2010).

Zhu, L., Wrabl, J. O., Hayashi, A. P., Rose, L. S. & Thomas, P. J. The torsin-family AAA+protein OOC-5 contains a critical disulfide adjacent to Sensor-II that couples redox state to nucleotide binding. Mol. Biol. Cell 19,3599-3612 (2008).

Zirn, B. et al. Novel TOR1A mutation p.Arg288Gln in early-onset dystonia (DYT1). J. Neurol. Neurosurg. Psychiatr. 79, 1327-1330 (2008).

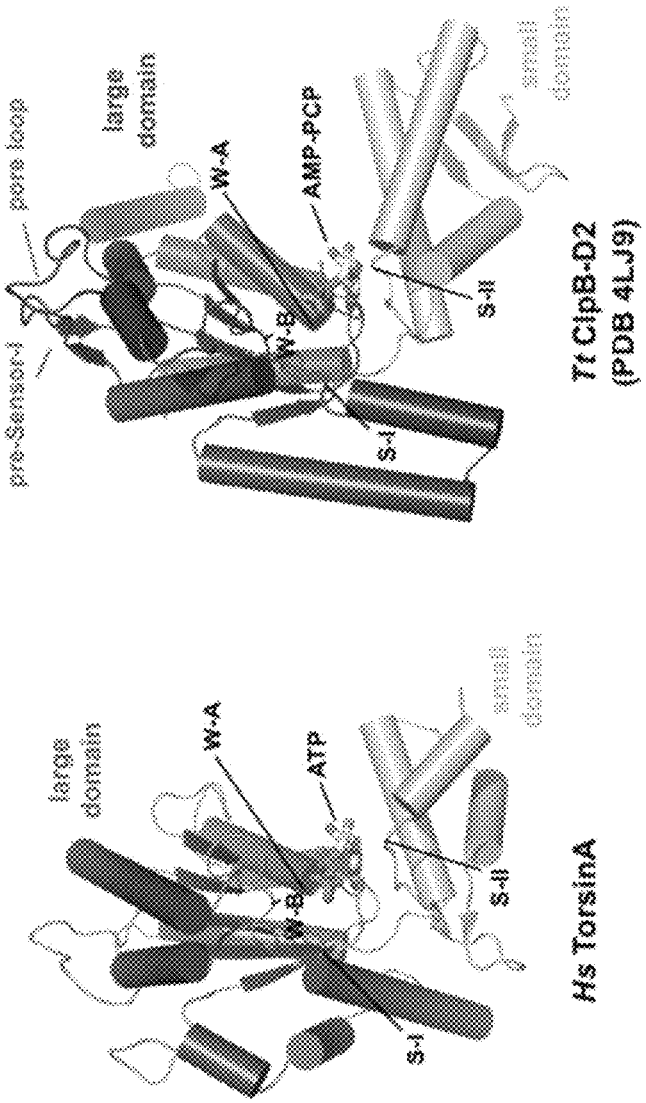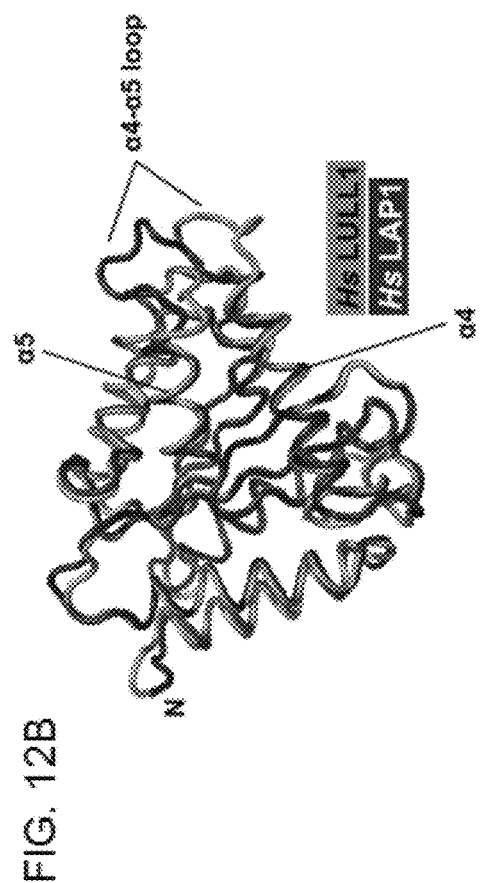
FIG. 12A
FIG. 12B

FIG. 14

Table 1. Data collection and refinement statistics

| | TorsinA-LULL1$_{233-470}$ | TorsinAΔE-LULL1$_{233-470}$ |
|---|---|---|
| PDB Code | 5J1S | 5J1T |
| Data collection | | |
| Space group | P2$_1$2$_1$2$_1$ | P2$_1$2$_1$2$_1$ |
| Cell dimensions | | |
|   $a, b, c$ (Å) | 75.7, 90.7, 105.1 | 75.5, 88.1, 105.4 |
|   α, β, γ (°) | 90.0, 90.0, 90.0 | 90.0, 90.0, 90.0 |
| Resolution (Å) | 61 – 1.40 (1.45 – 1.40)[a] | 68 – 1.40 (1.45 – 1.40) |
| $R_{sym}$ | 0.06 (0.88) | 0.10 (1.98) |
| $R_{pim}$ | 0.03 (0.43) | 0.03 (0.60) |
| $I / \sigma I$ | 33.0 (1.5) | 30.8 (1.3) |
| Completeness (%) | 94.7 (67.5) | 97.9 (96.5) |
| Redundancy | 5.7 (4.4) | 12.4 (11.3) |
| CC(1/2) | 1.00 (0.65) | 1.00 (0.58) |
| Refinement | | |
| Resolution (Å) | 61.4 – 1.40 | 67.7 – 1.40 |
| No. reflections | 132956 | 134333 |
| $R_{work}$ / $R_{free}$ | 0.142/0.188 | 0.148/0.177 |
| No. atoms | 5898 | 5927 |
|   Protein | 5241 | 5244 |
|   Ligand/ion | 35 | 47 |
|   Water | 622 | 636 |
| $B$ factors (Å$^2$) | | |
|   Protein | 31.3 | 24.0 |
|   Ligand/ion | 23.2 | 17.2 |
|   Water | 43.1 | 33.6 |
| r.m.s. deviations | | |
|   Bond lengths (Å) | 0.014 | 0.017 |
|   Bond angles (°) | 1.25 | 1.71 |
| Ramachandran | | |
|   Favored/allowed/outliers (%) | 98.0/1.7/0.0 | 98.6/1.4/0.0 |

[a]Values in parentheses are for highest-resolution shell. One crystal was used for each dataset.

FIG. 17

Table2. Dystonia mutations

| Protein | Mutation | Structural consequence | Reference |
|---|---|---|---|
| TorsinA | ΔE302/303 | Weakened LAP1/LULL1 binding | 1 |
| TorsinA | ΔF323-Y328 | Weakened LAP1/LULL1 binding | 47 |
| TorsinA | R288Q | Weakened LAP1/LULL1 binding | 48 |
| TorsinA | F205I | Folding problem | 49 |
| TorsinA | D194V | Change to the conserved, noncatalytic interface | 50 |
| TorsinA | ΔA14-P15 | Improper cellular targeting | 51 |
| TorsinA | E121K | Charge inversion at the membrane proximal interface | 51 |
| TorsinA | V129I | Folding problem | 52 |
| TorsinA | D216H (modifier) | Surface change; consequence unclear | 53, 54 |
| LAP1 | c.186delG (p.E62fsTer25) | Lack of the luminal activation domain of LAP1 | 55 |
| LAP1 | E482A* | Improper folding | 56 |

*Assesment based on the equivalent residue in LULL1 (E368).

FIG. 18

SEQUENCE LISTING

```
<160> NUMBER OF SEQ ID NOS: 50

<210> SEQ ID NO 1
<211> LENGTH: 282
<212> TYPE: PRT
<213> ORGANISM: Homo sapiens

<400> SEQUENCE: 1

Gly Gln Lys Arg Ser Leu Ser Arg Glu Ala Leu Gln Lys Asp Leu Asp
1               5                   10                  15

Asp Asn Leu Phe Gly Gln His Leu Ala Lys Lys Ile Ile Leu Asn Ala
            20                  25                  30

Val Phe Gly Phe Ile Asn Asn Pro Lys Pro Lys Lys Pro Leu Thr Leu
        35                  40                  45

Ser Leu His Gly Trp Thr Gly Thr Gly Lys Asn Phe Val Ser Lys Ile
    50                  55                  60

Ile Ala Glu Asn Ile Tyr Glu Gly Gly Leu Asn Ser Asp Tyr Val His
65                  70                  75                  80

Leu Phe Val Ala Thr Leu His Phe Pro His Ala Ser Asn Ile Thr Leu
                85                  90                  95

Tyr Lys Asp Gln Leu Gln Leu Trp Ile Arg Gly Asn Val Ser Ala Cys
            100                 105                 110

Ala Arg Ser Ile Phe Ile Phe Asp Glu Met Asp Lys Met His Ala Gly
        115                 120                 125
```

```
Leu Ile Asp Ala Ile Lys Pro Phe Leu Asp Tyr Tyr Asp Leu Val Asp
130                 135                 140

Gly Val Ser Tyr Gln Lys Ala Met Phe Ile Phe Leu Ser Asn Ala Gly
145                 150                 155                 160

Ala Glu Arg Ile Thr Asp Val Ala Leu Asp Phe Trp Arg Ser Gly Lys
                165                 170                 175

Gln Arg Glu Asp Ile Lys Leu Lys Asp Ile Glu His Ala Leu Ser Val
                180                 185                 190

Ser Val Phe Asn Asn Lys Asn Ser Gly Phe Trp His Ser Ser Leu Ile
                195                 200                 205

Asp Arg Asn Leu Ile Asp Tyr Phe Val Pro Phe Leu Pro Leu Glu Tyr
210                 215                 220

Lys His Leu Lys Met Cys Ile Arg Val Glu Met Gln Ser Arg Gly Tyr
225                 230                 235                 240

Glu Ile Asp Glu Asp Ile Val Ser Arg Val Ala Glu Glu Met Thr Phe
                245                 250                 255

Phe Pro Lys Glu Glu Arg Val Phe Ser Asp Lys Gly Cys Lys Thr Val
                260                 265                 270

Phe Thr Lys Leu Asp Tyr Tyr Tyr Asp Asp
                275                 280

<210> SEQ ID NO 2
<211> LENGTH: 282
<212> TYPE: PRT
<213> ORGANISM: Artificial Sequence
<220> FEATURE:
<223> OTHER INFORMATION: Synthetic

<400> SEQUENCE: 2

Gly Gln Lys Arg Ser Leu Ser Arg Glu Ala Leu Gln Lys Asp Leu Asp
1               5                   10                  15

Asp Asn Leu Phe Gly Gln His Leu Ala Lys Lys Ile Ile Leu Asn Ala
                20                  25                  30

Val Phe Gly Phe Ile Asn Asn Pro Lys Pro Lys Lys Pro Leu Thr Leu
            35                  40                  45

Ser Leu His Gly Trp Thr Gly Thr Gly Lys Asn Phe Val Ser Lys Ile
50                  55                  60

Ile Ala Glu Asn Ile Tyr Glu Gly Gly Leu Asn Ser Asp Tyr Val His
65                  70                  75                  80

Leu Phe Val Ala Thr Leu His Phe Pro His Ala Ser Asn Ile Thr Leu
                85                  90                  95

Tyr Lys Asp Gln Leu Gln Leu Trp Ile Arg Gly Asn Val Ser Ala Cys
                100                 105                 110

Ala Arg Ser Ile Phe Ile Phe Asp Gln Met Asp Lys Met His Ala Gly
            115                 120                 125

Leu Ile Asp Ala Ile Lys Pro Phe Leu Asp Tyr Tyr Asp Leu Val Asp
130                 135                 140

Gly Val Ser Tyr Gln Lys Ala Met Phe Ile Phe Leu Ser Asn Ala Gly
145                 150                 155                 160

Ala Glu Arg Ile Thr Asp Val Ala Leu Asp Phe Trp Arg Ser Gly Lys
                165                 170                 175

Gln Arg Glu Asp Ile Lys Leu Lys Asp Ile Glu His Ala Leu Ser Val
                180                 185                 190

Ser Val Phe Asn Asn Lys Asn Ser Gly Phe Trp His Ser Ser Leu Ile
                195                 200                 205
```

```
Asp Arg Asn Leu Ile Asp Tyr Phe Val Pro Phe Leu Pro Leu Glu Tyr
    210                 215                 220

Lys His Leu Lys Met Cys Ile Arg Val Glu Met Gln Ser Arg Gly Tyr
225                 230                 235                 240

Glu Ile Asp Glu Asp Ile Val Ser Arg Val Ala Glu Glu Met Thr Phe
            245                 250                 255

Phe Pro Lys Glu Glu Arg Val Phe Ser Asp Lys Gly Cys Lys Thr Val
            260                 265                 270

Phe Thr Lys Leu Asp Tyr Tyr Tyr Asp Asp
            275                 280
```

<210> SEQ ID NO 3
<211> LENGTH: 281
<212> TYPE: PRT
<213> ORGANISM: Artificial Sequence
<220> FEATURE:
<223> OTHER INFORMATION: Synthetic

<400> SEQUENCE: 3

```
Gly Gln Lys Arg Ser Leu Ser Arg Glu Ala Leu Gln Lys Asp Leu Asp
1               5                   10                  15

Asp Asn Leu Phe Gly Gln His Leu Ala Lys Lys Ile Ile Leu Asn Ala
            20                  25                  30

Val Phe Gly Phe Ile Asn Asn Pro Lys Pro Lys Lys Pro Leu Thr Leu
        35                  40                  45

Ser Leu His Gly Trp Thr Gly Thr Gly Lys Asn Phe Val Ser Lys Ile
    50                  55                  60

Ile Ala Glu Asn Ile Tyr Glu Gly Gly Leu Asn Ser Asp Tyr Val His
65                  70                  75                  80

Leu Phe Val Ala Thr Leu His Phe Pro His Ala Ser Asn Ile Thr Leu
                85                  90                  95

Tyr Lys Asp Gln Leu Gln Leu Trp Ile Arg Gly Asn Val Ser Ala Cys
            100                 105                 110

Ala Arg Ser Ile Phe Ile Phe Asp Gln Met Asp Lys Met His Ala Gly
        115                 120                 125

Leu Ile Asp Ala Ile Lys Pro Phe Leu Asp Tyr Tyr Asp Leu Val Asp
    130                 135                 140

Gly Val Ser Tyr Gln Lys Ala Met Phe Ile Phe Leu Ser Asn Ala Gly
145                 150                 155                 160

Ala Glu Arg Ile Thr Asp Val Ala Leu Asp Phe Trp Arg Ser Gly Lys
                165                 170                 175

Gln Arg Glu Asp Ile Lys Leu Lys Asp Ile Glu His Ala Leu Ser Val
            180                 185                 190

Ser Val Phe Asn Asn Lys Asn Ser Gly Phe Trp His Ser Ser Leu Ile
        195                 200                 205

Asp Arg Asn Leu Ile Asp Tyr Phe Val Pro Phe Leu Pro Leu Glu Tyr
    210                 215                 220

Lys His Leu Lys Met Cys Ile Arg Val Glu Met Gln Ser Arg Gly Tyr
225                 230                 235                 240

Glu Ile Asp Glu Asp Ile Val Ser Arg Val Ala Glu Met Thr Phe Phe
                245                 250                 255

Pro Lys Glu Glu Arg Val Phe Ser Asp Lys Gly Cys Lys Thr Val Phe
            260                 265                 270

Thr Lys Leu Asp Tyr Tyr Asp Asp
        275                 280
```

<210> SEQ ID NO 4
<211> LENGTH: 238
<212> TYPE: PRT
<213> ORGANISM: Homo sapiens

<400> SEQUENCE: 4

Ser Ser Val Asn Ser Tyr Tyr Ser Ser Pro Ala Gln Gln Val Pro Lys
1               5                   10                  15

Asn Pro Ala Leu Glu Ala Phe Leu Ala Gln Phe Ser Gln Leu Glu Asp
            20                  25                  30

Lys Phe Pro Gly Gln Ser Ser Phe Leu Trp Gln Arg Gly Arg Lys Phe
        35                  40                  45

Leu Gln Lys His Leu Asn Ala Ser Asn Pro Thr Glu Pro Ala Thr Ile
    50                  55                  60

Ile Phe Thr Ala Ala Arg Glu Gly Arg Glu Thr Leu Lys Cys Leu Ser
65                  70                  75                  80

His His Val Ala Asp Ala Tyr Thr Ser Ser Gln Lys Val Ser Pro Ile
                85                  90                  95

Gln Ile Asp Gly Ala Gly Arg Thr Trp Gln Asp Ser Asp Thr Val Lys
            100                 105                 110

Leu Leu Val Asp Leu Glu Leu Ser Tyr Gly Phe Glu Asn Gly Gln Lys
        115                 120                 125

Ala Ala Val Val His His Phe Glu Ser Phe Pro Ala Gly Ser Thr Leu
    130                 135                 140

Ile Phe Tyr Lys Tyr Cys Asp His Glu Asn Ala Ala Phe Lys Asp Val
145                 150                 155                 160

Ala Leu Val Leu Thr Val Leu Leu Glu Glu Glu Thr Leu Glu Ala Ser
                165                 170                 175

Val Gly Pro Arg Glu Thr Glu Glu Lys Val Arg Asp Leu Leu Trp Ala
            180                 185                 190

Lys Phe Thr Asn Ser Asp Thr Pro Thr Ser Phe Asn His Met Asp Ser
        195                 200                 205

Asp Lys Leu Ser Gly Leu Trp Ser Arg Ile Ser His Leu Val Leu Pro
    210                 215                 220

Val Gln Pro Val Ser Ser Ile Glu Glu Gln Gly Cys Leu Phe
225                 230                 235

<210> SEQ ID NO 5
<211> LENGTH: 123
<212> TYPE: PRT
<213> ORGANISM: Artificial Sequence
<220> FEATURE:
<223> OTHER INFORMATION: Synthetic

<400> SEQUENCE: 5

Met Gln Val Gln Leu Val Glu Thr Gly Gly Gly Leu Val Gln Ala Gly
1               5                   10                  15

Gly Ser Leu Arg Leu Ser Cys Ala Ala Ser Gly Asn Ile Phe Ser Phe
            20                  25                  30

Asn Val Met Gly Trp Tyr Arg Gln Ala Pro Gly Lys Gln Arg Glu Leu
        35                  40                  45

Val Ala Ala Ile Thr Ser Gly Asp Thr Thr Tyr Ala Asp Ser Val
    50                  55                  60

Gln Gly Arg Phe Thr Ile Ser Arg Asp Asn Ala Lys Asn Ala Val Tyr
65                  70                  75                  80

Leu Gln Met Asn Ser Leu Thr Pro Glu Asp Thr Ala Val Tyr Phe Cys

```
                85                  90                  95
Asn Ala Arg Arg Asn Pro Ile Asn Gly Pro Tyr Tyr Thr Thr Ala Tyr
                100                 105                 110

Trp Gly Gln Gly Thr Gln Val Thr Val Ser Ser
                115                 120

<210> SEQ ID NO 6
<211> LENGTH: 849
<212> TYPE: DNA
<213> ORGANISM: Homo sapiens

<400> SEQUENCE: 6
gggcagaagc ggagccttag ccgggaggca ctgcagaagg atctggacga caacctcttt      60
ggacagcatc ttgcaaagaa aatcatctta aatgccgtgt ttggtttcat aaacaaccca     120
aagcccaaga aacctctcac gctctccctg cacgggtgga caggcaccgg caaaaatttc     180
gtcagcaaga tcatcgcaga gaatatttac gagggtggtc tgaacagtga ctatgtccac     240
ctgtttgtgg ccacattgca ctttccacat gcttcaaaca tcaccttgta caaggatcag     300
ttacagttgt ggattcgagg caacgtgagt gcctgtgcga ggtccatctt catatttgat     360
gaaatggata agatgcatgc aggcctcata gatgccatca agccttccct cgactattat     420
gacctggtgg atggggtctc ctaccagaaa gccatgttca tatttctcag caatgctgga     480
gcagaaagga tcacagatgt ggctttggat ttctggagga gtggaaagca gagggaagac     540
atcaagctca aagacattga acacgcgttg tctgtgtcgg ttttcaataa caagaacagt     600
ggcttctggc acagcagctt aattgaccgg aacctcattg attatttgt tcccttcctc     660 cccctggaat acaaacacct aaaaatgtgt atccgagtgg aaatgcagtc ccgaggctat     720
gaaattgatg aagacattgt aagcagagtg gctgaggaga tgacttttt ccccaaagag     780 gagagagttt tctcagataa aggctgcaaa acggtgttca ccaagttaga ttattactac     840
gatgattga                                                             849

<210> SEQ ID NO 7
<211> LENGTH: 849
<212> TYPE: DNA
<213> ORGANISM: Artificial Sequence
<220> FEATURE:
<223> OTHER INFORMATION: Synthetic

<400> SEQUENCE: 7
gggcagaagc ggagccttag ccgggaggca ctgcagaagg atctggacga caacctcttt      60
ggacagcatc ttgcaaagaa aatcatctta aatgccgtgt ttggtttcat aaacaaccca     120
aagcccaaga aacctctcac gctctccctg cacgggtgga caggcaccgg caaaaatttc     180
gtcagcaaga tcatcgcaga gaatatttac gagggtggtc tgaacagtga ctatgtccac     240
ctgtttgtgg ccacattgca ctttccacat gcttcaaaca tcaccttgta caaggatcag     300
ttacagttgt ggattcgagg caacgtgagt gcctgtgcga ggtccatctt catatttgat     360
caaatggata agatgcatgc aggcctcata gatgccatca agccttccct cgactattat     420
gacctggtgg atggggtctc ctaccagaaa gccatgttca tatttctcag caatgctgga     480
gcagaaagga tcacagatgt ggctttggat ttctggagga gtggaaagca gagggaagac     540
atcaagctca aagacattga acacgcgttg tctgtgtcgg ttttcaataa caagaacagt     600
ggcttctggc acagcagctt aattgaccgg aacctcattg attatttgt tcccttcctc     660 cccctggaat acaaacacct aaaaatgtgt atccgagtgg aaatgcagtc ccgaggctat     720
```

```
gaaattgatg aagacattgt aagcagagtg gctgaggaga tgacattttt ccccaaagag      780
gagagagttt tctcagataa aggctgcaaa acggtgttca ccaagttaga ttattactac      840
gatgattga                                                              849

<210> SEQ ID NO 8
<211> LENGTH: 846
<212> TYPE: DNA
<213> ORGANISM: Artificial Sequence
<220> FEATURE:
<223> OTHER INFORMATION: Synthetic

<400> SEQUENCE: 8
gggcagaagc ggagccttag ccgggaggca ctgcagaagg atctggacga caacctcttt       60
ggacagcatc ttgcaaagaa aatcatctta aatgccgtgt ttggtttcat aaacaaccca      120
aagcccaaga aacctctcac gctctccctg cacgggtgga caggcaccgg caaaaatttc      180
gtcagcaaga tcatcgcaga gaatatttac gagggtggtc tgaacagtga ctatgtccac      240
ctgtttgtgg ccacattgca cttcccacat gcttcaaaca tcaccttgta caaggatcag      300
ttacagttgt ggattcgagg caacgtgagt gcctgtgcga ggtccatctt catatttgat      360
caaatggata agatgcatgc aggcctcata gatgccatca agcctttcct cgactattat      420
gacctggtgg atggggtctc ctaccagaaa gccatgttca tatttctcag caatgctgga      480
gcagaaagga tcacagatgt ggctttggat tctggagga gtggaaagca gagggaagac       540
atcaagctca aagacattga acacgcgttg tctgtgtcgg ttttcaataa caagaacagt      600
ggcttctggc acagcagctt aattgaccgg aacctcattg attattttgt tcccttcctc      660
cccctggaat acaaacacct aaaaatgtgt atccgagtgg aaatgcagtc ccgaggctat      720
gaaattgatg aagacattgt aagcagagtg gctgagatga cattttttccc caagaggag      780 agagttttct cagataaagg ctgcaaaacg tgttcacca agttagatta ttactacgat      840
gattga                                                                 846

<210> SEQ ID NO 9
<211> LENGTH: 717
<212> TYPE: DNA
<213> ORGANISM: Homo sapiens

<400> SEQUENCE: 9
agttctgtga atagctacta ttcctctcca gcccagcaag tgcccaaaaa tccagctttg       60
gaggcctttt tggcccagtt tagccaattg gaagataaat ttccaggcca gagttccttc      120
ctgtggcaga gaggacggaa gtttctccag aagcacctca atgcttccaa ccccactgag      180
ccagccacca tcatatttac agcagctcgg gaggaagag agaccctgaa gtgcctgagc       240
caccatgttg cagatgccta cacctcttcc cagaaagtct ctcccattca gattgatggg      300
gctggaagga cctggcagga cagtgacacg gtcaagctgt tggttgacct ggagctgagc      360
tatgggtttg agaatggcca gaaggctgct gtggtacacc acttcgaatc cttccctgcc      420
ggctccactt tgatcttcta taagtattgt gatcatgaga atgctgcctt taaagatgtg      480
gccctggtcc tgactgttct gctagaggag gaaacattag aagcaagtgt aggcccaagg      540
gaaacggaag aaaaagtgag agacttactc tgggccaagt ttaccaactc tgacactccc      600
acctccttca accacatgga ctcagacaaa ttgagtgggc tgtggagccg aatttcacac      660
ctggtactgc cagtccagcc agtgagtagc atagaagaac agggtgcct tttctaa         717
```

<210> SEQ ID NO 10
<211> LENGTH: 372
<212> TYPE: DNA
<213> ORGANISM: Artificial Sequence
<220> FEATURE:
<223> OTHER INFORMATION: Synthetic

<400> SEQUENCE: 10

```
atgcaggtgc agctcgtgga gacaggcggg gggttggtgc aggctggggg ctctctgagg      60
ctctcctgtg cagcctctgg aaacatcttc agtttcaatg tcatgggctg gtaccgccag     120
gctccaggga agcagcgcga gttggtcgca gcgatcacga gtggtgatac gacaacctat     180
gcagactccg tgcagggccg attcaccatc tccagagaca atgccaagaa cgcggtgtat     240
ctgcaaatga acagcctgac acctgaggac acggccgtct atttctgtaa tgcgcggcgc     300
aatccgatta atggtcctta ctacaccaca gcctactggg gccaggggac ccaggtcacc     360
gtctcctcat ga                                                         372
```

<210> SEQ ID NO 11
<211> LENGTH: 292
<212> TYPE: PRT
<213> ORGANISM: Homo sapiens

<400> SEQUENCE: 11

```
Arg Leu Tyr Cys Leu Phe Ala Glu Cys Cys Gly Gln Lys Arg Ser Leu
1               5                   10                  15

Ser Arg Glu Ala Leu Gln Lys Asp Leu Asp Asp Asn Leu Phe Gly Gln
            20                  25                  30

His Leu Ala Lys Lys Ile Ile Leu Asn Ala Val Phe Gly Phe Ile Asn
        35                  40                  45

Asn Pro Lys Pro Lys Pro Leu Thr Leu Ser Leu His Gly Trp Thr
    50                  55                  60

Gly Thr Gly Lys Asn Phe Val Ser Lys Ile Ile Ala Glu Asn Ile Tyr
65                  70                  75                  80

Glu Gly Gly Leu Asn Ser Asp Tyr Val His Leu Phe Val Ala Thr Leu
                85                  90                  95

His Phe Pro His Ala Ser Asn Ile Thr Leu Tyr Lys Asp Gln Leu Gln
            100                 105                 110

Leu Trp Ile Arg Gly Asn Val Ser Ala Cys Ala Arg Ser Ile Phe Ile
        115                 120                 125

Phe Asp Glu Met Asp Lys Met His Ala Gly Leu Ile Asp Ala Ile Lys
    130                 135                 140

Pro Phe Leu Asp Tyr Tyr Asp Leu Val Asp Gly Val Ser Tyr Gln Lys
145                 150                 155                 160

Ala Met Phe Ile Phe Leu Ser Asn Ala Gly Ala Glu Arg Ile Thr Asp
                165                 170                 175

Val Ala Leu Asp Phe Trp Arg Ser Gly Lys Gln Arg Glu Asp Ile Lys
            180                 185                 190

Leu Lys Asp Ile Glu His Ala Leu Ser Val Ser Val Phe Asn Asn Lys
        195                 200                 205

Asn Ser Gly Phe Trp His Ser Ser Leu Ile Asp Arg Asn Leu Ile Asp
    210                 215                 220

Tyr Phe Val Pro Phe Leu Pro Leu Glu Tyr Lys His Leu Lys Met Cys
225                 230                 235                 240

Ile Arg Val Glu Met Gln Ser Arg Gly Tyr Glu Ile Asp Glu Asp Ile
                245                 250                 255
```

```
Val Ser Arg Val Ala Glu Glu Met Thr Phe Phe Pro Lys Glu Glu Arg
            260                 265                 270

Val Phe Ser Asp Lys Gly Cys Lys Thr Val Phe Thr Lys Leu Asp Tyr
        275                 280                 285

Tyr Tyr Asp Asp
    290

<210> SEQ ID NO 12
<211> LENGTH: 288
<212> TYPE: PRT
<213> ORGANISM: Homo sapiens

<400> SEQUENCE: 12

Asp Ile Tyr Cys Arg Phe Ala Glu Cys Cys Arg Glu Arg Pro Leu
1               5                   10                  15

Asn Ala Ser Ala Leu Lys Leu Asp Leu Glu Glu Lys Leu Phe Gly Gln
            20                  25                  30

His Leu Ala Thr Glu Val Ile Phe Lys Ala Leu Thr Gly Phe Arg Asn
        35                  40                  45

Asn Lys Asn Pro Lys Lys Pro Leu Thr Leu Ser Leu His Gly Trp Ala
    50                  55                  60

Gly Thr Gly Lys Asn Phe Val Ser Gln Ile Val Ala Glu Asn Leu His
65                  70                  75                  80

Pro Lys Gly Leu Lys Ser Asn Phe Val His Leu Phe Val Ser Thr Leu
                85                  90                  95

His Phe Pro His Glu Gln Lys Ile Lys Leu Tyr Gln Asp Gln Leu Gln
            100                 105                 110

Lys Trp Ile Arg Gly Asn Val Ser Ala Cys Ala Asn Ser Val Phe Ile
        115                 120                 125

Phe Asp Glu Met Asp Lys Leu His Pro Gly Ile Ile Asp Ala Ile Lys
    130                 135                 140

Pro Phe Leu Asp Tyr Tyr Glu Gln Val Asp Gly Val Ser Tyr Arg Lys
145                 150                 155                 160

Ala Ile Phe Ile Phe Leu Ser Asn Ala Gly Asp Leu Ile Thr Lys Thr
                165                 170                 175

Ala Leu Asp Phe Trp Arg Ala Gly Arg Lys Arg Glu Asp Ile Gln Leu
            180                 185                 190

Lys Asp Leu Glu Pro Val Leu Ser Val Gly Val Phe Asn Asn Lys His
        195                 200                 205

Ser Gly Leu Trp His Ser Gly Leu Ile Asp Lys Asn Leu Ile Asp Tyr
    210                 215                 220

Phe Ile Pro Phe Leu Pro Leu Glu Tyr Arg His Val Lys Met Cys Val
225                 230                 235                 240

Arg Ala Glu Met Arg Ala Arg Gly Ser Ala Ile Asp Glu Asp Ile Val
                245                 250                 255

Thr Arg Val Ala Glu Glu Met Thr Phe Phe Pro Arg Asp Glu Lys Ile
            260                 265                 270

Tyr Ser Asp Lys Gly Cys Lys Thr Val Gln Ser Arg Leu Asp Phe His
        275                 280                 285

<210> SEQ ID NO 13
<211> LENGTH: 282
<212> TYPE: PRT
<213> ORGANISM: Homo sapiens

<400> SEQUENCE: 13
```

Phe Cys Glu Cys Asp Phe Arg Pro Asp Leu Pro Gly Leu Glu Cys Asp
1               5                   10                  15

Leu Ala Gln His Leu Ala Gly Gln His Leu Ala Lys Ala Leu Val Val
            20                  25                  30

Lys Ala Leu Lys Ala Phe Val Arg Asp Pro Ala Pro Thr Lys Pro Leu
        35                  40                  45

Val Leu Ser Leu His Gly Trp Thr Gly Thr Gly Lys Ser Tyr Val Ser
50                  55                  60

Ser Leu Leu Ala His Tyr Leu Phe Gln Gly Gly Leu Arg Ser Pro Arg
65                  70                  75                  80

Val His His Phe Ser Pro Val Leu His Phe Pro His Pro Ser His Ile
                85                  90                  95

Glu Arg Tyr Lys Lys Asp Leu Lys Ser Trp Val Gln Gly Asn Leu Thr
            100                 105                 110

Ala Cys Gly Arg Ser Leu Phe Leu Phe Asp Glu Met Asp Lys Met Pro
        115                 120                 125

Pro Gly Leu Met Glu Val Leu Arg Pro Phe Leu Gly Ser Ser Trp Val
    130                 135                 140

Val Tyr Gly Thr Asn Tyr Arg Lys Ala Ile Phe Ile Phe Ile Ser Asn
145                 150                 155                 160

Thr Gly Gly Lys Gln Ile Asn Gln Val Ala Leu Glu Ala Trp Arg Ser
                165                 170                 175

Arg Arg Asp Arg Glu Glu Ile Leu Leu Gln Glu Leu Glu Pro Val Ile
            180                 185                 190

Ser Arg Ala Val Leu Asp Asn Pro His His Gly Phe Ser Asn Ser Gly
        195                 200                 205

Ile Met Glu Glu Arg Leu Leu Asp Ala Val Val Pro Phe Leu Pro Leu
    210                 215                 220

Gln Arg His His Val Arg His Cys Val Leu Asn Glu Leu Ala Gln Leu
225                 230                 235                 240

Gly Leu Glu Pro Arg Asp Glu Val Val Gln Ala Val Leu Asp Ser Thr
                245                 250                 255

Thr Phe Phe Pro Glu Asp Glu Gln Leu Phe Ser Ser Asn Gly Cys Lys
            260                 265                 270

Thr Val Ala Ser Arg Ile Ala Phe Phe Leu
        275                 280

<210> SEQ ID NO 14
<211> LENGTH: 295
<212> TYPE: PRT
<213> ORGANISM: Homo sapiens

<400> SEQUENCE: 14

Thr Trp Tyr Cys Ser Phe Lys Asp Cys Cys Pro Arg Gly Asp Cys Arg
1               5                   10                  15

Ile Ser Asn Asn Phe Thr Gly Leu Glu Trp Asp Leu Asn Val Arg Leu
            20                  25                  30

His Gly Gln His Leu Val Gln Gln Leu Val Leu Arg Thr Val Arg Gly
        35                  40                  45

Tyr Leu Glu Thr Pro Gln Pro Glu Lys Ala Leu Ala Leu Ser Phe His
    50                  55                  60

Gly Trp Ser Gly Thr Gly Lys Asn Phe Val Ala Arg Met Leu Val Glu
65                  70                  75                  80

Asn Leu Tyr Arg Asp Gly Leu Met Ser Asp Cys Val Arg Met Phe Ile

```
                    85                  90                  95

Ala Thr Phe His Phe Pro His Pro Lys Tyr Val Asp Leu Tyr Lys Glu
            100                 105                 110

Gln Leu Met Ser Gln Ile Arg Glu Thr Gln Gln Leu Cys His Gln Thr
            115                 120                 125

Leu Phe Ile Phe Asp Glu Ala Glu Lys Leu His Pro Gly Leu Leu Glu
130                 135                 140

Val Leu Gly Pro His Leu Glu Arg Arg Ala Pro Glu Gly His Arg Ala
145                 150                 155                 160

Glu Ser Pro Trp Thr Ile Phe Leu Phe Leu Ser Asn Leu Arg Gly Asp
                165                 170                 175

Ile Ile Asn Glu Val Val Leu Lys Leu Leu Lys Ala Gly Trp Ser Arg
                180                 185                 190

Glu Glu Ile Thr Met Glu His Leu Glu Pro His Leu Gln Ala Glu Ile
            195                 200                 205

Val Glu Thr Ile Asp Asn Gly Phe Gly His Ser Arg Leu Val Lys Glu
            210                 215                 220

Asn Leu Ile Asp Tyr Phe Ile Pro Phe Leu Pro Leu Glu Tyr Arg His
225                 230                 235                 240

Val Arg Leu Cys Ala Arg Asp Ala Phe Leu Ser Gln Glu Leu Leu Tyr
                245                 250                 255

Lys Glu Glu Thr Leu Asp Glu Ile Ala Gln Met Met Val Tyr Val Pro
            260                 265                 270

Lys Glu Glu Gln Leu Phe Ser Ser Gln Gly Cys Lys Ser Ile Ser Gln
            275                 280                 285

Arg Ile Asn Tyr Phe Leu Ser
290                 295

<210> SEQ ID NO 15
<211> LENGTH: 289
<212> TYPE: PRT
<213> ORGANISM: Ornithorhynchus anatinus

<400> SEQUENCE: 15

Ser Leu Tyr Cys Tyr Phe Thr Glu Cys Cys Ala Pro Lys Arg Gly Leu
1               5                   10                  15

Gly Arg Ala Ala Leu Arg Lys Asp Leu Asp Arg Lys Leu Phe Gly Gln
            20                  25                  30

His Leu Ala Lys Lys Val Ile Leu Asn Ala Val Ser Gly Phe Val Ser
            35                  40                  45

Asn Pro Lys Pro Lys Pro Leu Thr Leu Ser Leu His Gly Trp Thr
        50                  55                  60

Gly Thr Gly Lys Asn Phe Ala Ser Lys Ile Ile Ala Glu Asn Ile Tyr
65                  70                  75                  80

Asp Gly Gly Pro Lys Ser Asp Tyr Val His Gln Phe Val Ala Thr Leu
                85                  90                  95

His Phe Pro His Ala Gln Asn Leu Asp Gln Tyr Lys Asp Gln Leu Gln
            100                 105                 110

Leu Trp Ile Arg Gly Asn Val Ser Ala Cys Ser Arg Ser Ile Phe Ile
            115                 120                 125

Phe Asp Glu Met Asp Lys Met Pro Ser Gly Leu Ile Asp Ala Ile Lys
            130                 135                 140

Pro Phe Leu Asp Tyr Tyr Asp Leu Val Asp Gly Val Ser Tyr Gln Lys
145                 150                 155                 160
```

Ala Ile Phe Ile Phe Leu Ser Asn Ala Gly Ala Glu Arg Ile Thr Asp
            165                 170                 175

Val Ala Leu Asp Phe Trp Lys Ser Gly Arg Glu Arg Glu Ile Lys
        180                 185                 190

Leu Lys Asp Met Glu His Ala Leu Ser Val Ser Ile Phe Asn Asn Lys
        195                 200                 205

Asn Ser Gly Phe Trp His Ser Ser Leu Ile Asp Lys Asn Leu Ile Asp
        210                 215                 220

Tyr Phe Val Pro Phe Leu Pro Leu Glu Tyr Lys His Leu Lys Met Cys
225                 230                 235                 240

Ile Arg Val Glu Met Glu Ser Arg Gly Tyr Val Val Asp Glu Asp Ile
                245                 250                 255

Val Leu Arg Ile Ala Asp Glu Met Thr Phe Phe Pro Lys Glu Glu Lys
        260                 265                 270

Val Tyr Ser Asp Lys Gly Cys Lys Thr Val Tyr Thr Lys Leu Asp Tyr
            275                 280                 285

Tyr

<210> SEQ ID NO 16
<211> LENGTH: 293
<212> TYPE: PRT
<213> ORGANISM: Gallus gallus

<400> SEQUENCE: 16

Arg Leu Tyr Cys Tyr Phe Arg Glu Cys Cys Leu Gln Arg His Glu Gln
1               5                   10                  15

Arg Val Ala Ala Leu Gln Glu Ser Leu Asp Arg Arg Leu Phe Gly
            20                  25                  30

Gln His Leu Val Ser Lys Val Val Val Arg Ala Val Arg Gly Phe Leu
        35                  40                  45

Ser Asn Ala Gln Ala Lys Lys Pro Leu Ala Leu Ser Leu His Gly Trp
    50                  55                  60

Thr Gly Thr Gly Lys Asn Phe Val Ser Lys Ile Ile Ala Glu Ser Ile
65                  70                  75                  80

Tyr Lys Arg Gly Leu Lys Ser Asn Tyr Val His Gln Phe Val Ala Thr
                85                  90                  95

Leu His Phe Pro His Ala His Ser Ile Asn Leu Tyr Lys Asp Gln Leu
            100                 105                 110

Gln Ser Trp Ile Arg Gly Asn Val Ser Ile Cys Pro Arg Ser Ile Phe
        115                 120                 125

Ile Phe Asp Glu Met Asp Lys Met His Ala Gly Leu Ile Asp Ala Ile
130                 135                 140

Lys Pro Phe Leu Asp Tyr Tyr Glu Leu Leu Asp Gly Val Ser Tyr Arg
145                 150                 155                 160

Gln Ala Ile Phe Ile Phe Leu Ser Asn Ala Gly Ala Glu Lys Ile Thr
                165                 170                 175

Glu Val Ala Leu Asp Phe Trp Arg Asn Gly Lys Glu Arg Glu Asp Ile
            180                 185                 190

Gln Leu Thr Asp Met Gln Asn Ala Leu Ser Val Ser Val Phe Asn Asn
        195                 200                 205

Arg Asn Ser Gly Phe Trp His Ser Thr Leu Ile Asp Arg Asn Leu Ile
    210                 215                 220

Asp Tyr Phe Val Pro Phe Leu Pro Leu Glu Tyr Lys His Val Lys Met
225                 230                 235                 240

-continued

Cys Val Arg Val Glu Ile Glu Ser Arg Gly Tyr Ala Val Asp Glu Asp
            245                 250                 255

Ile Leu Thr Arg Val Ala Asp Glu Met Thr Tyr Phe Pro Arg Glu Glu
        260                 265                 270

Arg Ile Tyr Ser Asp Lys Gly Cys Lys Thr Val Asp Ala Lys Leu Asp
            275                 280                 285

Tyr Tyr Tyr Asp Leu
        290

<210> SEQ ID NO 17
<211> LENGTH: 290
<212> TYPE: PRT
<213> ORGANISM: Takifugu rubripes

<400> SEQUENCE: 17

Asn Ile Leu Tyr Tyr Phe Asn Glu Cys Cys Arg Pro Glu Trp Val Tyr
1               5                   10                  15

Phe Asn Arg Thr Gly Leu Glu Ala Asp Leu Glu Ser Lys Leu Phe Gly
            20                  25                  30

Gln His Ile Ala Ser Arg Ile Ile Leu Lys Ala Val Ser Gly Phe Met
        35                  40                  45

Ser Asn Glu Asn Pro Lys Lys Pro Leu Val Leu Ser Leu His Gly Trp
    50                  55                  60

Thr Gly Thr Gly Lys Asn Phe Val Ser Glu Leu Ile Ala Glu Asn Ile
65                  70                  75                  80

Phe Lys Glu Gly Met Asp Ser Lys Tyr Val His Val Phe Thr Ser Glu
                85                  90                  95

Leu His Phe Pro His Ser Ser Gln Ser Asp Thr Tyr Lys Thr Gln Leu
            100                 105                 110

Gln Gln Trp Ile Lys Gly Asn Val Ser Glu Cys Gly Arg Met Phe Ile
        115                 120                 125

Phe Asp Glu Met Asp Lys Met His Pro Gly Leu Ile Asp Ser Ile Lys
    130                 135                 140

Pro Tyr Leu Asp Tyr Tyr Asp Lys Leu Asp Gly Val Ser Tyr Arg Lys
145                 150                 155                 160

Ala Ile Phe Ile Phe Leu Ser Asn Ala Gly Gly Glu Ser Ile Val Asp
                165                 170                 175

Ile Ala Leu Asp Phe Trp Lys Ala Gly Arg Ser Arg Glu Glu Ile Lys
            180                 185                 190

Leu Arg Asp Leu Glu Thr Val Leu Ser Leu Ser Val Phe Asn Asn Lys
        195                 200                 205

Lys Ser Gly Leu Trp His Thr Ser Leu Ile Asp Lys Asn Leu Val Asp
    210                 215                 220

Phe Phe Val Pro Phe Leu Pro Leu Glu Tyr His His Val Val Gln Cys
225                 230                 235                 240

Ala Met Asn Glu Met Lys Val Arg Gly His Glu Pro Asp Leu Asn Val
                245                 250                 255

Ala Asp Glu Val Ala Arg Asp Leu Val Phe Phe Pro Lys Ser Glu Arg
            260                 265                 270

Val Phe Ala Val Lys Gly Cys Lys Thr Ile Gln Ser Lys Ser Leu Asp Tyr
        275                 280                 285

Tyr Thr
    290

<210> SEQ ID NO 18

```
<211> LENGTH: 291
<212> TYPE: PRT
<213> ORGANISM: Danio rerio

<400> SEQUENCE: 18

Asn Met Phe Tyr Tyr Phe Asn Glu Cys Cys Arg Pro Glu Trp Ile Ser
1               5                   10                  15

Tyr Asn Lys Thr Gly Leu Lys Tyr Asp Leu Asp Thr Lys Leu Tyr Gly
            20                  25                  30

Gln His Val Ala Gly Gln Val Ile Leu Lys Ala Val Thr Gly Phe Met
        35                  40                  45

Asn Asn Lys Lys Pro Lys Lys Pro Leu Val Leu Ser Leu His Gly Trp
    50                  55                  60

Thr Gly Thr Gly Lys Asn Phe Val Ser Gln Leu Leu Ala Glu Asn Ile
65                  70                  75                  80

Tyr Val Lys Gly Met Glu Ser Ser Phe Val His Leu Phe Thr Ala Thr
                85                  90                  95

Ala His Phe Pro His Glu Ile His Ile Asp Thr Tyr Lys Thr Gln Leu
            100                 105                 110

Gln Asp Trp Ile Arg Gly Asn Val Ser Ile Cys Pro Arg Ser Met Phe
        115                 120                 125

Ile Phe Asp Glu Met Asp Lys Met His Pro Gly Leu Ile Asp Ser Ile
130                 135                 140

Lys Pro Tyr Leu Asp Phe Tyr Asp Asn Leu Asn Gly Val Ser Tyr Arg
145                 150                 155                 160

Glu Ala Ile Phe Ile Phe Leu Ser Asn Ala Gly Gly Glu Asn Ile Val
                165                 170                 175

Gln Val Ala Leu Asp Phe Trp Lys Asp Gly Lys Glu Arg Glu Glu Ile
            180                 185                 190

Gln Leu Lys His Leu Glu Thr Ala Leu Ser Leu Ser Val Phe Asn Asn
        195                 200                 205

Lys Asn Ser Gly Phe Trp His Thr Ser Leu Ile Asp Lys Asn Leu Val
    210                 215                 220

Asp Phe Phe Val Pro Phe Leu Pro Leu Glu Tyr Lys His Ile Ile Gln
225                 230                 235                 240

Cys Gly Leu Ala Glu Met Ile Ala Lys Gly His Ser Pro Asp Lys Glu
                245                 250                 255

Val Val Glu Lys Met Ala His Asp Leu Asn Tyr Phe Pro Lys Glu Glu
            260                 265                 270

Arg Val Phe Ser Met Gln Gly Cys Lys Val Ile Pro Ser Arg Leu Asp
        275                 280                 285

Phe Tyr Ile
    290

<210> SEQ ID NO 19
<211> LENGTH: 294
<212> TYPE: PRT
<213> ORGANISM: Nematostella vectensis

<400> SEQUENCE: 19

Gly Leu Phe Cys Tyr Lys Thr Glu His Cys Thr Asp Gly Trp Ile Ser
1               5                   10                  15

Pro Asn Met Thr Gly Leu Lys Lys Ser Leu Asp Asn Arg Leu Phe Gly
            20                  25                  30

Gln His Leu Val Lys Asp Ile Val Tyr Lys Ala Val Lys Gly His Val
        35                  40                  45
```

```
Thr Asn Lys Ser Pro His Lys Ala Leu Ala Leu Ser Phe Asn Gly Trp
 50                  55                  60

Thr Gly Cys Gly Lys Asn Tyr Val Ser Lys Ile Ile Ala Glu His Leu
65                  70                  75                  80

Tyr Lys Lys Gly Ile Asp Ser Ser Tyr Val His Val Met Ile Ala Thr
                 85                  90                  95

His Asp Phe Pro His Lys Ser Met Val Glu Thr Tyr Lys Glu Gln Leu
            100                 105                 110

Lys Arg Trp Ile Val Gly Asn Val Thr Lys Cys Gly Arg Ser Met Phe
115                 120                 125

Ile Phe Asp Glu Met Asp Lys Met Pro Glu Gly Leu Val Gly Val Leu
130                 135                 140

Lys Pro Phe Leu Asp His Tyr Pro Asp Val Ala Gly Ile Asp Phe Arg
145                 150                 155                 160

Lys Cys Ile Phe Leu Phe Leu Ser Asn Thr Gly Ala His Ser Ile Asn
                165                 170                 175

Glu Glu Thr Leu Met Asn Trp Gln Arg Gly Arg Lys Arg Glu Asp Met
            180                 185                 190

Thr Ile Lys His Met Asp His Leu Ile Asn Leu Gly Ala Phe Asn Ser
        195                 200                 205

Asn Gly Gly Phe Trp His Thr Thr Leu Ile Glu Lys His Leu Ile Asp
210                 215                 220

Tyr Phe Val Pro Phe Leu Pro Leu Glu Arg Ala His Ile Lys Gln Cys
225                 230                 235                 240

Ala Leu Val Asp Leu Gln Asp Lys Gly Arg Lys Arg Glu Asp Ile Thr
                245                 250                 255

Asp Asp Leu Leu Asn Met Ile Ala Asp Glu Leu Leu Tyr Phe Pro Glu
            260                 265                 270

Gly Thr Arg Val Phe Ser Lys Ser Gly Cys Lys Lys Val Ser Ser Lys
        275                 280                 285

Val Asp Ile Ile Ile Gly
        290

<210> SEQ ID NO 20
<211> LENGTH: 302
<212> TYPE: PRT
<213> ORGANISM: Branchiostoma floridae

<400> SEQUENCE: 20

His Phe Lys Cys Asn Val Val Glu Cys Cys Asp Asn Asn Trp Phe Ile
1               5                   10                  15

Pro Asn Ile Thr Gly Leu Arg Thr Ser Leu Gln Asp Lys Leu His Gly
            20                  25                  30

Gln His Leu Val Val Asp Thr Val Ala Lys Ala Val Lys Gly His Ile
        35                  40                  45

Arg Asn Lys Asn Pro Ser Lys Ala Leu Val Leu Ser Phe His Gly Trp
 50                  55                  60

Thr Gly Gly Gly Lys Asn Phe Val Ser Lys Met Ile Ala Glu Asn Leu
65                  70                  75                  80

Phe Val Lys Gly Met Met Ser Arg His Val His Leu Phe Val Ala Thr
                85                  90                  95

Leu His Phe Pro His Lys Asp Arg Val Glu Thr Tyr Lys Asp Gln Leu
            100                 105                 110

Arg Glu Trp Ile Lys Gly Asn Thr Ser Asp Cys Pro His Ser Ile Phe
```

```
            115                 120                 125
Val Phe Asp Glu Met Asp Lys Leu Pro Glu Gly Leu Leu Asp Ala Val
130                 135                 140

Lys Pro Tyr Ile Asp His Tyr Thr Glu Ile Asn Gly Val Asp Tyr Arg
145                 150                 155                 160

Lys Thr Ile Phe Ile Leu Leu Ser Asn Thr Ala Gly Asn Thr Ile Thr
                165                 170                 175

Gln Arg Thr Tyr Gln His Trp Gln Glu Gly Arg Lys Arg Glu Asp Ile
            180                 185                 190

Ser Leu Lys Glu Met Asp Asp Leu Ile Leu Lys Gly Ser Phe Asn Glu
        195                 200                 205

Lys Gly Gly Leu Trp His Ser Ser Leu Ile Glu Lys Asn Leu Ile Asp
210                 215                 220

Val Phe Ile Pro Phe Leu Pro Leu Glu Arg Gln His Val Lys Leu Cys
225                 230                 235                 240

Ile Arg Asp Asp Leu Arg Ala Lys Gly His Thr Val Thr Glu Asp Val
                245                 250                 255

Val Thr Lys Val Ala Asp Glu Leu Gln Tyr Phe Pro Asp Arg Glu Gln
            260                 265                 270

Leu Tyr Ser Lys Ser Gly Cys Lys Arg Val Ser Gln Lys Val Asp Leu
        275                 280                 285

Ile Met Glu Glu Val Ser Gln Thr Val Glu Ile Met Arg
290                 295                 300

<210> SEQ ID NO 21
<211> LENGTH: 314
<212> TYPE: PRT
<213> ORGANISM: Strongylocentrotus purpuratus

<400> SEQUENCE: 21

Trp Cys Val Trp Glu Cys Cys Asp Glu Pro Trp Ile Asn Val Asn Asn
1               5                   10                  15

Ile Ser Ser Gly Leu Asp Asn Val Leu Asn Glu Asn Leu Phe Gly Gln
            20                  25                  30

His Ile Val Lys Glu Thr Val Ser Ala Ala Leu Gln Gly His Leu Leu
        35                  40                  45

Asn Pro Asn Pro Pro Lys Pro Leu Val Leu Ser Phe His Gly Arg Thr
    50                  55                  60

Gly Thr Gly Lys Asn Phe Val Ser Arg Met Ile Ala Glu Ser Ile Tyr
65                  70                  75                  80

Lys Glu Gly Leu Ser Ser Lys Tyr Val His Leu Lys Ile Ala Asp Arg
                85                  90                  95

Asp Phe Arg His Thr Thr Lys Phe Ala Glu Tyr Lys Glu Ser Leu His
            100                 105                 110

Asn Glu Val Phe Asn Ser Ala Lys Asn Cys Pro Arg Gln Leu Phe Ile
        115                 120                 125

Phe Asp Glu Val Glu Asn Met Pro Pro Gly Leu Leu Asp Thr Ile Arg
130                 135                 140

Pro Phe Leu Glu Tyr Arg Ser His Leu Glu Gly Val Gln Phe Asn Lys
145                 150                 155                 160

Ala Ile Phe Ile Phe Leu Ser Asn Thr Ala Ala Arg Glu Ile Ser Glu
                165                 170                 175

Tyr Ala Leu Ser His Met Gln Ala Gly Gly Thr Arg Glu Glu Ile Thr
            180                 185                 190
```

```
Leu Gln Ser Leu Glu Pro Leu Ile Glu Gln Ser Ser Phe Ser Ser Ala
            195                 200                 205

Gly Gly Gly Phe Gln Ser Ala Arg Leu Ile Asp Lys Tyr Leu Ile Ser
    210                 215                 220

His Phe Ile Pro Phe Leu Pro Leu Glu Thr Ser His Val Arg Asn Cys
225                 230                 235                 240

Ile Ile Ser Glu Leu Leu Ser His His Ala Arg Ser Asp Ala Ser Thr
                245                 250                 255

Ser Thr Arg Asp Ile Ala Asp Glu Val Ile Arg Glu Leu Gln Phe Trp
            260                 265                 270

Pro Lys Gly Ser Gly Leu Phe Ala Thr Lys Gly Cys Lys Ser Val Ala
    275                 280                 285

Glu Lys Leu Asn Leu Ala Leu Phe Arg Ala His Arg Arg Lys Glu Ala
290                 295                 300

Val Lys Gln Asp Leu Ser Lys Asn Glu Leu
305                 310

<210> SEQ ID NO 22
<211> LENGTH: 295
<212> TYPE: PRT
<213> ORGANISM: Ciona intestinalis

<400> SEQUENCE: 22

Ser Phe Arg Cys Lys Thr Asn Leu Met Glu Cys Cys Asp Lys His Asn
1               5                   10                  15

Ile Lys Pro Asn Met Thr Gly Leu Gln His Asp Leu Arg Thr Lys Leu
            20                  25                  30

Tyr Gly Gln His Leu Val Glu Lys Thr Val Tyr Arg Ala Val Lys His
        35                  40                  45

His Leu Ala Asn Pro Asn Pro Ser Lys Ala Leu Val Met Ser Phe His
    50                  55                  60

Gly Trp Thr Gly Ser Gly Lys Asn Tyr Val Ala Gln Met Ile Val Lys
65                  70                  75                  80

Asn Leu Tyr Arg Lys Asn Leu Glu Ser Ser Phe Val His Val Phe Asn
                85                  90                  95

Ala Glu Val Asp Phe Lys His Gln Gln Asn Val Gly Val Tyr Lys Asp
            100                 105                 110

Gln Leu Gln Ser Trp Leu His Gly Asn Val Ser Lys Cys Gly Arg Ser
        115                 120                 125

Ile Phe Ile Phe Asp Glu Ile Asp His Met Pro Val Gly Leu Val Asp
    130                 135                 140

Ala Leu Lys Pro Tyr Met Ser Asn Glu Pro Val Val His Gly Val Asp
145                 150                 155                 160

Tyr Arg Lys Thr Ile Phe Ile Phe Leu Ser Asn Thr Gly Gly Gln Glu
                165                 170                 175

Ile Asn Lys Lys Cys Tyr Glu Thr Trp Gln Leu Gly Asn Ser Arg Ser
            180                 185                 190

Gly Ile Lys Leu Ser Asp Met Glu Glu Met Leu Glu Gln Val Ala Phe
        195                 200                 205

Asn Glu Lys Ser Gly Leu Lys Asn Ser Gly Val Val Glu Arg Asn Leu
    210                 215                 220

Ile Asp His Phe Val Pro Phe Phe Pro Leu Gly Arg Glu His Val Glu
225                 230                 235                 240

Ser Cys Val Lys Asp Glu Val Arg Arg Leu Asn Ala Arg Lys Leu Thr
                245                 250                 255
```

```
Pro Ser Glu Met Gln Glu Ile Met Asp Glu Leu Gln Trp Met Pro Lys
            260                 265                 270

Thr Val Arg Leu Tyr Ser Lys Ser Gly Cys Lys Lys Ile Ala Gln Lys
        275                 280                 285

Val Gly Leu Val Val Leu Asp
        290                 295

<210> SEQ ID NO 23
<211> LENGTH: 309
<212> TYPE: PRT
<213> ORGANISM: Caenorhabditis elegans

<400> SEQUENCE: 23

Phe Leu Lys Cys Leu Phe Tyr Thr Cys Cys Gly Glu Thr Asp Ile Phe
1               5                   10                  15

Asn Tyr His Ala Leu Tyr Lys Asp Phe Asp Asn Lys Ile Phe Gly Gln
            20                  25                  30

His Leu Met Ala Glu Ser Val Val His Ser Ile Lys Ser His Trp His
        35                  40                  45

Asn Glu His Ser Gln Lys Pro Leu Val Leu Ser Phe His Gly Gly Thr
    50                  55                  60

Gly Thr Gly Lys Asn Tyr Val Thr Glu Ile Ile Val Asn Asn Thr Tyr
65                  70                  75                  80

Arg Ser Gly Met His Ser Pro Phe Val Asn Tyr Val Ala Thr Asn
                85                  90                  95

Asn Phe Pro Asn Lys Lys Tyr Ile Glu Asp Tyr Lys Leu Glu Leu Lys
            100                 105                 110

Asp Gln Leu Ile Arg Ser Ala Arg Arg Cys Gln Arg Ser Ile Phe Ile
        115                 120                 125

Phe Asp Glu Thr Asp Lys Leu Gln Ser Glu Leu Ile Gln Val Ile Lys
130                 135                 140

Pro Phe Leu Asp Tyr Tyr Pro Ala Val Phe Gly Val Asp Phe Arg Lys
145                 150                 155                 160

Thr Ile Phe Ile Phe Leu Ser Asn Lys Gly Ser Lys Glu Ile Ala Asn
                165                 170                 175

Ile Ala Leu Glu His His Glu Asn Gly Lys Ile Arg Ser Gln Leu Glu
            180                 185                 190

Leu Lys His Phe Glu Arg Thr Leu Met Leu Ser Ala Phe Asn Glu Glu
        195                 200                 205

Gly Gly Leu Arg Asn Thr Asp Met Ile Ser Asn Gln Leu Ile Asp His
    210                 215                 220

Phe Ile Pro Phe Leu Pro Leu Ser Lys Phe Tyr Val Ser Gln Cys Ile
225                 230                 235                 240

Gln Val His Leu Arg Lys Arg Gly Arg His Asp Leu Ala Lys Asp Gly
                245                 250                 255

Glu Phe Met Gln Arg Val Leu Asp Ser Leu Glu Phe Phe Pro Glu Ser
            260                 265                 270

Ser Lys Ile Phe Ser Ser Ser Gly Cys Lys Arg Val Asn Ala Lys Thr
        275                 280                 285

Asp Leu Glu Ile Ser Lys Met Gly Phe Ser Leu Asn Ser Lys Lys Glu
    290                 295                 300

Phe Asn Asp Glu Leu
305
```

```
<210> SEQ ID NO 24
<211> LENGTH: 305
<212> TYPE: PRT
<213> ORGANISM: Caenorhabditis elegans

<400> SEQUENCE: 24

Leu Phe Cys Thr Cys Cys Phe Glu Thr Asp Ile Phe Asp Tyr Leu Lys
1               5                   10                  15

Leu His Arg Asp Leu Ser Arg Phe Ile Tyr Gly Gln His Leu Val Ile
            20                  25                  30

Asp Thr Val Val Arg Ser Ile Lys Ser His Trp His Asn Glu His Pro
        35                  40                  45

Gln Lys Pro Leu Val Leu Ser Phe His Gly Gly Pro Gly Thr Gly Lys
    50                  55                  60

Asn Tyr Val Thr Glu Ile Ile Ala Lys Asn Thr Phe Arg Ser Gly Leu
65                  70                  75                  80

Gln Ser Pro Tyr Val Lys Tyr Phe Val Ala Thr Lys Asp Phe Pro Asn
                85                  90                  95

Asn Lys His Ile Glu Asp Tyr Lys Leu Lys Leu Lys Glu Gln Leu Ile
            100                 105                 110

Gln Ser Ala Asp Gly Cys Asp Arg Ser Ile Phe Val Phe Asp Glu Val
        115                 120                 125

Asp Lys Leu Gln Ser Glu Leu Val Gln Thr Ile Lys Pro Phe Leu Asp
    130                 135                 140

Phe Tyr Pro Ala Val Phe Glu Val Asp Phe Arg Lys Thr Thr Phe Ile
145                 150                 155                 160

Phe Leu Ser Asn Lys Gly Ser Ser Glu Ile Ala Asn Ile Ala Leu Glu
                165                 170                 175

His Arg Arg Asn Leu Lys Lys Arg Ser Gln Leu Glu Leu Lys His Phe
            180                 185                 190

Glu Arg Thr Leu Met Ser His Ala Phe Asn Glu Lys Gly Gly Leu Arg
        195                 200                 205

Asn Thr Glu Leu Ile Ser Asn Gln Leu Ile Asp His Tyr Ile Pro Phe
    210                 215                 220

Leu Pro Leu Ser Lys Phe Tyr Val Ser Gln Cys Ile Gln Val His Leu
225                 230                 235                 240

Arg Lys Arg Gly Arg His Asp Leu Ala Lys Asp Gly Glu Phe Met Gln
                245                 250                 255

Arg Val Leu Asp Ser Leu Glu Phe Phe Pro Glu Ser Ser Lys Val Phe
            260                 265                 270

Ser Ser Ser Gly Cys Lys Arg Val Asp Ala Lys Thr Glu Leu Glu Ile
        275                 280                 285

Ser Lys Met Gly Phe Ser Leu Asn Ser Glu Lys Glu Phe Asn Asp Glu
    290                 295                 300

Leu
305

<210> SEQ ID NO 25
<211> LENGTH: 309
<212> TYPE: PRT
<213> ORGANISM: Caenorhabditis elegans

<400> SEQUENCE: 25

Arg Leu Lys Cys Tyr Leu Tyr Glu Cys Cys His Glu Pro Asp Val Asn
1               5                   10                  15

Phe Asn Tyr His Thr Leu Asp Ala Asp Ile Ala Asn Leu Leu Phe Gly
```

```
                  20                  25                  30

Gln His Leu Val Lys Asp Val Val Asn Ser Ile Lys Ser His Trp
                     35                  40                  45

Tyr Asn Glu Asn Pro Arg Lys Pro Leu Val Leu Ser Phe His Gly Tyr
         50                  55                  60

Thr Gly Ser Gly Lys Asn Tyr Val Ala Glu Ile Ala Asn Asn Thr
         65                  70                  75                  80

Phe Arg Leu Gly Leu Arg Ser Thr Phe Val Gln His Ile Val Ala Thr
                             85                  90                  95

Asn Asp Phe Pro Asp Lys Asn Lys Leu Glu Glu Tyr Gln Val Glu Leu
                        100                 105                 110

Arg Asn Arg Ile Leu Thr Thr Val Gln Lys Cys Gln Arg Ser Ile Phe
                    115                 120                 125

Ile Phe Asp Glu Ala Asp Lys Leu Pro Glu Gln Leu Leu Gly Ala Ile
                130                 135                 140

Lys Pro Phe Leu Asp Tyr Tyr Ser Thr Ile Ser Gly Val Asp Phe Arg
        145                 150                 155                 160

Arg Ser Ile Phe Ile Leu Leu Ser Asn Lys Gly Gly Glu Ile Ala
                            165                 170                 175

Arg Ile Thr Lys Glu Gln Tyr Glu Ser Gly Tyr Pro Arg Glu Gln Leu
                        180                 185                 190

Arg Leu Glu Ala Phe Glu Arg Glu Leu Met Asn Phe Ser Tyr Asn Glu
                    195                 200                 205

Lys Gly Gly Leu Gln Met Ser Glu Leu Ile Ser Asn His Leu Ile Asp
                210                 215                 220

His Phe Val Pro Phe Leu Pro Leu Gln Arg Glu His Val Arg Ser Cys
        225                 230                 235                 240

Val Gly Ala Tyr Leu Arg Lys Arg Gly Arg Gly Asp Leu Val Ser Asn
                            245                 250                 255

Val Asp Phe Val Glu Arg Val Leu Asn Ser Leu Gln Tyr Phe Pro Glu
                        260                 265                 270

Ser Ser Lys Ala Phe Ser Ser Ser Gly Cys Lys Arg Val Asp Ala Lys
                    275                 280                 285

Thr Asp Leu Glu Met Ala Lys Ile Arg Pro Leu Leu Ser Ser Val His
                290                 295                 300

Phe Asp Asp Glu Leu
        305

<210> SEQ ID NO 26
<211> LENGTH: 294
<212> TYPE: PRT
<213> ORGANISM: Drosophila melanogaster

<400> SEQUENCE: 26

Tyr Cys Arg Phe Ala Glu Cys Cys Asp Asp Arg Asn Ile Pro Ala Arg
        1               5                  10                  15

Ile Asp Glu Leu Glu Arg Ser Leu Glu Arg Thr Leu Ile Gly Gln His
                            20                  25                  30

Ile Val Lys Gln His Ile Val Pro Ala Leu Lys Ala His Ile Ala Ser
                        35                  40                  45

Gly Asn Lys Ser Arg Lys Pro Leu Val Ile Ser Phe His Gly Gln Pro
                    50                  55                  60

Gly Thr Gly Lys Asn Phe Val Ser Glu Gln Ile Ala Asp Ala Leu Tyr
        65                  70                  75                  80
```

Leu Lys Gly Ser Arg Ser Asn Tyr Val Thr Lys Phe Leu Gly Gln Ala
            85                  90                  95

Asp Phe Pro Lys Glu Ser Glu Val Ser Asn Tyr Arg Val Lys Ile Asn
            100                 105                 110

Asn Ala Val Arg Asp Thr Leu Arg Ser Cys Pro Arg Ser Leu Phe Ile
            115                 120                 125

Phe Asp Glu Val Asp Lys Met Pro Ser Gly Val Phe Asp Gln Leu Thr
130                 135                 140

Ser Leu Val Asp Tyr Asn Ala Phe Val Asp Gly Thr Asp Asn Thr Lys
145                 150                 155                 160

Ala Ile Phe Ile Phe Leu Ser Asn Thr Ala Gly Ser His Ile Ala Ser
                    165                 170                 175

His Leu Gly Asn Val Met Lys Asn Gly Arg Leu Arg Glu Asp Thr Arg
            180                 185                 190

Leu Ser Asp Phe Glu Pro Leu Leu Arg Lys Ala Ala Tyr Asn Met Asp
            195                 200                 205

Gly Gly Met Lys Lys Thr Thr Met Ile Glu Ser His Val Ile Asp His
            210                 215                 220

Phe Ile Pro Phe Leu Pro Met Glu Lys Ala His Val Ile Lys Cys Leu
225                 230                 235                 240

Glu Ala Glu Leu Leu Arg Trp Arg Arg Asp Pro Lys Gln Ala Asn Asn
                    245                 250                 255

Gln Lys Ile Ile Glu Asp Ile Ile Asn Ser Ser Ile Ser Tyr Asp Arg
            260                 265                 270

Thr His Ser Leu Phe Ala Ile Ser Gly Cys Lys Thr Leu Glu Lys Lys
            275                 280                 285

Val Ala Met Ala Ile Tyr
            290

<210> SEQ ID NO 27
<211> LENGTH: 317
<212> TYPE: PRT
<213> ORGANISM: Trichoplax adhaerens

<400> SEQUENCE: 27

Tyr Cys Gln Phe Lys Glu Cys Asp Asn Ala Glu Trp Ala Ile His Asp
1               5                   10                  15

Pro Asn Ile Phe Lys Ala Lys Leu Thr Lys Glu Trp Lys Gln His Val
            20                  25                  30

Phe Gly Gln Asp Leu Ala Leu Lys Ile Ile Arg Asn Met Leu Thr Ser
            35                  40                  45

His Leu Val Arg Ile Ser Lys Lys Thr Ser Lys Ala Leu Val Leu
50                  55                  60

Ser Phe His Gly Gly Val Gly Thr Gly Lys Thr Leu Val Ala Lys Leu
65                  70                  75                  80

Leu Ala Lys Val Leu Tyr Lys Asn Gly Leu Ser Ser Tyr Val Arg
                    85                  90                  95

Arg Ile His Leu Lys Asp Phe Leu Thr Asn Leu Asn Met Asp Gly Lys
            100                 105                 110

Lys His Lys Leu Lys Thr Glu Ile Lys Arg Phe Val Gln Ser Cys Thr
            115                 120                 125

Arg Pro Leu Val Leu Phe Glu Glu Val Asp Lys Leu Glu Ala Gly Val
            130                 135                 140

Ile Asp Ala Leu Ser Pro Tyr Phe Asp Glu Ser Ser Val Asp Asn Val
145                 150                 155                 160

```
Ser Tyr Ala Asn Thr Ile Phe Ile Phe Thr Ser Asn Tyr Ala Ser Arg
                165                 170                 175

Glu Ile Asn Glu Glu Ala Cys Arg Gln Phe Thr Val Thr Thr Glu Val
            180                 185                 190

Asp Asp Phe Asp Ser Glu Asn Phe Tyr Asp Ile Ile Arg Lys Ile Ser
        195                 200                 205

Tyr Arg Gly Thr Ser Ala Asp Asp Ser Thr Ser Arg Thr Gly Phe Ala
    210                 215                 220

Ser Ser Glu Phe Val Lys His Cys Leu Val Ser Ser Phe Val Pro Phe
225                 230                 235                 240

Leu Pro Leu Asp Met Thr His Val Leu Gln Cys Ile Asp Ala Ser Leu
                245                 250                 255

Thr Arg Lys Leu Lys Asp His Glu Val Ser Thr Leu Asp Lys Pro Glu
            260                 265                 270

Arg Lys Asn Asp Leu Ile Lys Leu Ile Tyr Ser Gln Ile His Thr Val
        275                 280                 285

Asn Ala Asp Arg Cys Arg Lys Ser Phe Ser Glu His Gly Cys Lys Lys
    290                 295                 300

Val Gly Asp Ile Ala Asp Arg Glu Val Thr His Leu Met
305                 310                 315

<210> SEQ ID NO 28
<211> LENGTH: 254
<212> TYPE: PRT
<213> ORGANISM: Drosophila melanogaster

<400> SEQUENCE: 28

Asn Gln Tyr His Ser Ile Val His Asn Gln Asp Asn Tyr Cys Asn Pro
1               5                   10                  15

Ser Arg Arg Leu Gly Asp Met Val Leu His Ala Arg His Gln Val Leu
            20                  25                  30

Asn Gln Asp Leu Ala Leu Asn Gln Leu Glu Leu Ala Leu Asp Asn Thr
        35                  40                  45

Thr Asn Glu Ala Ile Val Leu Val Gly Thr Ser Gly Val Gly Lys Ser
    50                  55                  60

His Thr Ala Arg Ile Leu Arg Glu Thr Phe Pro Trp Pro Glu Asn Val
65                  70                  75                  80

Asn Thr Leu Ser Trp Thr Gly Ser Ser Ser Leu Gly Arg Val Lys Ser
                85                  90                  95

Met Leu Ser Gly Leu Thr Tyr Cys Gly Gln Asn Met Ile Leu Ile Asp
                100                 105                 110

Asn Met Thr Pro Lys Asp Ala His Phe Val Pro Ile Ile Asn Glu Met
            115                 120                 125

Ile Ser Glu Gly Glu Lys Ser Ala Asn His Thr Glu His Pro Gln Gln
        130                 135                 140

Lys Arg Leu Thr Ile Val Phe Ile Phe Asn Val Asn Ser Met Gln Pro
145                 150                 155                 160

Gly Glu Glu Phe Glu Met Asp Met Glu Ile Leu Arg Asn Met Pro His
                165                 170                 175

Thr Gln Leu Val Thr Phe Ala Thr Leu Asp Pro Thr His Leu Val Asp
                180                 185                 190

Cys Ile Arg Arg Glu Ala Ala Ile Ala Met Val His Leu Glu Asp Glu
        195                 200                 205

His Val Glu Glu Ile Ile Lys Ser Ile Asp Ala Ser Ala Ser Gly Cys
```

```
            210                 215                 220
Lys Ser Ile Leu Ala Lys Val Leu Leu Tyr Gly Lys Pro Ile Ile Ala
225                 230                 235                 240

Asp Ser Gln Asp Thr Asp Gln Val Leu Pro Val Gly Ser Phe
                245                 250
```

<210> SEQ ID NO 29
<211> LENGTH: 236
<212> TYPE: PRT
<213> ORGANISM: Drosophila melanogaster

<400> SEQUENCE: 29

```
Asp Leu Tyr Val His Asn Lys Asp Thr Phe Cys Ser Pro Glu Ala Leu
1               5                   10                  15

Asn Leu Glu Arg Ile Phe Arg Tyr Met Gly Arg Val Val Leu Asn Gln
            20                  25                  30

Glu Gln Ala Leu Ser Arg Met Glu Arg Ala Leu Ser Gly Ser Gly Arg
        35                  40                  45

Phe Arg Ser Val Ala Leu Leu Gly Pro Pro Gly Val Gly Lys Thr Leu
    50                  55                  60

Ala Thr Glu Thr Leu Arg Arg Cys Phe Pro Trp Pro Arg Asn Ala His
65                  70                  75                  80

Ser Tyr Ser Trp Ser Thr Gln Val Ser Asp Glu Ala Ser Lys Phe Arg
                85                  90                  95

Leu Ile Arg Gln Phe Ala Asp Gly Leu Ser Glu Cys Gly Val Asn Leu
            100                 105                 110

Leu Ile Ile Asp Asn Leu Thr Thr Cys Asp His Gly Leu Val Pro Ile
        115                 120                 125

Tyr Asn Arg Leu Ile Leu Glu Arg Glu Gly Glu Pro Lys Gly Asn Gln
    130                 135                 140

Arg Val Leu Val Val Tyr Val Phe Asn Leu Glu Thr Asn Leu Tyr Trp
145                 150                 155                 160

Glu Gln Phe Glu Leu Leu Gln Glu Leu Pro Ala Glu Thr Thr Ile Val
                165                 170                 175

Asn Phe Arg Phe Phe Asn Glu Asp Asp Leu Leu Asp Cys Leu Ala Ser
            180                 185                 190

Glu Leu Lys Arg Glu Arg Arg Ile Leu Thr Ser Lys Lys Glu Ser Phe
        195                 200                 205

Ile Leu Gln Glu Ala Met Lys Thr Val His Ser Ser Gly Cys Lys Ser
    210                 215                 220

Leu Arg Leu Leu Leu Leu Gln Asn Gly Thr Asp Ala
225                 230                 235
```

<210> SEQ ID NO 30
<211> LENGTH: 305
<212> TYPE: PRT
<213> ORGANISM: Homo sapiens

<400> SEQUENCE: 30

```
Ala Gln Arg Cys Leu Leu Leu Val Ala Ile Val Gly Phe Gln Val
1               5                   10                  15

Leu Asn Ala Ile Glu Asn Leu Asp Asp Asn Ala Gln Arg Tyr Asp Leu
            20                  25                  30

Asp Gly Leu Glu Lys Ala Leu Gln Arg Ala Val Phe Gly Gln Pro Ala
        35                  40                  45

Ala Val Ser Arg Ile Val Ala Leu Met Arg Asp Tyr Leu Ala Thr His
```

```
                50                  55                  60
Val His Ser Arg Pro Leu Leu Ala Leu His Gly Pro Ser Gly Val
 65                  70                  75                  80

Gly Lys Ser His Val Gly Arg Leu Leu Ala Arg His Phe Arg Ser Val
                 85                  90                  95

Leu Glu Asp Ser Ala Leu Val Leu Gln Tyr His Ala Arg His His Cys
                100                 105                 110

Pro Glu Ala Arg Ala Ala Gln Asp Cys Arg Glu Glu Leu Ala Arg Arg
                115                 120                 125

Val Ala Asp Val Val Ala Arg Ala Glu Ala Glu Lys Thr Pro Leu
130                 135                 140

Leu Val Leu Asp Asp Val Glu Leu Met Pro Arg Pro Leu Leu Asp Glu
145                 150                 155                 160

Leu His Gly Phe Leu Gln Pro Gln Arg Ser His His Phe His Asn Ala
                165                 170                 175

Ile Tyr Val Leu Leu Ser Gly Ala Gly Gly Ala Glu Val Thr Arg Phe
                180                 185                 190

Val Leu Gln Asn Ala Ser Arg Ala Leu Pro Leu Arg Pro Asp Gly Phe
                195                 200                 205

Arg Ser Ala Glu Ala Ala Ala Gln Ala Glu Glu Asp Leu Arg Ala
210                 215                 220

Ser Leu Leu Ala Val Leu Ser Arg Glu His Pro Leu Trp Gln Ala Ala
225                 230                 235                 240

Ala Ile Val Pro Phe Leu Leu Leu Asp Lys Arg Asp Val Val Ser Cys
                245                 250                 255

Phe Arg Asp Glu Met Ala Gly Glu Gly Phe Phe Pro Asp Gln Ala Arg
                260                 265                 270

Ala Glu Asn Leu Ala Ala Gln Leu Ser Phe Tyr Arg Val Ala Gly Arg
                275                 280                 285

Glu Phe Ala Val Thr Gly Cys Lys Gln Val Val Ala Thr Val Asn Leu
                290                 295                 300

Leu
305

<210> SEQ ID NO 31
<211> LENGTH: 230
<212> TYPE: PRT
<213> ORGANISM: Homo sapiens

<400> SEQUENCE: 31

Ser Pro Ala Gln Gln Val Pro Lys Asn Pro Ala Leu Glu Ala Phe Leu
 1               5                  10                  15

Ala Gln Phe Ser Gln Leu Glu Asp Lys Phe Pro Gly Ser Ser Phe
                20                  25                  30

Leu Trp Gln Arg Gly Arg Lys Phe Leu Gln Lys His Leu Asn Ala Ser
            35                  40                  45

Asn Pro Thr Glu Pro Ala Thr Ile Ile Phe Thr Ala Ala Arg Glu Gly
        50                  55                  60

Arg Glu Thr Leu Lys Cys Leu Ser His His Val Ala Asp Ala Tyr Thr
 65                  70                  75                  80

Ser Ser Gln Lys Val Ser Pro Ile Gln Ile Asp Gly Ala Gly Arg Thr
                85                  90                  95

Trp Gln Asp Ser Asp Thr Val Lys Leu Leu Val Asp Leu Glu Leu Ser
                100                 105                 110
```

```
Tyr Gly Phe Glu Asn Gly Gln Lys Ala Ala Val Val His Phe Glu
            115                 120                 125

Ser Phe Pro Ala Gly Ser Thr Leu Ile Phe Tyr Lys Tyr Cys Asp His
130                 135                 140

Glu Asn Ala Ala Phe Lys Asp Val Ala Leu Val Leu Thr Val Leu Leu
145                 150                 155                 160

Glu Glu Glu Thr Leu Glu Ala Ser Val Gly Pro Arg Glu Thr Glu Glu
                165                 170                 175

Lys Val Arg Asp Leu Leu Trp Ala Lys Phe Thr Asn Ser Asp Thr Pro
                180                 185                 190

Thr Ser Phe Asn His Met Asp Ser Asp Lys Leu Ser Gly Leu Trp Ser
                195                 200                 205

Arg Ile Ser His Leu Val Leu Pro Val Gln Pro Val Ser Ser Ile Glu
            210                 215                 220

Glu Gln Gly Cys Leu Phe
225                 230

<210> SEQ ID NO 32
<211> LENGTH: 228
<212> TYPE: PRT
<213> ORGANISM: Homo sapiens

<400> SEQUENCE: 32

Ser Thr Pro Glu Val Glu Thr Thr Ala Val Gln Glu Phe Gln Asn Gln
1               5                   10                  15

Met Asn Gln Leu Lys Asn Lys Tyr Gln Gly Gln Asp Glu Lys Leu Trp
                20                  25                  30

Lys Arg Ser Gln Thr Phe Leu Glu Lys His Leu Asn Ser Ser His Pro
            35                  40                  45

Arg Ser Gln Pro Ala Ile Leu Leu Leu Thr Ala Ala Arg Asp Ala Glu
        50                  55                  60

Glu Ala Leu Arg Cys Leu Ser Glu Gln Ile Ala Asp Ala Tyr Ser Ser
65                  70                  75                  80

Phe Arg Ser Val Arg Ala Ile Arg Ile Asp Gly Thr Asp Lys Ala Thr
                85                  90                  95

Gln Asp Ser Asp Thr Val Lys Leu Glu Val Asp Gln Glu Leu Ser Asn
            100                 105                 110

Gly Phe Lys Asn Gly Gln Asn Ala Ala Val Val His Arg Phe Glu Ser
        115                 120                 125

Phe Pro Ala Gly Ser Thr Leu Ile Phe Tyr Lys Tyr Cys Asp His Glu
130                 135                 140

Asn Ala Ala Phe Lys Asp Val Ala Leu Val Leu Thr Val Leu Leu Glu
145                 150                 155                 160

Glu Glu Thr Leu Gly Thr Ser Leu Gly Leu Lys Glu Val Glu Glu Lys
                165                 170                 175

Val Arg Asp Phe Leu Lys Val Lys Phe Thr Asn Ser Asn Thr Pro Asn
                180                 185                 190

Ser Tyr Asn His Met Asp Pro Asp Lys Leu Asn Gly Leu Trp Ser Arg
                195                 200                 205

Ile Ser His Leu Val Leu Pro Val Gln Pro Glu Asn Ala Leu Lys Arg
            210                 215                 220

Gly Ile Cys Leu
225

<210> SEQ ID NO 33
```

```
<211> LENGTH: 232
<212> TYPE: PRT
<213> ORGANISM: Gallus gallus

<400> SEQUENCE: 33

Ala Lys Ser Gln Pro Ala Pro Arg Asn Pro Thr Val Glu Ala Phe Leu
1               5                   10                  15

Ser Gln Phe Asn Gln Leu Gln Asp Arg Phe Pro Gly Gln Ser Pro Asp
            20                  25                  30

Leu Trp Leu Arg Ser Arg Lys Phe Leu Gln Lys His Leu Asn Ala Ser
        35                  40                  45

Arg His Thr Gln Pro Ala Ile Ile Ile Phe Thr Ala Ala Arg Lys Gly
50                  55                  60

Glu Arg Thr Leu Arg Cys Leu Ser Thr His Val Ala Asp Ser Tyr Ser
65                  70                  75                  80

Ala Ala Leu Arg Ala Ser Thr Ala His Ile Asp Gly Glu Asp Lys Ser
                85                  90                  95

Gly Leu Gln Ser Asp Gln Ala Lys Leu Glu Val Asp Ser Glu Leu Ser
            100                 105                 110

Ser Ala Phe Gln Ala Gly Asp Cys Ala Ala Val Ile His Arg Phe Glu
        115                 120                 125

Leu Leu Pro Ala Gly Ala Thr Leu Ile Phe Tyr Lys Tyr Cys Asp His
    130                 135                 140

Glu Ser Ala Ala Phe Lys Asp Val Ala Leu Leu Thr Val Leu Leu
145                 150                 155                 160

Glu Glu Glu Met Leu Glu Thr His Ile Arg Leu Gln Gln Val Glu Glu
                165                 170                 175

Arg Val Arg Asp Phe Leu Trp Ala Lys Phe Thr Ser Ala Ser Ala Pro
            180                 185                 190

Ser Ser Tyr Asp His Met Asp Ser Asp Lys Leu Ser Gly Leu Trp Ser
        195                 200                 205

Arg Ile Ser His Leu Val Leu Pro Ile His Pro Val Gln Asn Ile Glu
    210                 215                 220

Lys Gly Gly Cys His Thr Lys Pro
225                 230

<210> SEQ ID NO 34
<211> LENGTH: 230
<212> TYPE: PRT
<213> ORGANISM: Gallus gallus

<400> SEQUENCE: 34

Asp Ala Thr Leu Ser Ile Arg Asn Thr Gln Ile Leu Gln Ala Phe Arg
1               5                   10                  15

Thr Arg Met Lys Lys Leu Arg Asn Thr Tyr Gln Ser Gln Asp Pro Asn
            20                  25                  30

Leu Trp Lys Arg Thr His Val Phe Leu Glu Arg His Leu Asn Thr Ser
        35                  40                  45

His Leu His Leu Glu Pro Ala Ile Leu Leu Phe Thr Ala Gly Gln Glu
50                  55                  60

Ala Glu Lys Ala Leu Arg Cys Leu Ser Asp Glu Ile Ala Asn Ala Phe
65                  70                  75                  80

Ala Phe Ser Gln Asn Gly Thr Thr Ile Lys Ile Asn Gly Ala Asp Lys
                85                  90                  95

Ala Ile Leu Asp Ser Asp Val Val Lys Leu Glu Val Asp Glu Leu
            100                 105                 110
```

```
Ser Ser Gly Phe Arg Glu Gly Lys Val Ala Val His Arg Phe
    115                 120                 125

Glu Leu Leu Pro Ala Gly Ser Thr Leu Ile Phe Tyr Lys Tyr Cys Asp
130                 135                 140

His Glu Asn Ala Ala Phe Lys Asp Val Ala Leu Leu Leu Thr Val Leu
145                 150                 155                 160

Leu Asp Glu Gln Ser Leu Arg Arg Ser Leu Thr Leu Lys Glu Val Glu
                165                 170                 175

Glu Lys Val Arg Asp Phe Leu Trp Thr Lys Phe Thr Ser Ser Asp Ala
            180                 185                 190

Pro Ser Ser Phe Asn Ser Ile Asp Thr Asp Lys Leu Ser Gly Leu Trp
        195                 200                 205

Ser Arg Ile Ser His Leu Val Leu Pro Val Trp Pro Glu Lys Gly Leu
    210                 215                 220

Pro Ile Glu Gly Cys Thr
225                 230

<210> SEQ ID NO 35
<211> LENGTH: 219
<212> TYPE: PRT
<213> ORGANISM: Takifugu rubripes

<400> SEQUENCE: 35

Gln Gln Ile Asp Ile Phe Leu Arg Arg Met Glu Lys Leu Lys Ser Gln
1               5                   10                  15

Phe Pro Asn Gln Arg Pro Glu Leu Trp Thr Arg Ser Lys Ile His Leu
            20                  25                  30

Leu Lys His Leu Arg Thr Ala Gln Pro Thr Glu Pro Val Ser Leu Ile
        35                  40                  45

Leu Thr Ala Gly Val Lys Ala Glu Arg Thr Leu Ser Cys Leu Ala His
    50                  55                  60

Gly Leu Ala Ser Thr Phe Asn Ala Ser Val Leu His Ile Asp Gly Thr
65                  70                  75                  80

Ser Lys Ser His Gln Asp Ser Asp Gln Val Lys Leu Asp Ile Asp Ser
                85                  90                  95

Lys Leu Gln Val Ala Phe Glu Gly Asp Gln Pro Val Ala Ile Ile His
            100                 105                 110

Arg Phe Glu Glu Leu Pro Pro Gly Ser Thr Leu Ile Phe Tyr Arg Tyr
        115                 120                 125

Cys Asp His Glu Asn Ala Ala Tyr Lys Lys Thr Phe Leu Ile Phe Thr
    130                 135                 140

Val Leu Leu Ser Glu Glu Glu Ile Pro Val Gln Ser Arg Leu Ser
145                 150                 155                 160

Ala Val Glu Glu Met Val Asp His Leu Gln Lys Lys Phe Leu Thr
                165                 170                 175

Asp Ser His Pro Ile Ser Phe Asp Arg Met Asp Arg Asp Lys Tyr Gly
            180                 185                 190

Gly Leu Trp Ser Arg Ile Ser His Leu Ile Leu Pro Val Ala Ala Glu
        195                 200                 205

Arg Arg Thr Glu His Glu Gly Cys Pro Ala Thr
    210                 215

<210> SEQ ID NO 36
<211> LENGTH: 223
<212> TYPE: PRT
```

<213> ORGANISM: Takifugu rubripes

<400> SEQUENCE: 36

```
Pro Cys Arg Ala Pro Glu Leu Glu Thr Phe Ala Asp Gln Leu Ser Leu
1               5                   10                  15

Leu Gln Thr Gln Phe Pro His Gln Gln Pro Glu Leu Trp Arg Arg Ser
            20                  25                  30

Lys Ile His Leu Glu Lys His Leu Lys Thr Ala Gln Pro Thr Glu Pro
        35                  40                  45

Val Ser Leu Ile Phe Thr Ala Asp Leu Gly Ala Glu Gln Thr Leu Arg
    50                  55                  60

Cys Leu Ala Gln Gly Leu Ala Ala Ser Phe Ser Ala Leu Asn Gly
65                  70                  75                  80

Ser Leu Leu Tyr Ile Asp Gly Ala Asp Thr Ala Gly Met Asp Ser Asp
                85                  90                  95

Gln Val Lys Leu Asp Ile Asp Asn Gln Leu Arg Ala Ala Phe Glu Gly
            100                 105                 110

Asp Lys Pro Ala Ala Val Ile His Arg Leu Glu Glu Phe Pro Pro Gly
        115                 120                 125

Ser Thr Leu Ile Phe Tyr Arg Tyr Cys Asp His Glu His Ala Ala Tyr
    130                 135                 140

Lys Arg Val Phe Leu Leu Phe Thr Val Leu Leu Pro Gln Asp Val Leu
145                 150                 155                 160

Gly Asp Glu Lys Ser Leu Arg Glu Val Glu Glu Asn Val Gln Asp Tyr
                165                 170                 175

Leu Arg Glu Arg Leu Val Asp Ser Asn Asp Thr Val Ser Tyr Asn Gly
            180                 185                 190

Met Asp Gly Asp Lys Tyr Gly Gly Leu Trp Ser Arg Ile Ser His Leu
        195                 200                 205

Ile Leu Pro Val Val Leu Glu Lys Glu Val Glu Leu Arg Gly Cys
    210                 215                 220
```

<210> SEQ ID NO 37
<211> LENGTH: 236
<212> TYPE: PRT
<213> ORGANISM: Danio rerio

<400> SEQUENCE: 37

```
Thr Pro Asn Lys Ile Pro Lys Gln Leu Asp Met Val Glu Val Phe Asn
1               5                   10                  15

Gln Glu Met Glu Lys Leu Gln Ala Ser Phe Pro Ser Gln Arg Gln Glu
            20                  25                  30

Leu Trp Lys Arg Ser Leu Ile His Ile Arg Arg His Leu Lys Thr Glu
        35                  40                  45

His Pro Thr Glu Pro Val Ser Leu Ile Leu Thr Ser Gly His Arg Ala
    50                  55                  60

Glu Lys Thr Leu Gly Cys Leu Ala Gln Cys Leu Ala Gln Ala Phe Ser
65                  70                  75                  80

Thr Thr Arg Asn Ser Thr Phe Leu Ser Ile Asp Gly Lys Ala Lys Thr
                85                  90                  95

Ser Leu Asp Ser Asp Gln Val Lys Leu Asp Ile Asp Ser Glu Leu Thr
            100                 105                 110

Lys Ala Phe Glu Ser Glu Lys Phe Ala Ala Val Ile His Arg Phe Glu
        115                 120                 125

Glu Leu Pro Pro Gly Ser Thr Leu Ile Phe Tyr Arg Tyr Cys Asp His
```

```
                130                 135                 140
Glu Asn Ala Ala Phe Lys Asn Val Phe Leu Ala Phe Thr Val Met Leu
145                 150                 155                 160

Asp Ala Glu Ala Glu Val Pro Ser Asn Ile Asn Leu Gly Arg Ile Glu
                165                 170                 175

Glu Met Val Gln Asp His Val Lys Gln Lys Phe Val Ser Ser Asp Lys
            180                 185                 190

Ser Ala Val Phe Asn Gln Met Asp Val Asp Lys Leu Ser Gly Leu Trp
        195                 200                 205

Ser Arg Ile Ser His Leu Ile Leu Pro Val Val Ala Glu Lys Arg Ile
        210                 215                 220

Glu Gln Gln Gly Cys Gly Ala Cys Asp Lys Pro Phe
225                 230                 235

<210> SEQ ID NO 38
<211> LENGTH: 229
<212> TYPE: PRT
<213> ORGANISM: Danio rerio

<400> SEQUENCE: 38

Pro Gln Thr Asp Val Val His Ser Glu Thr Leu Lys Asn Phe Ala Val
1               5                   10                  15

Asp Leu Ala Gly Leu Gln Thr Val Phe Pro Ser Gln Arg Ser Glu Phe
            20                  25                  30

Trp Lys Arg Ser Gly Lys His Leu Lys Ser His Leu Gln Thr Val Lys
        35                  40                  45

Pro Thr Glu Pro Val Ser Val Ile Leu Thr Ala Gly Leu Arg Ala Glu
    50                  55                  60

Arg Thr Leu Gly Cys Leu Ala Arg Arg Leu Ala Thr Met Phe Ser Ala
65                  70                  75                  80

Phe His Asn Ala Ser Ile Leu Glu Ile Asn Gly Asn Ser Lys Ser Ala
                85                  90                  95

Leu Asp Ser Asp Gln Val Lys Leu Glu Ile Asp Glu Ala Leu Lys Lys
            100                 105                 110

Ala Phe Glu Gly Asp Lys Pro Ala Ala Val Val His Asn Phe Glu Glu
        115                 120                 125

Leu Pro Pro Gly Ser Thr Leu Ile Phe Tyr Arg Tyr Cys Asp His Glu
    130                 135                 140

Thr Ala Ala Tyr Lys Asn Val Phe Leu Val Phe Thr Val Lys Leu Ser
145                 150                 155                 160

Val Asp Glu Ile Asp Pro Ser Val Ser Leu Ser Gln Val Glu Glu Met
                165                 170                 175

Val Leu Asp His Val Lys Gln Lys Phe Ile Thr Ser Gly Lys Ser Thr
            180                 185                 190

Lys Phe Asn Gln Met Asp Leu Asp Lys Leu Ser Gly Leu Trp Ser Arg
        195                 200                 205

Ile Ser His Leu Val Leu Pro Val Ala Ala Glu Gly Asn Ile Glu Gln
        210                 215                 220

Glu Gly Cys Glu Val
225

<210> SEQ ID NO 39
<211> LENGTH: 232
<212> TYPE: PRT
<213> ORGANISM: Ornithorhynchus anatinus
```

<400> SEQUENCE: 39

```
Ser Gln Ala Gln Ser Leu Pro Asp Asn Pro Ala Leu Asn Ala Phe Leu
1               5                   10                  15

Ala Glu Phe Ser Leu Leu Lys His Lys Phe Pro Gly Gln Ser Ser Phe
            20                  25                  30

Leu Trp Gln Arg Gly Arg Lys Phe Leu Lys Lys His Leu Asn Thr Ser
        35                  40                  45

His Pro Thr Glu Pro Ala Thr Val Ile Leu Thr Ala Ala Trp Glu Gly
    50                  55                  60

Lys Glu Thr Leu Lys Cys Leu Ser His Asn Leu Ala Asp Ala Tyr Ser
65                  70                  75                  80

Ser Phe Met Asn Leu Pro Ala Ile Arg Ile Asp Gly Thr Lys Gln Ser
                85                  90                  95

Leu Lys Asp Ser Asp Asp Cys Lys Val Glu Val Asp Glu Lys Leu Ser
            100                 105                 110

Ser Gly Phe Arg Asn Gly Lys Lys Ala Ala Val Val His Arg Phe Glu
        115                 120                 125

Ser Leu Pro Ala Gly Ser Thr Leu Ile Phe Tyr Lys Tyr Cys Asp His
    130                 135                 140

Glu Asn Ala Ala Phe Lys Asp Val Ala Leu Val Leu Thr Val Leu Leu
145                 150                 155                 160

Glu Glu Glu Thr Leu Gly Met Ser Leu Ser Pro Arg Glu Val Glu Glu
                165                 170                 175

Lys Val Arg Asp Leu Leu Trp Asp Arg Phe Thr Asn Ser Asp Thr Pro
            180                 185                 190

Asn Ser Tyr Asn His Met Asp Ser Asp Lys Leu Ser Gly Leu Trp Ser
        195                 200                 205

Arg Ile Ser His Leu Val Leu Pro Val Gln Pro Val Lys Ile Ile Glu
    210                 215                 220

Glu Gln Gly Cys Ala Leu Glu Asn
225                 230
```

<210> SEQ ID NO 40
<211> LENGTH: 231
<212> TYPE: PRT
<213> ORGANISM: Ornithorhynchus anatinus

<400> SEQUENCE: 40

```
Pro Glu Ser Ser Leu Ser Gly Glu Ile Thr Ala Val Gln Arg Phe Gln
1               5                   10                  15

Phe Gln Met Lys Gln Leu Met Asn Lys Tyr Pro Ser Gln Asp Glu Lys
            20                  25                  30

Leu Trp Lys Arg Ser Gln Ile Phe Leu Glu Lys His Leu Asn Ser Ser
        35                  40                  45

His Pro Arg Leu Gln Pro Ala Ile Leu Leu Thr Ala Ala Arg Asp
    50                  55                  60

Ala Glu Glu Val Leu Arg Cys Leu Ser Glu Arg Ile Ala Asp Ala Tyr
65                  70                  75                  80

Ser Ser Phe Phe Ser Val Ser Ala Ile Arg Ile Asp Gly Ala Gly Lys
                85                  90                  95

Ala Ala Gln Asp Ser Asn Val Val Lys Met Glu Met Asp Ser Gln Leu
            100                 105                 110

Asn Asp Gly Phe Lys Asn Gly Lys Lys Ala Ala Val Val His Arg Phe
        115                 120                 125
```

```
Glu Ser Leu Pro Ala Gly Ser Thr Leu Ile Phe Tyr Lys Tyr Cys Asp
130                 135                 140

His Glu Asn Ala Ala Phe Lys Glu Val Ala Leu Val Leu Thr Val Leu
145                 150                 155                 160

Leu Glu Glu Glu Thr Leu Gly Thr Ser Pro Asp Leu Lys Glu Ile
                165                 170                 175

Glu Glu Lys Val Arg Asp Phe Leu Lys Val Lys Phe Thr Asn Ser Asp
                180                 185                 190

Thr Pro Asn Ser Tyr Asn His Met Asp Ser Asp Lys Leu Ser Gly Leu
                195                 200                 205

Trp Ser Arg Ile Ser His Leu Val Leu Pro Val Gln Pro Glu Asn Ala
210                 215                 220

Leu Lys Ser Gly Ser Cys Leu
225                 230

<210> SEQ ID NO 41
<211> LENGTH: 216
<212> TYPE: PRT
<213> ORGANISM: Strongylocentrotus purpuratus

<400> SEQUENCE: 41

Asn Gln Asn Val Gln Ser Asn Glu Arg Pro Val Ala Tyr Arg Leu Glu
1               5                   10                  15

Asn Leu Thr Thr Glu Leu Glu His Val Lys Ala Lys Tyr Gln Thr Leu
                20                  25                  30

Asp Asp Thr Phe Trp Asp Val Ile Val Gly Ser Ser Trp Gly His Ile
            35                  40                  45

Gln Gly Asn Gly Thr Ile Lys Gln Pro Val Val Leu Leu Val Gly
50                  55                  60

Gln Pro Lys Ser Ser Ile Leu Asp Val Val Ala Lys Asp Val Ala Arg
65                  70                  75                  80

Leu Tyr Ser Asn Val Phe Thr Met Arg Asp Asp Ser Ile Ile Asp Ile
                85                  90                  95

Asp Gly Gly Trp Gln Ala Met Lys Glu Ala Asp Gln Ala Lys Leu Asp
            100                 105                 110

Met Asp Asn Asp Leu Glu Asn Gly Phe Asn Asn Gly Arg Lys Val Val
        115                 120                 125

Leu Leu Arg Gln Phe Asp Lys Leu Pro Pro Cys Ser Ile Met Leu Phe
130                 135                 140

His Ser Tyr Cys Asp Asn Glu Asn Ala Pro His Lys Asp Ala Val Ile
145                 150                 155                 160

Ile Phe Thr Val Glu Leu Glu Thr Thr Val Ser Ser Ile Ala Gln Ser
                165                 170                 175

Ile Glu Glu Leu Val Gln Glu His Leu Gly Ser Ile Trp Ala Gln Cys
            180                 185                 190

Pro Glu Glu Leu Leu Gln Asp Lys Ile Met Ala Met His Ser Arg Val
        195                 200                 205

Ser Asn Asn Ile Ala Phe Val Lys
210                 215

<210> SEQ ID NO 42
<211> LENGTH: 212
<212> TYPE: PRT
<213> ORGANISM: Strongylocentrotus purpuratus

<400> SEQUENCE: 42
```

```
Arg Ser Asp Arg Phe Asp Val Leu Met Gln Glu Gln Asp Val Leu His
1               5                   10                  15

Gln Gln His Pro Ser Leu Asp Glu Ser Lys Leu Ser Ile Ile Ala Gly
            20                  25                  30

Ala Ser Phe Asp His Val Glu Glu His Arg Glu Leu Val Arg Pro Val
        35                  40                  45

Val Leu Leu Leu Val Gly Lys His Gly Gly Lys Thr Asp Ile Asn Asp
50                  55                  60

Val Ala Ser Asn Val Ala Lys Met Tyr Ala Lys Val Phe Ser Pro Glu
65                  70                  75                  80

His His Glu Asn Asp Ile Val Arg Ile Val Gly Ala Asp Leu Glu Lys
                85                  90                  95

Ser Ala Ser Asp Glu Val Lys Lys Glu Val His Gly Arg Ile Glu Glu
            100                 105                 110

Gly Phe Lys Asn Cys Ser Asn Val Val Leu Ile Thr Asp Val Asp Arg
        115                 120                 125

Leu Pro Pro Cys Ser Ala Ile Leu Phe His Ala Tyr Cys Asp Asn Asp
    130                 135                 140

Ser Ala Pro Tyr Lys Asp Ala Val Phe Ile Phe Thr Met Thr Leu Asn
145                 150                 155                 160

Thr Lys Leu Ala Glu Asp Thr Gln Ala Met Val Asp Glu Lys Ala Val
                165                 170                 175

Gln Ala Gln Leu Asn Glu Gly Trp Ser Gln Cys Pro Glu Glu Phe Thr
            180                 185                 190

Pro Ala Lys Met Val Ala Met His Ser Arg Ile Ala Asn Asn Ile Val
        195                 200                 205

Ile Ile Lys Lys
    210

<210> SEQ ID NO 43
<211> LENGTH: 218
<212> TYPE: PRT
<213> ORGANISM: Trichoplax adhaerens

<400> SEQUENCE: 43

Arg Lys Ala Ser Thr Leu Asn Glu Met Glu Ala Ile Ser Gln Ser Arg
1               5                   10                  15

Lys Leu Ile Gln Asp Leu Lys Asn His Phe Ser Ser Gln Thr Glu Asn
            20                  25                  30

Thr Trp Lys Lys Leu Ala Phe Leu Ala Phe Gly Ile Tyr Asn Thr Gly
        35                  40                  45

Leu Gln Arg Glu Lys Pro Leu Val Phe Thr Leu Ala His Arg Ser Asn
50                  55                  60

Ala Phe Lys Ser Ser Arg Cys Leu Ile Met Lys Leu Leu Asp Ala Ile
65                  70                  75                  80

Pro Lys Pro Phe Met Glu Leu Asn Val His Gly Glu Tyr Ser Arg Asn
                85                  90                  95

His Ala Leu Asp Glu Asn Leu Glu His Ser Phe Leu Lys Gln Leu Asn
            100                 105                 110

Lys Ala Leu Thr Thr Asn Thr Ile Pro Ile Thr Asn Lys Leu His Ala
        115                 120                 125

Leu Asn Pro Lys Leu Ala Arg Gln Phe Gln Ser Tyr Cys Asp Asn Asp
    130                 135                 140

Asp Ala Pro Phe Lys Gln Ala Val Ile Leu Phe His Val Ala Leu Asn
145                 150                 155                 160
```

-continued

```
Gly Thr Tyr Asp Asp Asn Leu Leu Ser Ser Asn Glu Ile Tyr Val Glu
                165                 170                 175

Lys Glu Val Thr Lys Val Leu Lys Asn Ser Trp Ser Pro Met Glu Glu
            180                 185                 190

Phe Ile Phe Asp Pro Leu Ser Ala Arg Ile Leu Gln Asn Ile Val Val
        195                 200                 205

Ile Asn Ser Glu Glu Asp Phe Gln Gly Cys
    210                 215

<210> SEQ ID NO 44
<211> LENGTH: 215
<212> TYPE: PRT
<213> ORGANISM: Branchiostoma floridae

<400> SEQUENCE: 44

Glu Thr Arg Leu Ala Gln Pro Pro Ala Ile Ile Thr Gly Asp His Glu
1               5                   10                  15

Ala Ser Ile Ser Val Leu Lys Lys Thr Phe Pro Ser Gln Ser Ala Arg
            20                  25                  30

Leu Trp Gln Val Ser Asp Phe Val Ile Ser Asn His Leu Gln Ala Gly
        35                  40                  45

Asp Pro Arg Gln Pro Ala Met Leu Ile Leu Ala Gly Leu Pro Gly Ser
    50                  55                  60

Asn Arg Thr Val Asn His Leu Ala Glu Gly Leu Ala Arg Ile Tyr Ser
65                  70                  75                  80

Glu Glu Pro Leu Val Ile Asn Ser Arg Gln Tyr Ser Arg Val Asp Pro
                85                  90                  95

Ala Arg Gly Lys Leu His Leu Asp Arg Ala Leu Asp Ser Ala Phe Arg
            100                 105                 110

Gly Gly Arg Arg Ala Ala Val Leu Thr Glu Leu Asp Thr Leu Pro Pro
        115                 120                 125

Leu Ala Ala Met Met Leu His Ser Tyr Cys Asp His Asp Asn Ala Gln
    130                 135                 140

Tyr Lys Asp Val Ala Tyr Phe Met Thr Leu Gln Leu Arg Glu Phe Val
145                 150                 155                 160

Asp Pro Gly Leu Thr Gly Ala Gln Gln Asp Arg Val Val Arg Glu His
                165                 170                 175

Leu Arg Glu Ala Trp Ala Glu Leu Gly Arg Glu Lys Arg Asp Pro Leu
            180                 185                 190

Ile Ser Arg Val Ala Thr Met Ile Val Leu Val Arg Gln Glu Asp Ser
        195                 200                 205

Phe Asp Val Ile Ser Tyr Val
    210                 215

<210> SEQ ID NO 45
<211> LENGTH: 206
<212> TYPE: PRT
<213> ORGANISM: Branchiostoma floridae

<400> SEQUENCE: 45

Asn Pro Ser His Asp Pro Ala Gln Gly Pro Ala Ile Lys Thr Pro
1               5                   10                  15

Asp Leu Tyr Lys Glu His Val Val Gly Ala Met Gly Arg Ala Leu Leu
            20                  25                  30

Tyr Pro Pro Ser Ile Ile Thr Gln Pro Ala Val Leu Leu Val Thr Ser
        35                  40                  45
```

```
Ala Pro Gly Thr His Asp Thr Ala Arg Cys Val Ala Ser His Val Ala
    50                  55                  60

Gln Gly Phe Asp Lys Lys Pro Thr Ile Ile His Gly Asp Gln Leu Arg
65                  70                  75                  80

Gly Leu Asp Ala Asp Glu Ala Lys Lys His Leu Asp Glu Val Leu His
                85                  90                  95

Ala Gly Phe Ser Gln Gly Gly Lys Ala Ala Leu Val Tyr Ser Leu Gln
            100                 105                 110

Asp Ile Pro Leu Gln Ala Asn Leu Ile Phe His Ser Tyr Cys Asp Asn
        115                 120                 125

Thr Asn Ala Pro Tyr Lys Glu Thr Ala Ile Ile Leu Val Leu Gln Leu
    130                 135                 140

Glu Lys Pro Ile Gln Met Asp Arg Ser Asn Ser Asp Val Glu Gly Glu
145                 150                 155                 160

Ala Met Asp Arg Leu Gln Arg His Leu Glu Arg Gly Gly Val Leu Asp
                165                 170                 175

Ile Asp Lys Val Gly Ala Leu Met Ser Arg Met Ala Gly Phe Val Leu
            180                 185                 190

Ile Val Asp Lys Ser Asp Asn Leu Pro Ala Ser Cys Ala Leu
        195                 200                 205

<210> SEQ ID NO 46
<211> LENGTH: 227
<212> TYPE: PRT
<213> ORGANISM: Nematostella vectensis

<400> SEQUENCE: 46

Val Asp Val Glu Ser Lys Asp Glu Arg Ser Cys Asp Asp Glu Asp Asn
1               5                   10                  15

Ser Ser Thr Glu Glu Glu Cys Val Asp Asp Lys Met Lys Asn Gln
            20                  25                  30

Ser Ser Thr Gln Lys Lys Thr Gly Val Thr Arg Lys Asn Lys Gln Ile
        35                  40                  45

Asp Thr Glu Asn Ser Ala Gln Leu Ser Lys Pro Lys Val Ser Phe Lys
    50                  55                  60

Leu Gly Thr His Pro Val Ala Asn Cys Leu Ala Leu Arg Leu Ala Asn
65                  70                  75                  80

Ile Leu Asp Pro Glu Thr His Ile Glu Asn Val Glu Thr Val Asn
                85                  90                  95

Gly Lys Asp Leu Gln Asn Ile Asp Gly Asp Ile Ala Lys Lys Leu
            100                 105                 110

Asp Glu Ser Leu His Gly Thr Phe Asp Lys Gly Arg Arg Ala Ala Val
        115                 120                 125

Val Lys His Leu Glu Leu Leu Pro Pro Ser Glu Asn Leu Phe Tyr
    130                 135                 140

Ala Tyr Cys Asp Asn Asp Asn Ala Arg Phe Lys His Ala Ala Ile Leu
145                 150                 155                 160

Phe Thr Val His Leu Gln Met Glu Pro His Ser Ser Leu Arg Pro Val
                165                 170                 175

Glu Ala Glu Gly Met Val Glu Lys Phe Leu Ser Asp Leu Val Trp Asn
            180                 185                 190

Lys Glu Pro Tyr Asp Arg Asp Ala Val Ala Ala Leu Leu Ser Arg Ile
        195                 200                 205

Ala Asp Thr Val Ala Leu Ile Ser Arg Glu Asp Glu Lys Val Tyr Ser
```

```
                210                 215                 220
His Cys Gly
225

<210> SEQ ID NO 47
<211> LENGTH: 227
<212> TYPE: PRT
<213> ORGANISM: Ciona intestinalis

<400> SEQUENCE: 47

Asp Ser His Ser Glu Lys Met Glu Lys Ser Asn Met Glu Ile Tyr Lys
1               5                   10                  15

Glu Lys Met Gln Ser Leu Gln Asn Glu Phe Pro Ser Gln Asn Asn Lys
            20                  25                  30

Leu Trp Lys Ile Val Arg Val Ala Met Gln Glu His His Asp Lys Lys
        35                  40                  45

Asp Asn Leu Gln Pro Ala Val Leu Met Leu Ala Ser Asn Ala Asp Ala
    50                  55                  60

Asn Pro Thr Met Gln Cys Leu Ala Ser Lys Leu Ala Asp Ile Tyr Ser
65                  70                  75                  80

His Asn Cys Ser Gln Pro Lys Phe Val Val Pro Glu Asn Glu Phe Lys
                85                  90                  95

His Leu Ser Pro Glu Ser Ala Lys Val Leu Leu Asp Asn Lys Ile Ser
            100                 105                 110

Ser Gln Phe Gln Ala Gly Ser Cys Ala Ser Val Val Arg His Phe Glu
        115                 120                 125

Leu Ile Pro Pro Ala Ala Thr Lys Val Phe Tyr Gln Phe Cys Glu Asn
    130                 135                 140

Asp Asn Ala Pro Tyr Lys Asn Val Ala Val Ile Leu Thr Leu Gln Val
145                 150                 155                 160

Glu Pro Gly Asp Trp Ser Met Pro Tyr Pro Asn Leu Asp Asn Leu Pro
                165                 170                 175

Pro Lys Phe Trp Asp Arg Val Val Asp Gly Phe Leu Thr His Thr Leu
            180                 185                 190

Ala Thr Gly Asp Pro Val Val Met Thr Thr Asp Met Ile Gly Ala Leu
        195                 200                 205

Leu Ser Arg Ile Thr Pro Ser Val Val Trp Val Arg Arg Glu Asn Asp
    210                 215                 220

Leu His Cys
225

<210> SEQ ID NO 48
<211> LENGTH: 184
<212> TYPE: PRT
<213> ORGANISM: Drosophila melanogaster

<400> SEQUENCE: 48

Glu Glu Lys Gln Cys Asp Phe Lys Asp Leu Arg Thr Lys Tyr Pro Gln
1               5                   10                  15

Gln Gln Glu Lys Val Trp Arg Ala Leu Gln Lys Gly Ile Glu Gly Leu
            20                  25                  30

Ile Asn Lys Asp Lys His Pro Ser Val Phe Leu Phe Leu His Gln
        35                  40                  45

Asp Pro Lys Leu Glu Lys Leu Ile Asp Glu Ile Ala Ile Glu Ala Ser
    50                  55                  60

Met Cys Phe Gly Gly Pro Arg Lys Leu Ile His Met Lys Lys Glu His
```

```
            65                  70                  75                  80
Met Lys Glu Tyr Gly Leu Ala Ile Glu Gln Phe Lys Ser Lys Ile Asn
                85                  90                  95

Asp Gly Lys Val Phe Leu Ile Val Asn Leu Asn Glu Ile Ala Pro Asn
            100                 105                 110

Gly Ala Arg Ala Leu His Thr Ile Cys Asp Thr Tyr Ser Pro Leu Val
            115                 120                 125

Glu Asp Ala Val Ile Phe Leu Ser Leu Arg Thr Phe Asn Thr Thr Ala
            130                 135                 140

Val Asn Asn Ser Val Asn Leu Ala Thr Asp Thr Leu Tyr Asp Leu Trp
145                 150                 155                 160

Asp Gln Glu Leu Gly Asp His Glu Leu Asp Pro Leu Ile Thr Arg Val
            165                 170                 175

Thr Asp Gln Val Leu His Leu Ser
            180
```

<210> SEQ ID NO 49
<211> LENGTH: 208
<212> TYPE: PRT
<213> ORGANISM: Caenorhabditis elegans

<400> SEQUENCE: 49

```
Lys Gly Ser Lys Val Thr Thr Asn Glu Ser Tyr Glu Ser Tyr Ile Lys
1               5                   10                  15

Ser Val Arg Ser Val Ile Lys Asn Glu Phe Pro Thr Ile Ser Lys Glu
            20                  25                  30

Asn Arg Asp Leu Leu Arg Leu Ile Gly Gln Lys Ile Tyr Leu Glu Pro
            35                  40                  45

Glu Asn His Ala Pro Leu Val Val Leu Gly Gly Thr Pro Ala Lys
        50                  55                  60

Gln Ile Ala Glu Ala Val Asn Arg Ala Val Gln Asp Ala Lys Ser Asp
65                  70                  75                  80

Glu His Thr Thr Ala Gly Lys Ser Ser Ile Arg Val Glu Ser Asp Thr
                85                  90                  95

Asp Arg Ala Glu Leu His Ala Asn Leu Gln Glu Ile Leu Gly Pro Ala
            100                 105                 110

Leu Ile Ser Gln Ser Ser Pro Arg Thr Ala Val Ile Leu Asp Val Asp
            115                 120                 125

Leu Leu Lys Trp Asp Ala Val Leu Val Leu His Ala Phe Ser Asp His
130                 135                 140

Gly Lys Tyr Pro Val Pro Lys Thr Ile Leu Phe Leu Thr Val Ser Ser
145                 150                 155                 160

Gln Gln Asp Ser Thr Met Asp Ile Ala Asn Thr Ser Cys Asp Glu Lys
                165                 170                 175

Met Val Gln Phe Leu Thr Lys Arg Trp Ile Glu Asn Gly Gly Ser Ser
            180                 185                 190

Asp Asn Ile Pro Pro Ile Ile Ala Arg Ile Ser Tyr Phe Leu Cys Val
            195                 200                 205
```

<210> SEQ ID NO 50
<211> LENGTH: 199
<212> TYPE: PRT
<213> ORGANISM: Caenorhabditis elegans

<400> SEQUENCE: 50

```
Gln Asn Glu Pro Asn Gln Asp Arg Asn Pro Tyr Gln Asn Tyr Ile Glu
```

-continued

```
1               5                    10                   15
Ser Val Arg Ser Phe Val Asn Ser Asp Phe Ser Asp Ile Ser Lys Glu
            20                  25                  30

Asn Arg Asn Leu Leu Arg Leu Ile Gly Glu Gln Met Phe Leu His Pro
        35                  40                  45

Asp Glu His Ala Pro Leu Val Ile Val Ile Ala Gly Leu Lys Ala Asn
    50                  55                  60

Glu Phe Ser Glu Lys Leu Asn Lys Ala Ile Gln Asn Ser Lys Ser Glu
65                  70                  75                  80

Thr Asn Ser Asn Asn Leu Pro Ile Glu Ile Gly Asn Gln Leu Glu Arg
            85                  90                  95

Gly Glu Leu His Ala Ile Leu Asn Asn Ala Leu Ala Ser Gln Met Thr
                100                 105                 110

Pro Arg Thr Ala Val Leu Thr Asn Ile Asp Leu Leu Ala Trp Asp Ala
            115                 120                 125

Val Leu Val Leu His Ala Phe Ala Asp His Gly Thr Phe Pro Ile Pro
            130                 135                 140

Lys Thr Val Leu Leu Leu Ala Val Ser Thr Glu Glu Thr Thr Tyr Ser
145                 150                 155                 160

Gly Asn Ser Cys Asp Gly Lys Ile Leu Lys Leu Val Thr Asn Arg Trp
                165                 170                 175

Ile Glu Asn Gly Gly Asn Tyr Asp Asn Ile Pro Pro Ile Val Ala Arg
            180                 185                 190

Ile Ser Tyr Phe Met Cys Leu
            195
```

CRYSTAL STRUCTURES OF HUMAN TORSIN-A AND METHODS OF DETERMINING AND USING THE SAME

CROSS-REFERENCE TO RELATED PATENT APPLICATIONS

This application claims priority to U.S. Provisional Application Ser. No. 62/299,699, filed on 25 Feb. 2016, entitled "CRYSTAL STRUCTURES OF HUMAN TORSIN A AND ITS DYSTONIA MUTANT", and U.S. Provisional Application Ser. No. 62/330,683, filed on 2 May 2016, entitled "CRYSTAL STRUCTURES OF HUMAN TORSIN A AND ITS DYSTONIA MUTANT" the entire contents of which are incorporated herein by reference in its entirety and for all purposes.

STATEMENT OF FEDERALLY-SPONSORED RESEARCH

This invention was made with government support under Grant No. RO1 AR065484 awarded by the National Institutes of Health. The government has certain rights in the invention.

INCORPORATION BY REFERENCE

In compliance with 37 C.F.R. §1.52(e)(5), the sequence information contained in electronic file name: 1515028_103US2_Sequence_Listing_24FEB2017_ST25.txt; size 22.5 KB; created on: 24 Feb. 2017; using Patent-In 3.5, and Checker 4.4.0 is hereby incorporated herein by reference in its entirety.

BACKGROUND

1. Field of the Discovery

The present invention relates generally to a method of obtaining three dimensional structures of TorsinA, and more particularly to obtaining three dimensional structures of TorsinA via a protein composition, and applications of the same.

2. Background Information

Early-onset torsion dystonia (DYT1) is a genetic disease affecting an estimated 50,000 patients in the United States alone (Steeves et al., 2012). It is an incurable and severely debilitating neuromuscular disease (Breakefield et al., 2008). A single glutamate deletion at position 302 or 303 (ΔE) of the protein TorsinA is the primary cause for DYT1 (Ozelius et al., 1997).

TorsinA is a member of the ATPases Associated with diverse cellular Activities (AAA+) protein family. TorsinA resides in the endoplasmic reticulum of the cell, including the perinuclear space. The function of the protein is unclear, but it presumably acts in protein or membrane remodeling. It has been shown that TorsinA is activated by lamina-associated protein 1 (LAP1) and by luminal domain-like LAP1 (LULL1) (Sosa et al., 2014).

A glutamate deletion (ΔE) at position 302/303 of TorsinA is the most common cause of early onset primary dystonia, a neuromuscular disease. TorsinAΔE weakens the binding of the activators LAP1/LULL1, which likely represents the molecular basis for the disease. If binding to the activator can be restored, for example by a small molecule, this might well represent the drug needed to cure the disease. Conceptually, this is similar to the action of Vertex' Kalydeco drug for cystic fibrosis patients, which also partially restores the function of a protein. Human TorsinA is an extremely difficult protein to handle in vitro, and can barely be produced recombinantly.

Therefore, a heretofore unaddressed need exists in the art to address the aforementioned deficiencies and inadequacies.

SUMMARY

The present description provides compositions and methods relating to the surprising and unexpected discovery that a protein complex can be created for an unstable protein thereby allowing the structure to be resolved. The crystallized protein complex can be utilized, e.g., to screen potential therapeutics. Thus, in one aspect, the description provides a protein composition comprising, consisting essentially of or consisting of a target protein or portion thereof, a modulator of the target protein or portion thereof, and a binding protein or portion thereof, e.g., an antibody, nanobody or antigen binding fragment thereof that specifically binds to the target protein, the modulator or a combination thereof. In certain embodiments, at least one of the target protein, the modulator or both is a truncated protein, a deletion mutant or both. In one embodiment, the modulator of the target protein is an activator of the target protein.

In certain embodiments, the protein composition comprises a recombinantly produced fusion protein. In additional embodiments, the fusion protein comprises a target protein, and a modulator of the target protein in a contiguous polypeptide chain. In certain embodiments, at least one component of the fusion protein, e.g., at least one of the target protein, the modulator or both, is a truncated protein, deletion mutant or both. In one embodiment, the modulator of the target protein is an activator of the target protein.

In certain embodiments, the target protein is at least one of TorsinA, a mutant of TorsinA, including a substitution, deletion or truncation mutant, or combination thereof.

In certain embodiments, the target protein comprises the amino acid sequence set forth in the SEQ ID NO: 1-3 (SEQ ID NO: 1 is human TorsinA 51-332, SEQ ID NO: 2 is human TorsinA 51-332 with E171Q, SEQ ID NO: 3 is human TorsinA 51-332 with E171Q and ΔE303) or portion thereof.

In certain embodiments, the modulator is LULL1 or portions thereof.

In certain embodiments, the modulator comprises the amino acid sequence set forth in the SEQ ID NO: 4 (SEQ ID NO: 4 is LULL1 233-470) or portion thereof.

In another aspect, the description provides a method of creating a binding protein, antibody, nanobody or antigen binding fragment thereof capable of binding specifically to a protein composition as described herein. In certain embodiments, the binding protein, antibody, nanobody or antigen binding fragment thereof is obtained by immunizing a host with at least one of the target protein, modulator, a fusion protein comprising the same or combination thereof. In certain embodiments, the nanobody is obtained by immunizing a host with at least one protein having the amino acid sequence of SEQ ID NO: 1-4 or portion thereof, including combinations and fusion proteins comprising the same. In certain embodiments, the nanobody is obtained by immunization of a mammal, for example, an alpaca such as Lama pacos.

In certain embodiments, the target protein comprises an amino acid sequence set forth in at least one of SEQ ID NO: 1-3 or portion thereof, the modulator comprises the amino acid sequence set forth in the SEQ ID NO: 4 or portion thereof. In certain aspects, the nanobody comprises or is the amino acid sequence set forth in the SEQ ID NO: 5 or portion thereof, wherein the protein composition is co-expressed and optionally purified together.

In a further aspect, the description provides a kit comprising a first vector and a second vector. In certain embodiments, a first nucleotide sequence encoding the target protein and a second nucleotide sequence encoding the modulator are cloned into the first vector, and a third nucleotide sequence encoding the nanobody is cloned into the second vector, and the vectors comprise promoter sequences operably linked to the nucleotide sequence.

In certain embodiments, the first vector and the second vector are used to transform bacteria. In certain embodiments, the vectors are configured for eukaryotic transfection and/or expression.

In certain embodiments, the first nucleotide sequence comprises the nucleic acid sequence set forth in the SEQ ID NO: 6 (encoding the protein SEQ ID NO: 1) or portion thereof, or the nucleic acid sequence set forth in the SEQ ID NO: 7 (encoding the protein SEQ ID NO: 2) or a portion thereof, or the nucleotide sequence as set forth in the SEQ ID NO: 8 (encoding the protein SEQ ID NO: 3) or a portion thereof, and the second nucleotide sequence comprises the nucleic acid sequence set forth in the SEQ ID NO:9 (encoding the protein SEQ ID NO: 4) or portion thereof. In certain embodiments, the third nucleotide sequence comprises the nucleic acid sequence as set forth in SEQ ID NO: 10 (encoding the protein of SEQ ID NO: 5).

In certain embodiments, the first vector is a modified ampicillin resistant pETDuet-1 vector, the second vector is a pET-30b(+) vector, and the bacteria is *E. coli* strain LOBSTR(DE3) RIL.

In certain embodiments, the target protein comprises at least one amino acid sequence as set forth in the SEQ ID NO: 1-3, the modulator comprises the amino acid sequence set forth in the SEQ ID NO: 4, and the protein composition is crystallized to obtain crystals of space group P2$_1$2$_1$2$_1$ with approximate a=75.7 Å, b=90.7 Å, and c=105.1 Å such that the three dimensional structure of the crystallized protein composition can be determined to a resolution of about 1.4 Å or better (TorsinA 51-332/E171Q).

In another aspect, the description provides methods of obtaining crystals of a protein composition as described herein. In certain embodiments, the protein composition is crystallized to obtain crystals according to the following steps: preparing the protein composition as described herein; adding about 2 mM ATP to the prepared protein composition to form a protein stock; preparing a mother liquor comprising about 13% (w/v) polyethylene glycol (PEG) 6000, about 5% (v/v) 2-methyl-2,4-pentanediol, and about 0.1M MES pH6.5; mixing approximately 1 µl of the protein stock with 1 µl of the mother liquor to form a first mixture; and inducing crystallization of the protein composition in the first mixture by hanging drop/vapor diffusion under 18° C., wherein crystals are obtained in about 3-5 days.

In certain embodiments, the ATP added to the prepared protein composition is in a range of about 0.5-5 mM, the mother liquor comprises about 9-17% (w/v) polyethylene glycol (PEG) 6000, about 1-10% (v/v) 2-methyl-2,4-pentanediol, and about 0.05-0.2 M MES pH6.5. In certain embodiments, the protein stock solution and the mother liquor are mixed in approximately equal amount in a range of 0.1 µl to 5 µl. In certain embodiments, the crystallization may be induced by having drop or sitting drop vapor diffusion, liquid-liquid diffusion. In certain embodiments, crystals are obtained in about 1-14 days.

In certain embodiments the crystal is purified to about 4-4.5 mg/ml. In certain embodiments, the obtained crystals are cryoprotected by flash-frozen in liquid nitrogen after soaking in the mother liquor supplemented with about 20% (v/v) glycerol. X-ray data are collected using one of the obtained crystals, and the structure of the crystallized protein composition is determined based on the collected x-ray data.

In certain embodiments, the target protein comprises the amino acid sequence set forth in the SEQ ID NO: 2 or portion thereof, the modulator comprises the amino acid sequence set forth in the SEQ ID NO: 3 or portion thereof, and the protein composition is crystallized to obtain crystals of space group P2$_1$2$_1$2$_1$ with approximate a=75.5 Å, b=88.1 Å, and c=105.4 Å such that the three dimensional structure of the crystallized protein composition can be determined to a resolution of about 1.4 Å or better (TorsinA 51-332/E171Q/ΔE303 mutant structure).

In certain embodiments, the protein composition is crystallized to obtain crystals according to following steps: preparing the protein composition as described herein at about 4-4.5 mg/ml; adding about 2 mM ATP to the prepared protein composition to form a protein stock; preparing a mother liquor comprising about 19% (w/v) polyethylene glycol (PEG) 3350, about 0.2M AMSO$_4$, and about 0.1M Bis-Tris-HCl pH6.5; mixing approximately 1 µl of the protein stock with 1 µl of the mother liquor to form a second mixture; and inducing crystallization of the protein composition in the second mixture by hanging drop/vapor diffusion under about 18° C., wherein crystals are obtained in about 3-5 days.

In certain embodiments, the ATP added to the prepared protein composition is in a range of about 0.5-5 mM, the mother liquor comprises about 14-24% (w/v) polyethylene glycol (PEG) 3350, about 0.05-0.5 M AMSO$_4$, and about 0.05-0.2 M Bis-Tris-HCl pH 6.5. In certain embodiments, the protein stock solution and the mother liquor are mixed in approximately equal amount in a range of 0.1 µl to 5 µl. In certain embodiments, the crystallization may be induced by haing drop or sitting drop vapor diffusion, liquid-liquid diffusion. In certain embodiments, crystals are obtained in about 1-14 days.

In certain embodiments, the obtained crystals are cryoprotected by flash-frozen in liquid nitrogen after soaking in the mother liquor supplemented with about 20% (v/v) glycerol, x-ray data are collected using one of the obtained crystals, and the structure of the crystallized protein composition is determined based on the collected x-ray data.

In another aspect, the present invention relates to a method of determining the three dimensional structure of a crystallized protein composition as described herein to a resolution of about 1.4 Å or better; the method comprising the steps of: providing a first nucleotide sequence comprising the nucleic acid sequence set forth in at least one of SEQ ID NO: 6-8 (encoding the proteins SEQ ID NO: 1-3, respectively), a second nucleotide sequence comprising the nucleic acid sequence set forth in the SEQ ID NO: 9 (encoding the protein SEQ ID NO: 4) or a portion thereof, and a third nucleotide sequence comprising the nucleic acid sequence set forth in the SEQ ID NO: 10 (encoding the protein SEQ ID NO: 5) or portion thereof; cloning the first nucleotide sequence and the second nucleotide sequence to a first vector; cloning the third nucleotide sequence to a second vector; transforming and growing bacteria using the first vector and the second vector, wherein the bacteria expresses the three nucleotide sequences producing a first protein, a second protein and a third protein, and wherein the three proteins form a complex; purifying a protein complex to obtain a protein composition; crystallizing the protein composition to obtain crystals; collecting x-ray data using one of the obtained crystals; and determining the three dimensional structure from the collected x-ray data.

In certain embodiments, the protein composition comprises the amino acid sequence set forth in at least one of SEQ ID NO: 1-3 or portion thereof, and the protein composition is crystallized to obtain crystals of space group $P2_12_12_1$ with approximate a=75.7 Å, b=90.7 Å, and c=105.1 Å such that the three dimensional structure of the crystallized protein composition can be determined to a resolution of about 1.4 Å or better (TorsinA 51-332/E171Q).

In certain embodiments, the protein composition comprises the amino acid sequence set forth in the SEQ ID NO: 2 or 3 or portion thereof, and the protein composition is crystallized to obtain crystals of space group $P2_12_12_1$ with approximate a=75.5 Å, b=88.1 Å, and c=105.4 Å such that the three dimensional structure of the crystallized protein composition can be determined to a resolution of about 1.4 Å or better (TorsinA 51-332/E171Q/ΔE303 mutant structure).

In an additional aspect, the description provides vectors, e.g., cloning and/or expression vectors, e.g., suitable for expression in a eukaryotic or prokaryotic cell, comprising a nucleotide sequence that encodes at least one component of a protein composition described herein. In certain embodiments, the description provides a vector comprising a first nucleotide sequence encoding a target protein and a second nucleotide sequence encoding the modulator operably linked to a promoter sequence. In certain embodiments, the description provides a vector comprising a third nucleotide sequence encoding a nanobody protein operably linked to a promoter sequence.

In an additional aspect, the description provides kits comprising, e.g., a first vector, wherein a first nucleotide sequence encoding a target protein and a second nucleotide sequence encoding the modulator are cloned into the first vector, and a second vector, wherein a third nucleotide sequence encoding a nanobody is cloned into the second vector, and wherein the vectors comprise promoter sequences operably linked to the nucleotide sequences.

In a further aspect, the description provides methods for screening compounds that bind to TorsinA, including: providing a protein composition comprising TorsinA as described above, and a library of test compounds; treating the protein composition with a test compound; determine whether the compound binds to TorsinA, where a compound that binds to TorsinA is indicative of a compound that is a candidate TorsinA agonist or antagonist; and optionally determining a three dimensional crystal structure of TorsinA with and/or without the bound compound to a resolution of about 1.4 Å or better.

In certain embodiments, the modulator is a TorsinA agonist. In certain additional embodiments, the modulator is a TorsinA antagonist. In certain embodiments, the crystals of TorsinA are grown using a protein composition comprising: TorsinA having the amino acid sequence set forth in at leaset one of SEQ ID NO: 1-3 or a portion thereof, a modulator of the TorsinA having the amino acid sequence set forth in the SEQ ID NO: 4 or a portion thereof, and a nanobody specifically binds to at least one of the TorsinA and the modulator, and having the amino acid sequence set forth in the SEQ ID NO: 5 or a portion thereof.

In certain embodiments, the TorsinA comprises TorsinA ΔE303 having the amino acid sequence set forth in the SEQ ID NO: 3, and the protein composition is crystallized to obtain crystals of space group $P2_12_12_1$ with approximate a=75.5 Å, b=88.1 Å, and c=105.4 Å such that the three dimensional structure of the crystallized protein composition having the TorsinA ΔE303, the crystallized protein composition having TorsinA ΔE303 can be determined to a resolution of about 1.4 Å or better (TorsinA 51-332/E171Q/ΔE303 mutant structure).

In certain embodiments, the TorsinA comprises TorsinA E171Q having the amino acid sequence set forth in the SEQ ID NO: 2, and the protein composition is crystallized to obtain crystals of space group $P2_12_12_1$ with approximate a=75.7 Å, b=90.7 Å, and c=105.1 Å such that the three dimensional structure of the crystallized protein composition having TorsinA E171Q can be determined to a resolution of about 1.4 Å or better (TorsinA 51-332/E171Q).

In certain embodiments, a binding location of the modulator is determined by comparing the three dimensional structure of the crystallized protein composition having TorsinA ΔE303 and the three dimensional structure of the crystallized protein composition having TorsinA E171Q.

In certain embodiments, the modulator is virtually screened against the binding location of the three dimensional structure of the TorsinA ΔE303.

In certain embodiments, the modulator is co-crystallized with the TorsinA ΔE303 and at least one of the modulator and the nanobody to obtain a three dimensional structure having the TorsinA ΔE303 and the modulator, such that modification of the modulator is conducted based on the three dimensional structure having the TorsinA ΔE303.

Another aspect of the present invention relates to a modulator screened and iteratively improved using the three dimensional structure of TorsinA.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

FIG. 9 is side-by-side comparison of TorsinA-ATP-LULL1 (left) and TorsinAΔE-ATP-LULL1 (right). Zoomed insets show the atomic details of the interactions between TorsinA/TorsinAΔE and LULL1, with a focus on the ΔE303 area. FIGS. 10A and 10B are mutational analysis of the TorsinA-LULL1 interface. Substitution or deletion of residues involved in TorsinA-LULL1 binding were probed using a Ni-affinity co-purification assay with recombinant, bacterial-expressed protein. Only TorsinA is His-tagged. SDS-PAGE analysis is shown. Lack of binding is observed by the absence of complex (uncomplexed His-tagged TorsinA is insoluble). t, total lysate, e, Ni eluate. Asterisk denotes an unrelated contaminant.

FIG. 11A, Left, Schematic representation of a hypothetical heterohexameric (TorsinA-LULL1)$_3$ ring model, in analogy to canonical AAA+ ATPases. White star represents ATP. Since LULL1 cannot bind a nucleotide, there would be three catalytic (nucleotide-bound) and three non-catalytic interfaces per ring. Open-book representation of the catalytic interface between TorsinA and LULL1, as seen in this study. Black line marks the outline of the interface. Color gradient marks conservation across diverse eukaryotes. FIG. 11B, the same analysis as in a, but for the hypothetical 'non-catalytic' interface. The interface model on the right is based on swapping the TorsinA and LULL1 positions in the TorsinA-LULL1 complex.

FIGS. 12A and 12B show structure comparisons. FIG. 12A, human TorsinA-ATP (left) displayed as a cartoon, compared to the D2 domain of the double-ringed AAA+ ATPase ClpB-AMPPCP from *Thermus thermophilus* [46] (PDB code 4119; right) in the same orientation. Important structure motifs are labeled. FIG. 12B, human LULL1 (orange) superposed on human LAP1 (grey, PDB code 4TVS). The one region of major structural difference is labeled.

FIG. 14 shows phylogenetic analysis of LAP1/LULL1. Maximally diverged LAP1 and LULL1 sequences are aligned. If not experimentally confirmed, sequences were assigned as LAP1 or LULL1 based on the presence of an N-terminal, extraluminal domain with basic signature, characteristic of LAP1. Secondary structure elements of human LULL1 are displayed above the alignment. The strictly conserved Arg-finger is boxed. TorsinA contacts, red circles, conserved cysteines, yellow circles. Disulfide bridge depicted as a yellow line. hs, *Homo sapiens*; oa, *Ornithorhynchus anatinus*; gg, *Gallus gallus*; tr, *Takifugu rubripes*; dr, *Danio rerio*; nv, *Nematostella vectensis*; bf, *Branchiostoma floridae*; stp, *Strongylocentrotus purpuratus*; ci, *Ciona intestinalis*; ce, *Caenorhabditis elegans*; dm, *Drosophila melanogaster*; ta, *Trichoplax adherens*. hsLULL1 (SEQ ID NO: 31); hsLAP1 (SEQ ID NO: 32); ggLULL1 (SEQ ID NO: 33); ggLAP1 (SEQ ID NO: 34); trLULL1 (SEQ ID NO: 35); trLAP1 (SEQ ID NO: 36); drLULL1 (SEQ ID NO: 37); drLAP1 (SEQ ID NO: 38); oaLULL1 (SEQ ID NO: 39); oaLAP1 (SEQ ID NO: 40); stpLULL1 (SEQ ID NO: 41); stpLAP1 (SEQ ID NO: 42); taLULL1 (SEQ ID NO: 43); bfLULL1 (SEQ ID NO: 44); bfLAP1 (SEQ ID NO: 45); nvLAP1 (SEQ ID NO: 46); ciLULL1 (SEQ ID NO: 47); dmLULL1 (SEQ ID NO: 48); cdLULL1 (SEQ ID NO: 49); ceLAP1 (SEQ ID NO: 50).

FIG. 17 shows data collection and refinement statistics for TorsinA-LULL1$_{233-470}$ and TorsinAΔE-LULL1$_{233-470}$.

FIG. 18 shows a table of tystonia mutations.

DETAILED DESCRIPTION

Figure 1:
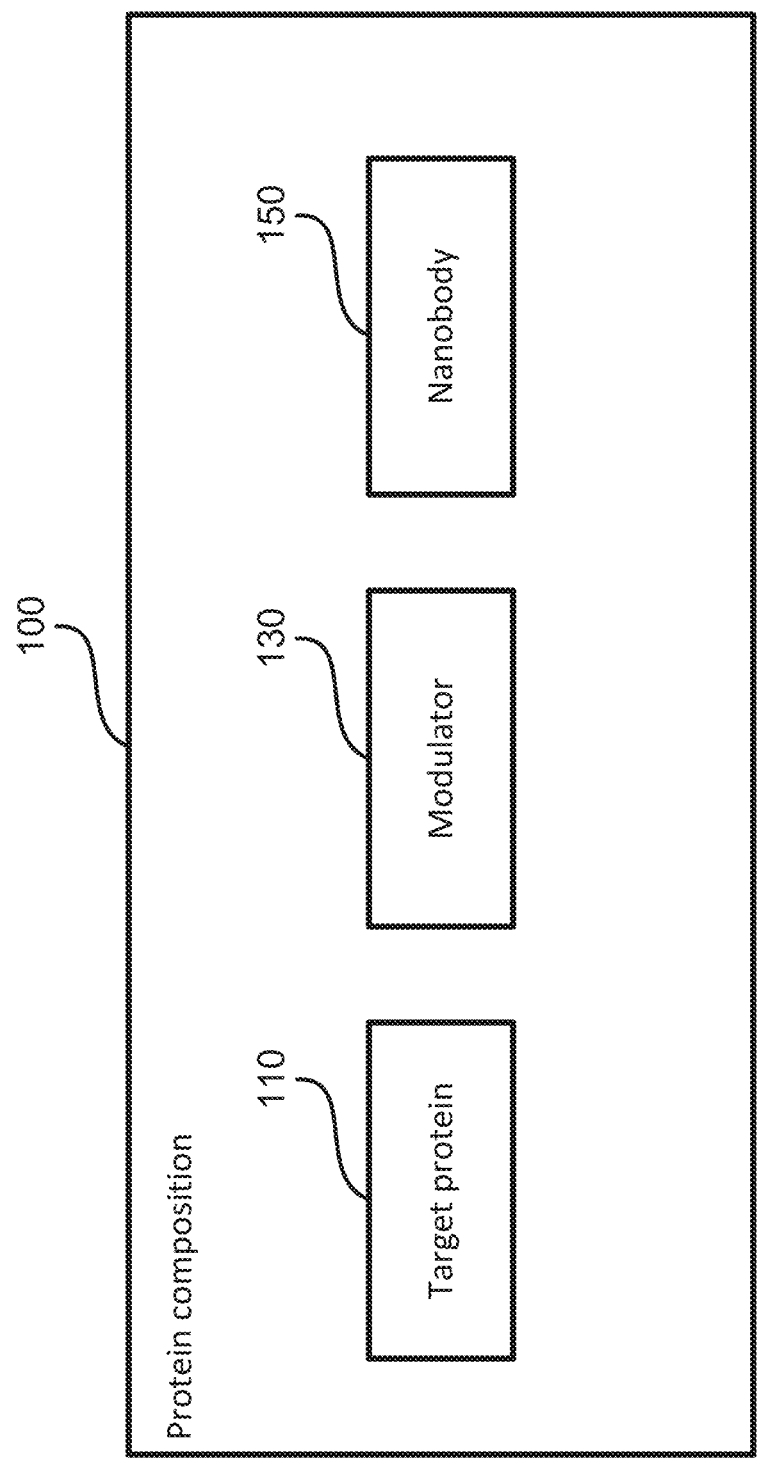
FIG. 1 shows a protein composition according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "plurality" means two or more.

As used herein, the terms "comprising", "including", "carrying", "having", "containing", "involving", and the like are to be understood to be open-ended, i.e., to mean including but not limited to.

The terms "TorsinA" or "Torsin-1A", as used herein, refer to a protein that in humans that is encoded by the TOR1A gene (also know as DQ2 or DYT1).

The term "nanobody", as used herein, refers to a single-domain antibody. The single-domain antibody is an antibody fragment consisting of a single monomeric variable antibody domain. Like a whole antibody, it is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

The term "modulator", as used herein, refer to a substance influencing the binding of a target protein to its ligand or agonist, or inverse agonist.

The most common cause of early onset primary dystonia, a neuromuscular disease, is a glutamate deletion ($\Delta E$) at position 302/303 of TorsinA, a AAA+ ATPase that resides in the endoplasmic reticulum including the perinuclear space [1, 2]. While the actual function of TorsinA remains elusive [3-6], the $\Delta E$ mutation is known to diminish binding of two TorsinA ATPase activators: lamina-associated protein 1 (LAP1) and its paralog, luminal domain like LAP1 (LULL1) [7-9]. Therefore, $\Delta E$ is likely a loss-of-function mutation [10]. A single-chain antibody fragment, a so-called nanobody, which specifically binds the TorsinA LULL1 complex, is generated. The nanobody is called VHH BS2. The resulting trimeric TorsinA(ATP)-LULL1-VHH-BS2 complex is stable in vitro and was crystallized. In addition, and most importantly, VHH-BS2 is able to stabilize the weak TorsinA$\Delta E$(ATP)•LULL1 interaction, thus a TorsinA$\Delta E$(ATP)-LULL1-VHH-BS2 can also be made and was crystallized as well. The ability to stabilize a weak interaction with a reagent like VHH-BS2 is extremely rare. Using a nanobody as a crystallization chaperone, both crystal structures are solved and refined to 1.4 Å resolution. A comparison of these structures at this very high resolution shows, in atomic detail, the subtle differences in activator interactions that separate the healthy wild type from the diseased state DYT1 mutant TorsinA. This structure information may provide a structural platform for drug development, as a small molecule that rescues TorsinAΔE could serve as a cure for primary dystonia.

In one aspect, the present invention relates to a protein composition. As shown in FIG. 1, in certain embodiments, the protein composition 100 includes a target protein 110, a modulator 130 of the target protein, a nanobody 150 specifically binds to at least one of the target protein and the modulator.

Figure 2A:
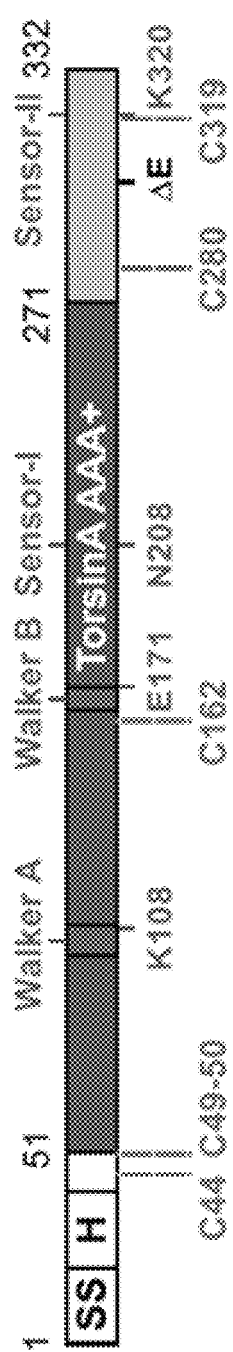
FIG. 2A shows a schematic diagram of TorsinA according to one embodiment of the present invention.

The target protein 110 may be human wild type TorsinA (SEQ ID NO: 1), mutant TorsinA$_{EQ}$ with a glutamate (E) to Glutamine (Q) mutation at position 171 (SEQ ID NO: 2), mutant TorsinA$_{EQ}$ΔE with a glutamate (E) to Glutamine (Q) mutation at position 171 and a glutamate deletion at position 303 (or 302) (SEQ ID NO: 3), as well as TorsinA mutants having ΔF323-Y328, R288Q, F205I, D194V, ΔA14-P15, E121K, V129I, or D216H mutations, and portions of the above proteins. In certain embodiments, the target protein 110 includes the amino acid sequence set forth in at least one of SEQ ID NO: 1-3 (SEQ ID NO: 1 is human TorsinA 51-332, SEQ ID NO: 2 is TorsinA 51-332 with E171Q; SEQ ID NO: 3 is human TorsinA 51-332 with E171Q and ΔE303) or portions thereof. FIG. 2A is schematically diagram of TorsinA, where important residues and sequence motifs are indicated. For example, SS is signal sequence, and H is hydrophobic region.

The modulator 130 may be an activator, an agonist, an antagonist, or an inverse agonist, of the target protein 110. When the target protein 110 is TorsinA or a mutant of TorsinA, the modulator 130 may be LAP1, LULL1, a domain or a portion of LAP1 or LULL1. In certain embodiments, the modulator may also be a drug lead that is able to bind to TorsinA or its mutant, and the drug lead may be improved based on the three dimensional complex structure of the TorsinA or its mutant and the drug lead. In certain embodiments, the modulator 130 is LULL1 or portions thereof. In one embodiment, the modulator comprises the amino acid sequence set forth in the SEQ ID NO: 4 (SEQ ID NO: 4 is LULL1 233-470) or portions thereof. FIG. 2A is schematically diagram of LULL1, where important residues and sequence motifs are indicated. For example, TM is transmembrane helix.

The nanobody 150 specifically binds to at least one of the target protein 110 and the modulator 130. In certain embodiments, the nanobody 150 may be obtained by immunizing a model animal using both the target protein 110 and the modulator 130. In certain embodiments, the nanobody is obtained by immunization using the target protein 110 having the amino acid sequence set forth in at least one of SEQ ID NO: 1-3 and the modulator 130 having the amino acid sequence set forth in the SEQ ID NO: 4, or portions thereof. In certain embodiments, the obtained nanobody 150 has the amino acid sequence set forth in the SEQ ID NO:5, or portions thereof.

In certain embodiments, the target protein 110 includes the amino acid sequence set forth in the SEQ ID NO: 2 or SEQ ID NO: 3 or portions thereof, the modulator 130 includes the amino acid sequence set forth in the SEQ ID NO: 4 or portions thereof, the nanobody 150 includes the amino acid sequence set forth in the SEQ ID NO: 5 or portions thereof, and the target protein 110, the modulator 130 and the nanobody 150 in the protein composition are co-expressed and purified together.

Figure 3:
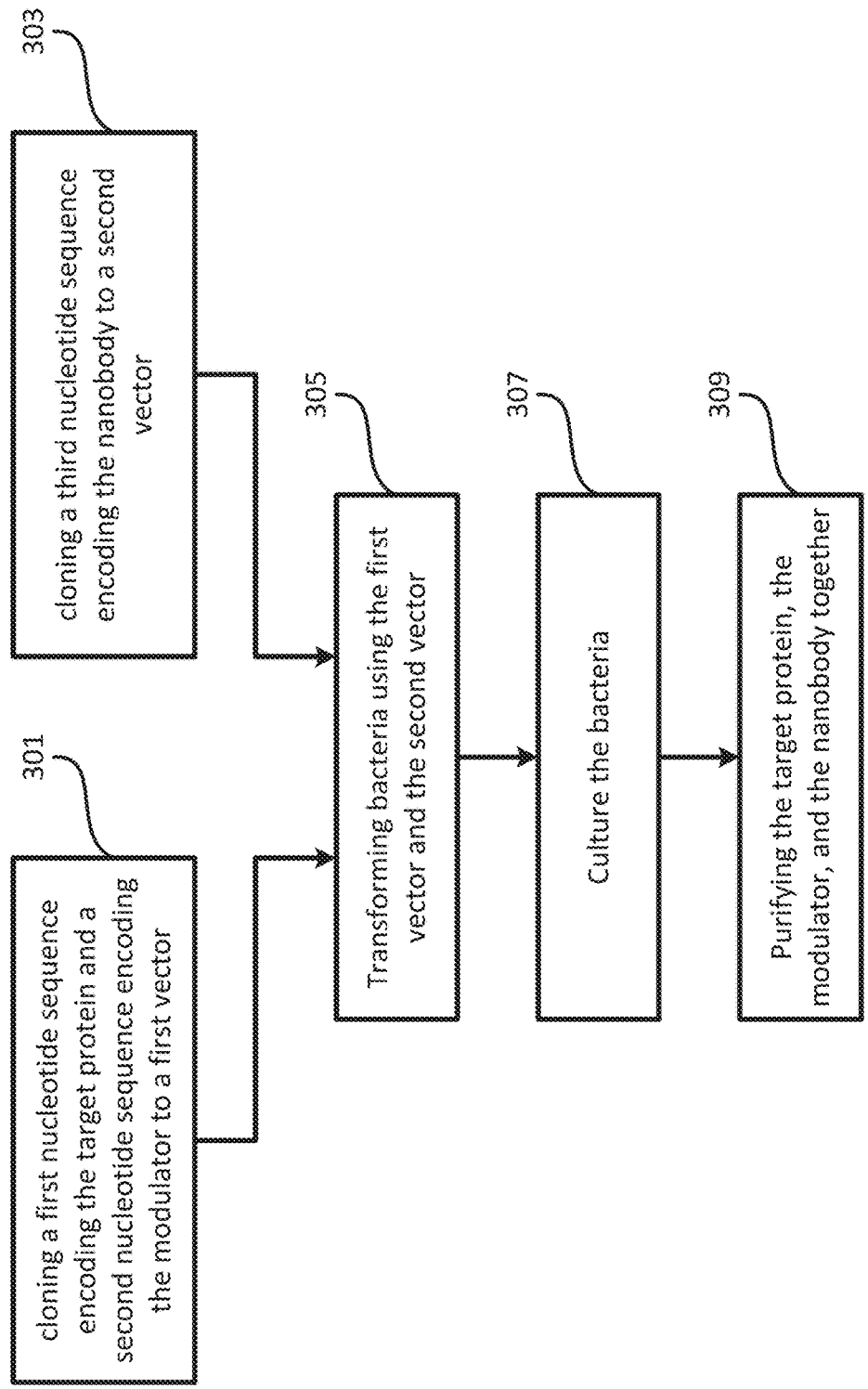
FIG. 3 shows a flowchart of preparing a TorsinA protein composition according to one embodiment of the present invention.

Referring to FIG. 3, in certain embodiments, the protein composition 100 is obtained through steps 301 to 309. In step 301, a first nucleotide sequence encoding the target protein 110 and a second nucleotide sequence encoding the modulator 130 are cloned into a first vector, and in step 303 a third nucleotide sequence encoding the nanobody 150 is cloned into a second vector. At step 305, the first vector and the second vector are used to transform bacteria. In certain embodiments, the first nucleotide sequence comprises the nucleic acid sequence set forth in at least one of SEQ ID NO: 6-8 (encoding the proteins SEQ ID NO: 1-3, respectively), the second nucleotide sequence comprises the nucleic acid sequence set forth in the SEQ ID NO: 9 (encoding the protein SEQ ID NO: 4), and the third nucleotide sequence comprises the nucleic acid sequence set forth in the SEQ ID NO: 10 (encoding the protein SEQ ID NO: 5). In certain embodiments, the first vector is a modified ampicillin resistant pETDuet-1 vector, the second vector is a pET-30b(+) vector, and the bacteria is E. coli strain LOBSTR(DE3) RIL. At step 307, the bacteria is cultured and the expression of the target protein 110, the modulator 130 and the nanobody 150 is induced. At step 309, the bacteria culture is harvested and the target protein 110, the modulator 130 and the nanobody 150 are purified together.

In certain embodiments, the target protein 110 includes the amino acid sequence set forth in the SEQ ID NO: 2, the modulator 130 includes the amino acid sequence set forth in the SEQ ID NO: 4, and the protein composition 100 is crystallized to obtain crystals of space group $P2_12_12_1$ with approximate a=75.7 Å, b=90.7 Å, and c=105.1 Å such that the three dimensional structure of the crystallized protein composition 110 can be determined to a resolution of about 1.4 Å or better (TorsinA$_{EQ}$51-332 structure).

Figure 4:
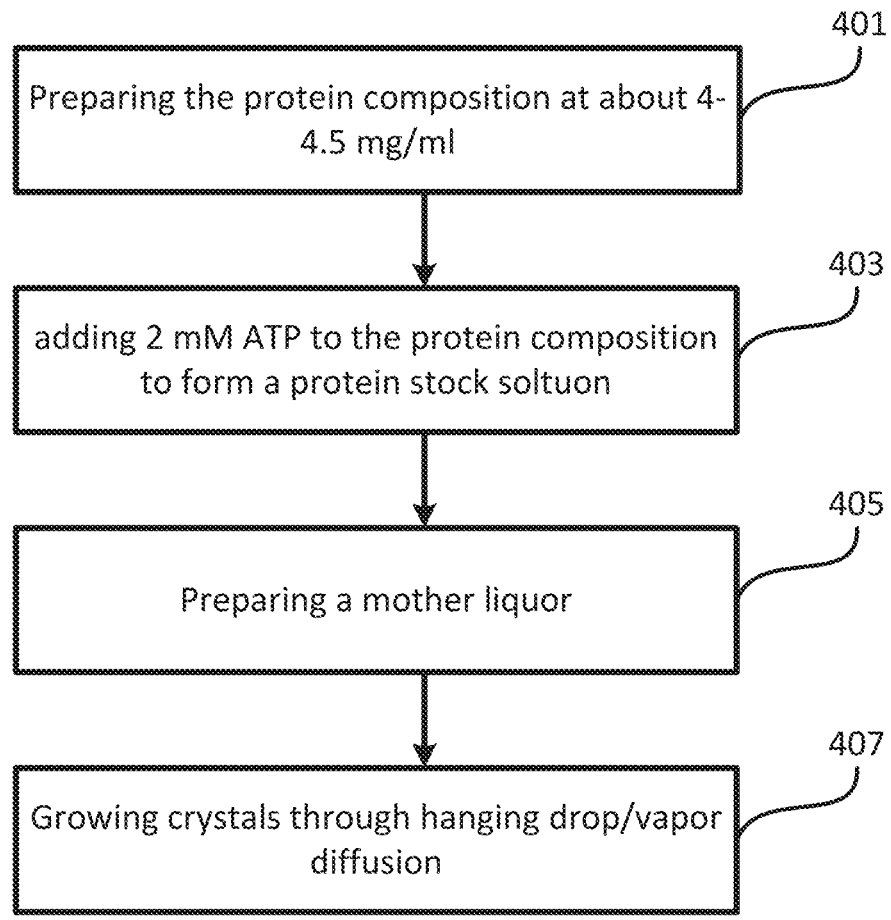
FIG. 4 shows a flowchart of obtaining crystals from a TorsinA protein composition according to one embodiment of the present invention.

In certain embodiments, as shown in FIG. 4, the protein composition 100 is crystallized to obtain crystals by the following steps. At step 401, the protein composition 100 is prepared, for example, by concentrating, to a concentration of about 4-4.5 mg/ml. At step 403, about 2 mM ATP is added to the concentrated protein composition 110 to form a protein stock solution. At step 405, a mother liquor is prepared. The mother liquor used in this embodiment includes 13% (w/v) polyethylene glycol (PEG) 6000, 5% (v/v) 2-methyl-2,4-pentanediol, and 0.1M MES pH6.5. At step 407, crystals are grow using hanging drop/vapor diffusion method. In this embodiment, approximately equal amount of protein stock solution and the mother liqor, for example 1 μl of the protein stock solution and 1 μl of the mother liquor, are mixed and disposed on a cover slip, and the cover slip is inverted, sealed, and covered on a reservoir having certain amount of the mother liquor, such as 0.5 ml or 1 ml. The vapor diffusion process between the hanging drop and the mother lique is conducted under a temperature, such as 18° C. or room temperature, and crystals are obtained in about a few days, such as 3-5 days.

After the crystals are observed and grow to a sufficient size, the crystals are cryoprotected by flash-frozen in liquid nitrogen after soaking in the mother liquor supplemented with 20% (v/v) glycerol. Single crystal is preferably used in the flash-frozen. X-ray data are collected using one of the obtained crystals, and the structure of the crystallized protein composition is determined based on the collected x-ray data.

In certain embodiments, the target protein 110 includes the amino acid sequence set forth in the SEQ ID NO: 3 or portions thereof, the modulator 130 includes the amino acid sequence set forth in the SEQ ID NO: 4 or portions thereof, and the protein composition 100 is crystallized to obtain crystals of space group $P2_12_12_1$ with approximate a=75.5 Å, b=88.1 Å, and c=105.4 Å such that the three dimensional structure of the crystallized protein composition can be determined to a resolution of about 1.4 Å or better (TorsinA$_{EQ}$51-332 ΔE303 mutant structure).

In certain embodiments, the protein composition 100 is crystallized to obtain crystals by the following steps: preparing the protein composition 100 at about 4-4.5 mg/ml; adding about 2 mM ATP to the prepared protein composition to form a protein stock; preparing a mother liquor comprising about 19% (w/v) polyethylene glycol (PEG) 3350, about 0.2 M AMSO$_4$, and about 0.1 M Bis-Tris-HCl pH6.5; and mixing 1 µl of the protein stock with 1 µl of the mother liquor to form a second mixture, and inducing crystallization of the protein composition in the mixture by hanging drop/vapor diffusion under about 18° C., such that the crystals are obtained in about 3-5 days.

In certain embodiments, the obtained crystals are cryoprotected by flash-frozen in liquid nitrogen after soaking in the mother liquor supplemented with 20% (v/v) glycerol, x-ray data are collected using one of the obtained crystals, and the structure of the crystallized protein composition is determined based on the collected x-ray data.

In another aspect, the present invention related to a method of determining the three dimensional structure of a crystallized protein composition 100 to a resolution of about 1.4 Å or better. In certain embodiments, the protein composition 100 includes a target protein 110 having the amino acid sequence set forth in at least one of SEQ ID NO: 1-3 or portions thereof, an modulator 130 of the target protein 110 having the amino acid sequence set forth in the SEQ ID NO: 4 or portions thereof, and a nanobody 150 specifically binds to at least one of the target protein 110 and the modulator 130 and having the amino acid sequence set forth in the SEQ ID NO: 5 or portions thereof.

Figure 5:
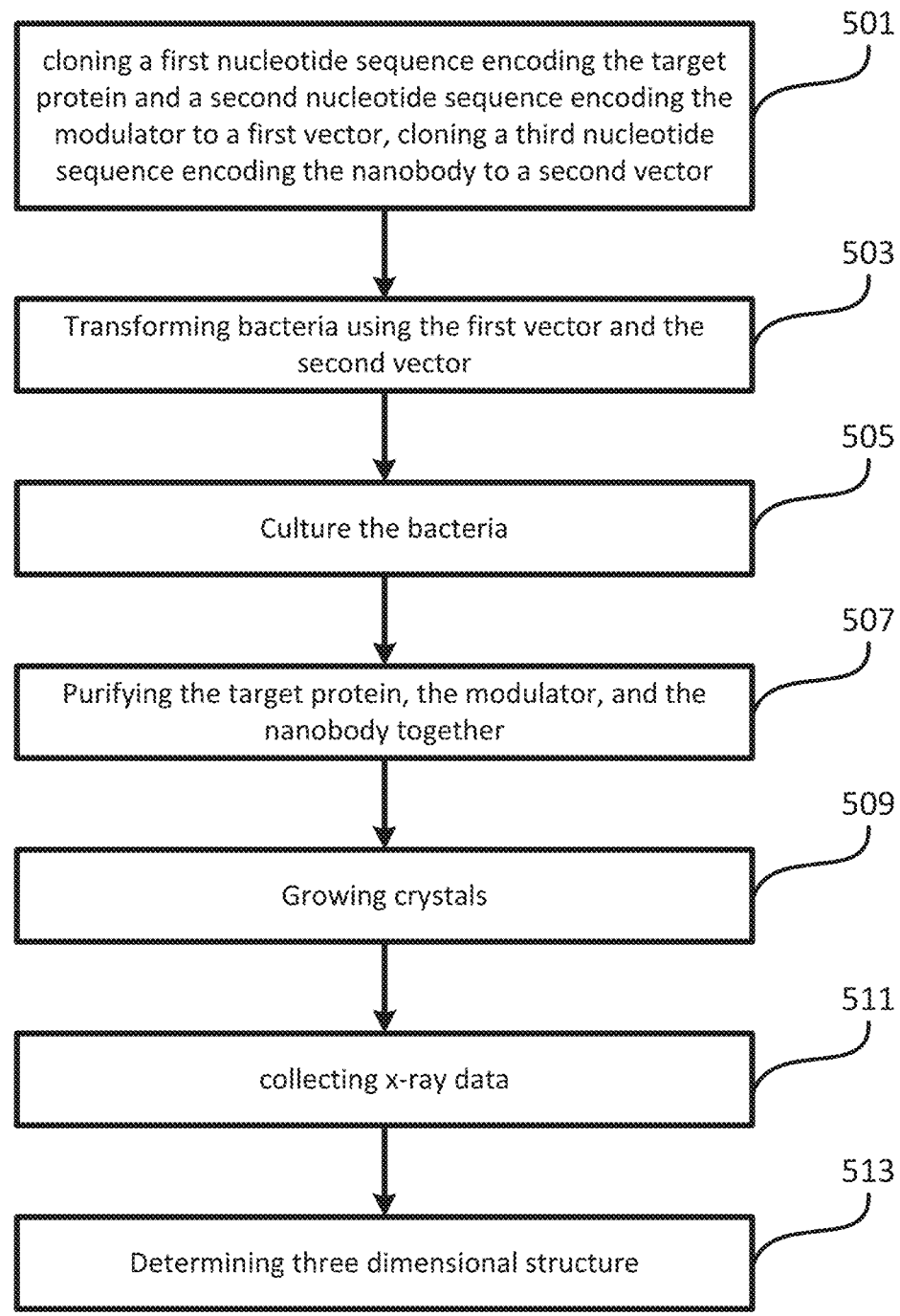
FIG. 5 shows a flowchart of determining three dimensional structures of TorsinA according to one embodiment of the present invention.

As shown in FIG. 5, the method includes the following steps. At steps 501, preparing a first nucleotide sequence having the nucleic acid sequence set forth in at least one of SEQ ID NO: 6-8 (encoding the proteins of SEQ ID NO: 1-3, respectively), a second nucleic acid sequence set forth in the SEQ ID NO: 9 (encoding the protein SEQ ID NO: 4) is prepared, and a third nucleotide sequence having the nucleic acid sequence set forth in the SEQ ID NO: 10 (encoding the protein SEQ ID NO: 5) is prepared. The preparation may be performed by direct synthesis or from PCR. Then the first nucleotide sequence and the second nucleotide sequence is cloent to a first vector, and the third nucleotide sequence is cloned to a second vector. At step 503, bacteria are transformed using the first vector and the second vector. At step 505, the bacteria are grown to express the target protein, the modulator and the nanobody. At step 507, the target protein, the modulator and the nanobody are purified together to obtain a protein composition. At step 509, the protein composition is crystallized to obtain crystals. At step 511, x-ray data is collected using one of the obtained crystals. At step 513, the three dimensional structure from the collected x-ray data is determined.

In certain embodiments, the target protein 110 comprises the amino acid sequence set forth in the SEQ ID NO: 2, and the protein composition 100 is crystallized to obtain crystals of space group P2$_1$2$_1$2$_1$ with approximate a=75.7 Å, b=90.7 Å, and c=105.1 Å such that the three dimensional structure of the crystallized protein composition 100 can be determined to a resolution of about 1.4 Å or better (TorsinA$_{EQ}$ 51-332 structure).

In certain embodiments, the target protein 110 comprises the amino acid sequence set forth in the SEQ ID NO: 3, and the protein composition 100 is crystallized to obtain crystals of space group P2$_1$2$_1$2$_1$ with approximate a=75.5 Å, b=88.1 Å, and c=105.4 Å such that the three dimensional structure of the crystallized protein composition can be determined to a resolution of about 1.4 Å or better (TorsinA$_{EQ}$ ΔE303 mutant structure).

In a further aspect, the present invention relates to a method for screening compounds that bind to TorsinA. In certain embodiments, the method includes providing a protein composition as described above comprising TorsinA, and a library of test compounds, treating the protein composition with a test compound, determining whether the compound binds to TorsinA, where a compound that binds TorsinA is indicative of a compound that is a candidate TorsinA agonist or antagonist, and optionally determining a three dimensional crystal structure of TorsinA with and/or without the bound compound to a resolution of about 1.4 Å or better.

The TorsinA structure may include TorsinA$_{EQ}$ structure, TorsinA$_{EQ}$ΔE303 structure, as well as their complex structures with modulators such as LULL1 or LAP1, and/or ATP. After analyzing one or more of the three dimensional structures of TorsinA, a targeting binding area of TorsinA or a targeting binding interface between TorsinA and its modulator, is chosen for designing a lead as drug candidate. The lead may be rationally designed, virtually screened, or directly screened by activity. The lead is then crystallized, for example using the method as shown in FIG. 5, with TorsinA. Then the TorsinA/lead complex structure is determined, and the structure information can be used for further optimization of the lead. A drug may be obtained fro iterary optimization of the lead.

In certain embodiments, the crystals of TorsinA are grown using a protein composition 100 including: TorsinA having the amino acid sequence set forth in at least one of SEQ ID NO: 1-3 or portions thereof, a modulator of TorsinA having the amino acid sequence set forth in the SEQ ID NO: 4 or portions thereof, and a nanobody specifically binds to at least one of TorsinA and the modulator and having the amino acid sequence set forth in the SEQ ID NO: 5 or portions thereof.

In certain embodiments, TorsinA includes TorsinA$_{EQ}$ ΔE303 having the amino acid sequence set forth in the SEQ ID NO: 3, and the protein composition is crystallized to obtain crystals of space group P2$_1$2$_1$2$_1$ with approximate a=75.5 Å, b=88.1 Å, and c=105.4 Å such that the three dimensional structure of the crystallized protein composition having the TorsinA$_{EQ}$ ΔE303, the crystallized protein composition having TorsinA ΔE303 can be determined to a resolution of about 1.4 Å or better (TorsinA$_{EQ}$ 51-332 ΔE303 mutant structure).

In certain embodiments, the TorsinA comprises TorsinA E171Q having the amino acid sequence set forth in the SEQ ID NO: 2, and the protein composition is crystallized to obtain crystals of space group P2$_1$2$_1$2$_1$ with approximate a=75.7 Å, b=90.7 Å, and c=105.1 Å such that the three dimensional structure of the crystallized protein composition having TorsinA E171Q can be determined to a resolution of about 1.4 Å or better (TorsinA 51-332/E171Q).

In certain embodiments, a binding location of the modulator is determined by comparing the three dimensional structure of the crystallized protein composition having TorsinA ΔE303 and the three dimensional structure of the crystallized protein composition having TorsinA E171Q.

In certain embodiments, the modulator is virtually screened against the binding location of the three dimensional structure of the TorsinA$_{EQ}$ ΔE303.

In certain embodiments, the modulator is co-crystallized with the TorsinA$_{EQ}$ ΔE303 and at least one of the modulator and the nanobody to obtain a three dimensional structure having the TorsinA$_{EQ}$ ΔE303 and the modulator, such that modification of the modulator is conducted based on the three dimensional structure having the TorsinA ΔE303.

Certain embodiments of the present application, among other things, crystallized TorsinA which is a difficult to crystalize. Using this method, variety of TorsinA mutants and their complex structures can be determined. This is not achieved by any others before this invention.

Further, by comparing the TorsinA$_{EQ}$ structure and TorsinA$_{EQ}$ ΔE303 structure, a novel funcartional mechanism and novel binding site is determined, which can be used as the basis for structural based rational drug design. This information provides a structural platform to develop drug that can rescue TorsinA ΔE303 or other type of mutants so that the TorsinA ΔE303 become funcational. The drug is then useful for cure primary dystonia.

These and other aspects of the present invention are more specifically described below. Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

EXAMPLES

Example 1: Generation and Selection of Nanobodies

Figure 2B:
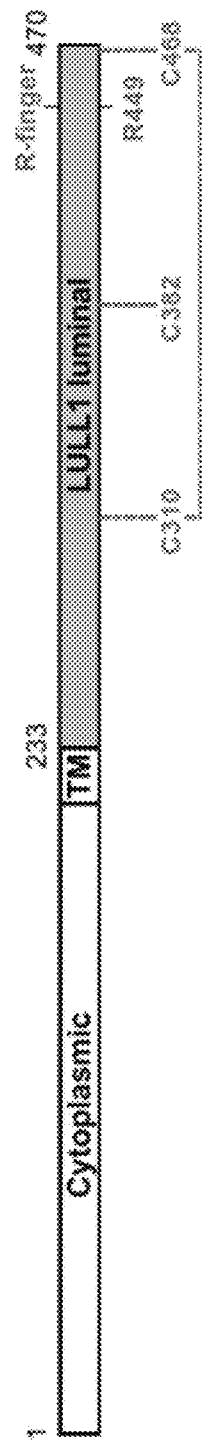
FIG. 2B shows a schematic diagram of LULL1 according to one embodiment of the present invention. The gray areas mark the crystallized segments. Large domain of TorsinA is darker than the small domains of TorsinA. SS, signal sequence; H, hydrophobic region; TM, transmembrane helix.

To investigate the molecular basis for primary dystonia as a result of the glutamate 302/303 deletion in TorsinA, a structural approach is taken. TorsinA is a catalytically inactive AAA+ ATPase [11-13], notoriously ill-behaved in vitro, primarily due to its limited solubility and stability. These problems were partially overcome by stabilizing an ATP-trapped E171Q mutant of human TorsinA (residues 51-332; SEQ ID NO: 2) by co-expressing it with the luminal activation domain of human LULL1 (residues 233-470; SEQ ID NO: 4). This resulted in a better behaved heterodimeric complex (FIGS. 2A and 2B), but was still recalcitrant to initial crystallization efforts. To facilitate crystallization, isolated a nanobody (VHH-BS2; SEQ ID NO: 5) was isolated from an alpaca immunized with the TorsinA$_{EQ}$-LULL1 complex. A stable, heterotrimeric complex of TorsinA$_{EQ}$(ATP)-LULL1-VHH-BS2 was readily crystallized in the presence of ATP.

Specifically, for obtaining the VHH-BS2 nanobody, purified human TorsinA$_{EQ}$-LULL1 complex was injected into a male alpaca (Lama pacos) for immunization. Generation and screening of nanobodies was carried out as previously described [14]. Each of the selected nanobodies was subcloned into a pET-30b(+) vector with a C-terminal His$_6$-tag. Each nanobody was bacterially expressed and Ni$^{2+}$-affinity purified essentially as described (see below). Different from the TorsinA-containing preparations, MgCl$_2$ and ATP were eliminated from all buffer solutions. The Ni$^{2+}$-eluate was purified via size exclusion chromatography on a Superdex S75 column (GE Healthcare) in running buffer (10 mM HEPES/NaOH pH 8.0, 150 mM NaCl). Nanobody binding was validated by size exclusion chromatography on a 10/300 Superdex S200 column in 10 mM HEPES/NaOH pH 8.0, 150 mM NaCl, 10 mM MgCl$_2$ and 0.5 mM ATP.

Equimolar amounts of TorsinA$_{EQ}$-LULL1 and TorsinA$_{EQ}$-LULL1-VHH were loaded and nanobody binding was monitored by a shift in the elution profile and via SDS-PAGE analysis. After validating VHH-BS2 interaction with TorsinA$_{EQ}$-LULL1, the C-terminal His$_6$-tag of VHH-BS2 was removed from the pET-30b(+) vector for co-purification experiments.

Example 2: Constructs, Protein Expression and Purification

DNA sequences encoding human TorsinA (residues 51-332) and the luminal domain of human LULL1 (residues 233-470) were cloned into a modified ampicillin resistant pETDuet-1 vector (EMD Millipore). TorsinA, N-terminally fused with a human rhinovirus 3C protease cleavable 10xHis-7xArg tag, was inserted into the first multiple cloning site (MCS), whereas the untagged LULL1 was inserted into the second MCS. Mutations on TorsinA and LULL1 were introduced by site-directed mutagenesis. The untagged VHH-BS2 nanobody was cloned into a separate, modified kanamycin resistant pET-30b(+) vector (EMD Biosciences).

To co-express TorsinA (EQ or EQ/ΔE), LULL1 and VHH-BS2 for crystallization, the *E. coli* strain LOBSTR (DE3) RIL (Kerafast) [32] was co-transformed with the two constructs described above. Cells were grown at 37° C. in lysogeny broth (LB) medium supplemented with 100 µg ml$^{-1}$ ampicillin, 25 µg ml$^{-1}$ kanamaycin and 34 µg ml$^{-1}$ hloramphenicol until an optical density (OD$_{600}$) of 0.6-0.8 was reached, shifted to 18° C. for 20 min, and induced overnight at 18° C. with 0.2 mM isopropyl β-D-1-thiogalactopyranoside (IPTG). The bacterial cultures were harvested by centrifugation, suspended in lysis buffer (50 mM HEPES/NaOH pH 8.0, 400 mM NaCl, 40 mM imidazole, 10 mM MgCl$_2$, and 1 mM ATP) and lysed with a cell disruptor (Constant Systems). The lysate was immediately mixed with 0.1 M phenylmethanesulfonyl fluoride (PMSF) (50 µl per 10 ml lysate) and 250 units of TurboNuclease (Eton Bioscience), and cleared by centrifugation. The soluble fraction was gently mixed with Ni-Sepharose 6 Fast Flow (GE Healthcare) resin for 30 min at 4° C. After washing with the lysis buffer, bound protein was eluted in elution buffer (10 mM HEPES/NaOH pH 8.0, 150 mM NaCl, 300 mM imidazole, 10 mM MgCl$_2$, and 1 mM ATP). The eluted protein complex was immediately purified by size exclusion chromatography on a Superdex S200 column (GE Healthcare) equilibrated in running buffer (10 mM HEPES/NaOH pH 8.0, 150 mM NaCl, 10 mM MgCl$_2$, and 0.5 mM ATP). Following the tag removal by 10xHis-7xArg-3C protease, the fusion tags and the protease were separated from the complex by cation-exchange chromatography on a HiTrapS column (GE Healthcare) using a linear NaCl gradient. The flow-through from the cation-exchange chromatography, containing the protein complex, was purified again by size exclusion chromatography on a Superdex S200 column as at the previous step.

For the non-structural analysis of TorsinA and LULL1 variants, the pETDuet-1-based expression plasmid was transformed into LOBSTR(DE3) RIL cells without co-expressing nanobody VHH-BS2. Ni$^{2+}$-affinity purification was performed as described above and bound protein was eluted. Aliquots from the Ni$^{2+}$-eluate and the total lysate were collected and analyzed by SDS-PAGE gel electrophoresis.

Example 3: Crystallization

Purified TorsinA$_{EQ}$-LULL1-VHH-BS2 and TorsinA$_{EQ}$ΔE-LULL1-VHH-BS2 complexes were concentrated up to 4-4.5 mg/ml and supplemented with 2 mM ATP prior to crystallization. The TorsinA$_{EQ}$ containing complex crystallized in 13% (w/v) polyethylene glycol (PEG) 6000, 5% (v/v) 2-Methyl-2,4-pentanediol, and 0.1 M MES pH 6.5. The TorsinA$_{EQ}$ΔE containing complex crystallized in 19% (w/v) PEG 3350, 0.2 M AmSO4, and 0.1 M Bis-Tris-HCl pH 6.5. Crystals of both complexes grew at 18° C. in hanging drops containing 1 µl of protein and 1 µl of mother liquor. Clusters of diffraction quality, rod-shaped crystals formed within 3-5 days. Single crystals were briefly soaked in mother liquor supplemented with 20% (v/v) glycerol for cryoprotection and flash-frozen in liquid nitrogen.

Example 4: Data Collection and Structure Determination

X-ray data were collected at NE-CAT beamline 24-ID-C at Argonne National Laboratory. Data reduction was performed with the HKL2000 package [33], and all subsequent data-processing steps were carried out using programs provided through SBGrid [34]. The structure of the TorsinA$_{EQ}$-LULL1-VHH-BS2 complex was solved by molecular replacement (MR) using the Phaser-MR tool from the PHENIX suite [35]. A three-part MR solution was easily obtained using a sequential search for models of LULL1, VHH-BS2, and TorsinA. The LULL1 model was generated based on the published human LAP1 structure (PDB 4TVS, chain A), using the Sculptor utility of the PHENIX suite (LULL1$_{1241-470}$ and LAP$_{1356-583}$ share 64% sequence identity). The VHH-BS2 model was based on VHH-BS1 (PDB 4TVS, chain a) after removing the complementarity determining regions (CDRs). The poly-Ala model of TorsinA was generated based on E. coli ClpA (PDB 1R6B) using the MODELLER tool of the HHpred server [36]. The asymmetric unit contains one TorsinA$_{EQ}$-LULL1-VHH-BS2 complex. Iterative model building and refinement steps gradually improved the electron density maps and the model statistics. The stereochemical quality of the final model was validated by Molprobity [37]. TorsinA$_{EQ}$ΔE-LULL1-VHH-BS2 crystallized in the same unit cell. Model building was carried starting from a truncated TorsinA$_{EQ}$-LULL1-VHH-BS2 structure. All manual model building steps were carried out with Coot [38], and phenix.refine was used for iterative refinement. Two alternate conformations of a loop in LULL1 (residues 428-438) were detected in the Fo-Fc difference electron density maps of both structures, and they were partially built. For comparison, the cysteine residues of TorsinA at the catalytic site (residues 280 and 319 in the TorsinA$_{EQ}$ structure) were built in the reduced and the oxidized states, respectively. Building them as oxidized, disulfide-bridged residues consistently produced substantial residual Fo-Fc difference density, which disappeared assuming a reduced state. Statistical parameters of data collection and refinement are all given in Table 1 in FIG. 17. Structure figures were created in PyMOL (Schrödinger LLC).

Example 5: Bioinformatic Analysis

Torsin and LAP1/LULL1 sequences were obtained via PSI-BLAST [39] and Backphyre searches [40]. Transmembrane domains were predicted using the HMMTOP tool [41]. LAP1/LULL1 proteins were distinguished based on the calculated isoelectric point (pI) of their extra-luminal portions. The intranuclear domain of LAP1 has a characteristically high pI of ~8.5-10 due to a clustering of basic residues, while the cytoplasmic domain of LULL1 is distinctively more acidic. Multiple sequence alignments were performed using MUSCLE [42], and visualized by Jalview [43]. To illustrate evolutionary conservation on TorsinA and LULL1 surfaces, conservation scores for each residue were calculated using the ConSurf server with default parameters [44].

Example 6: Structure Analysis

Figure 6:
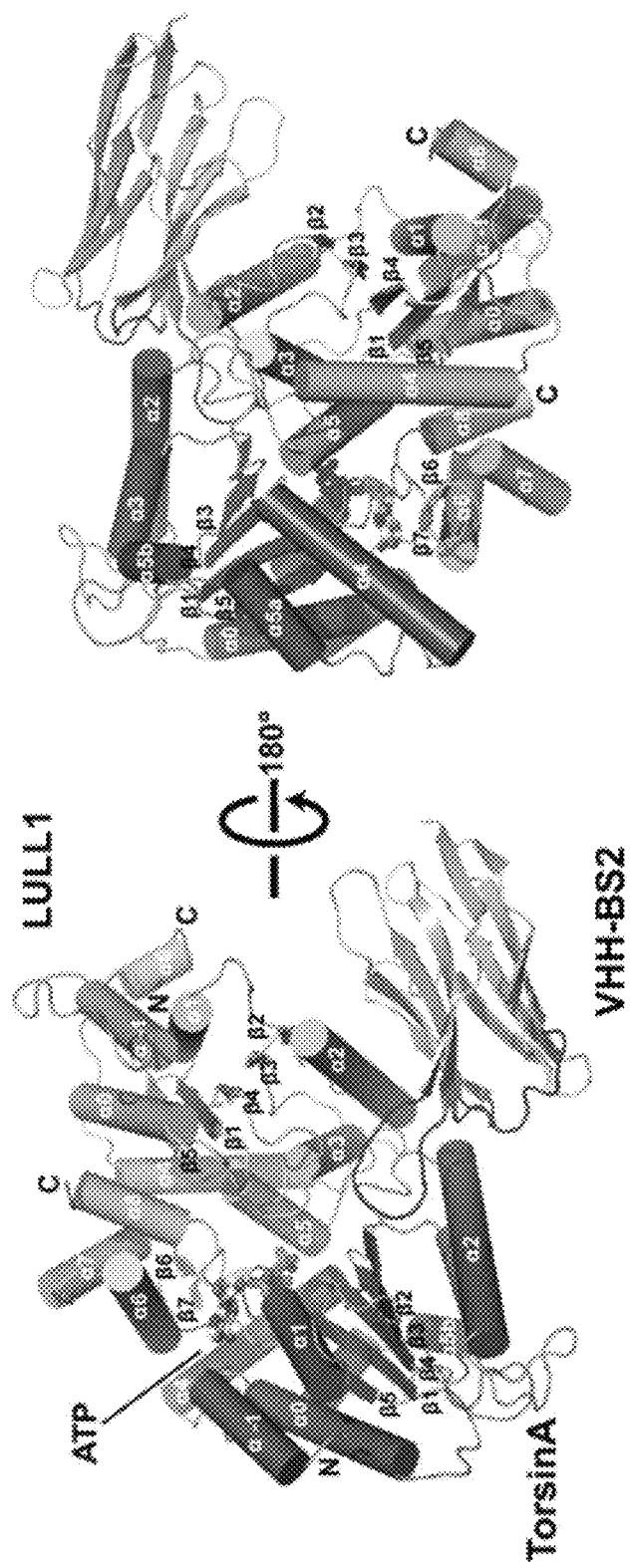
FIG. 6 is a cartoon representation of the TorsinA-LULL1 complex in two orientations. Large domain of TorsinA is darker than the small domains of TorsinA. A nanobody (VHH-BS2, grey; with complementarity determining regions darker) was used as a crystallization chaperone. Numbers refer to secondary structure elements.
Figure 7:
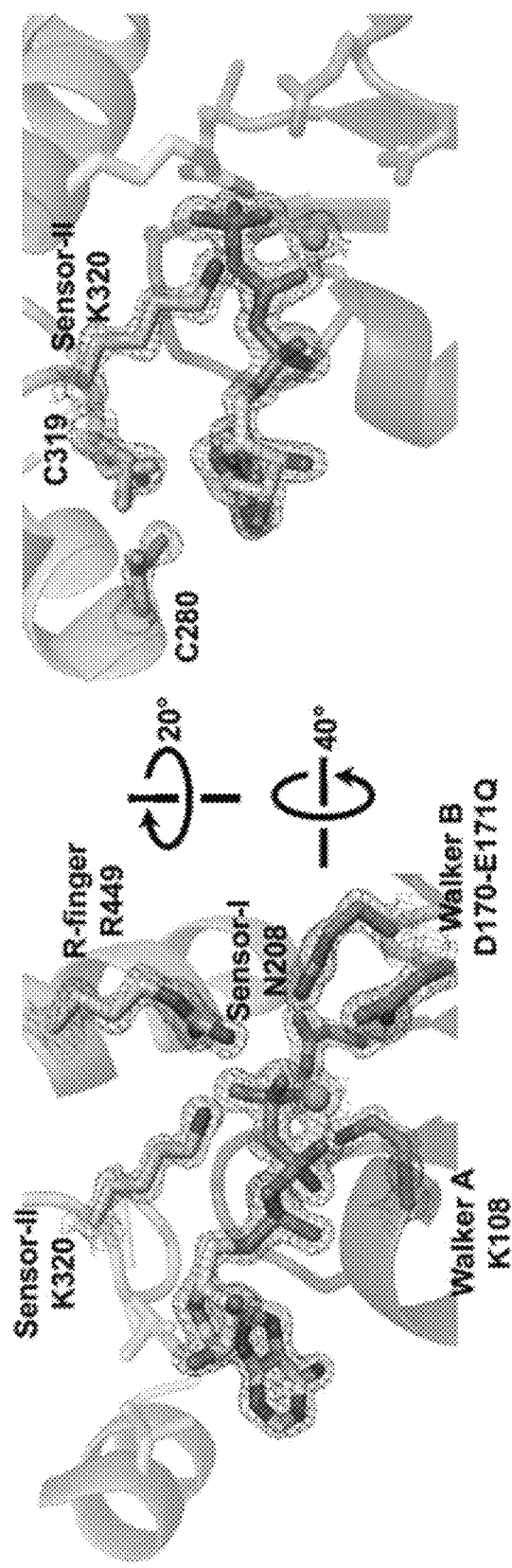
FIG. 7 is a close-up of the ATP binding site. Key residues are labeled. 2Fo-Fc electron density contoured at 2σ displayed as grey mesh.
Figure 15:
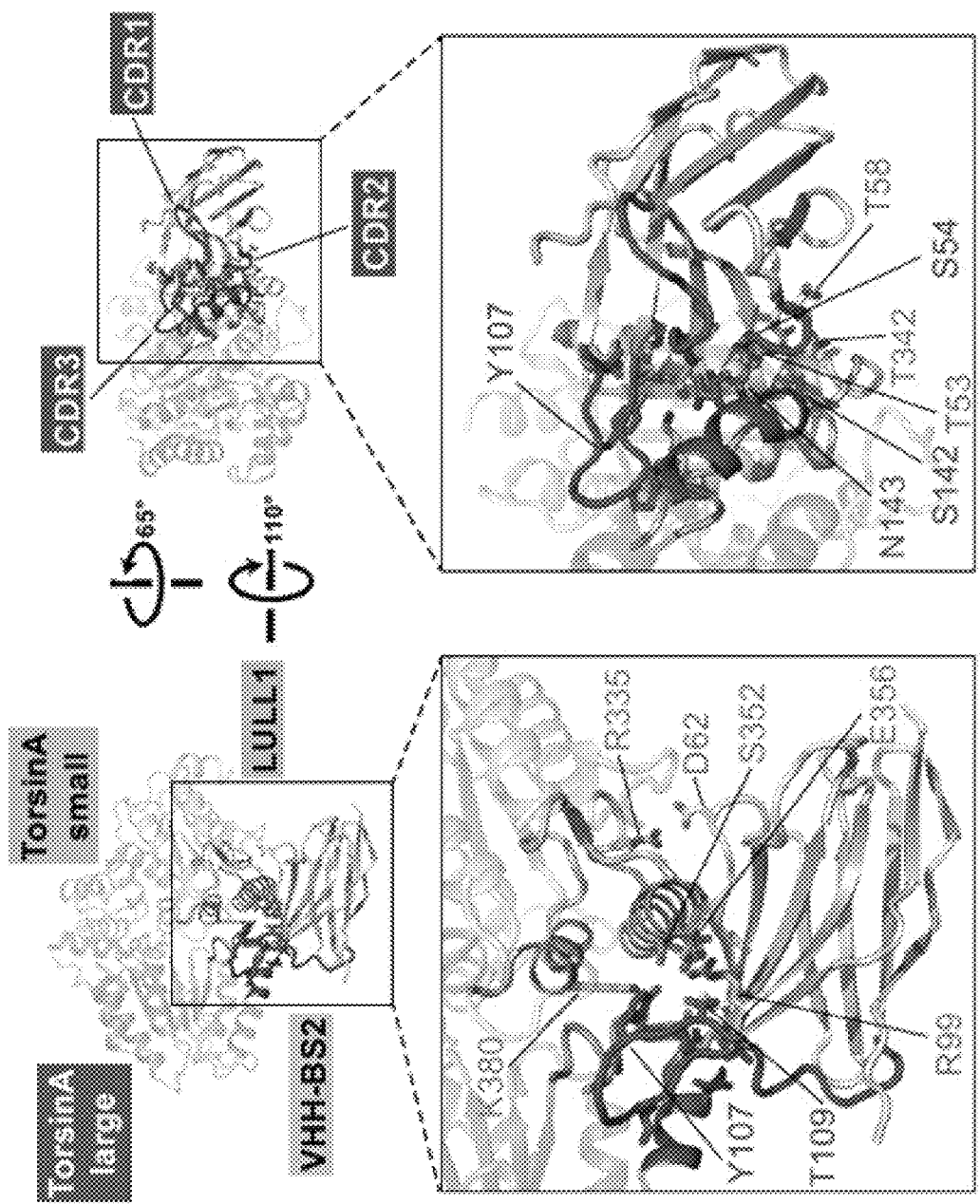
FIG. 15 shows nanobody interaction. The heterotrimeric TorsinA(ATP)-LULL1-VHH-BS2 complex is shown in two orientations. Nanobody and interacting secondary structure elements of TorsinA and LULL1 are shown in full color, non-interacting elements in faded colors. Complementarity determining regions (CDRs) in red. Insets show close-ups with important interacting residues labeled.

A stable, heterotrimeric complex of TorsinA$_{EQ}$(ATP)-LULL1-VHH-BS2 was readily crystallized in the presence of ATP. A 1.4 Å dataset was collected and the structure was solved by molecular replacement, using the LULL1-homolog LAP1 and a VHH template as search models [14] (Example 4, and Table 1 in FIG. 17). TorsinA$_{EQ}$ adopts a typical AAA+ ATPase fold (FIG. 6 and FIG. 12). The N-terminal nucleotide-binding or large domain (residues 55-271) is composed of a central five-stranded, parallel β-sheet surrounded by 8 α-helices. A small three-helix bundle at its C-terminus (residues 272-332), forms critical contacts with LULL1. The ATP molecule is bound in the manner characteristic of P-loop NTPases [15]. The Walker A and B motifs are positioned to mediate the requisite nucleotide interactions, with sensor 1 and sensor 2 regions sensing the γ-phosphate and thus the nucleotide-binding state (FIG. 7). The luminal LULL1 activation domain (residues 236-470) adopts an AAA+-like conformation, very similar to its paralog LAP1 (rmsd 1.05 Å over 213 Cα positions, FIG. 12). The AAA+-like domain comprises a central β-sheet embedded within six α-helices (FIG. 6). A C-terminal small domain is not found. Characteristically, LULL1 lacks nucleotide binding due to the absence of Walker A and B motifs [14]. LULL1 forms a composite nucleotide-binding site with TorsinA by providing arginine residue 449 ('arginine finger') at the base of helix α5 (FIG. 7). The arginine finger activates ATP hydrolysis by TorsinA [14,16]. The small domain of TorsinA, including helix α7 featuring glutamates 302 and 303, is intimately involved in LULL1 binding. Nanobody VHH-BS2 binds both TorsinA and LULL1 at a shallow groove (FIG. 6 and FIG. 15). Nanobodies contain three complementarity determining regions (CDRs), with CDR3 most often making critical contacts with the antigen [17]. Indeed, the long CDR3 of VHH-BS2 (residues 101-109) is the main binding element in the complex.

Figure 8:
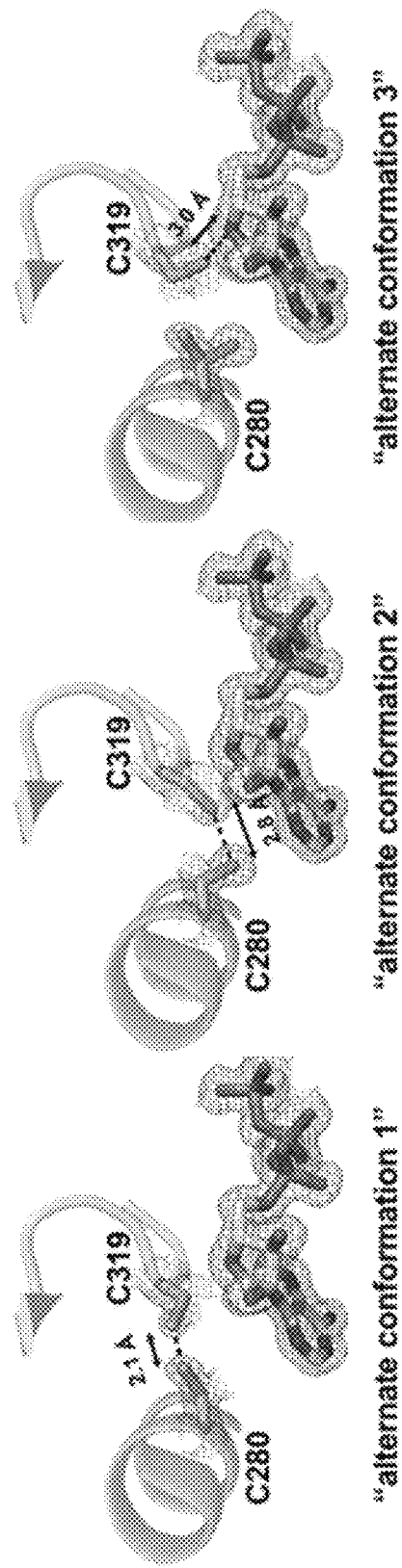
FIG. 8 is a close-up of the proximal cysteines 280 and 319 next to the adenine base of the bound ATP. 2Fo-Fc electron density is contoured at 1σ. The cysteine pair adopts three alternate conformations, but remains reduced in all of them.
Figure 13:
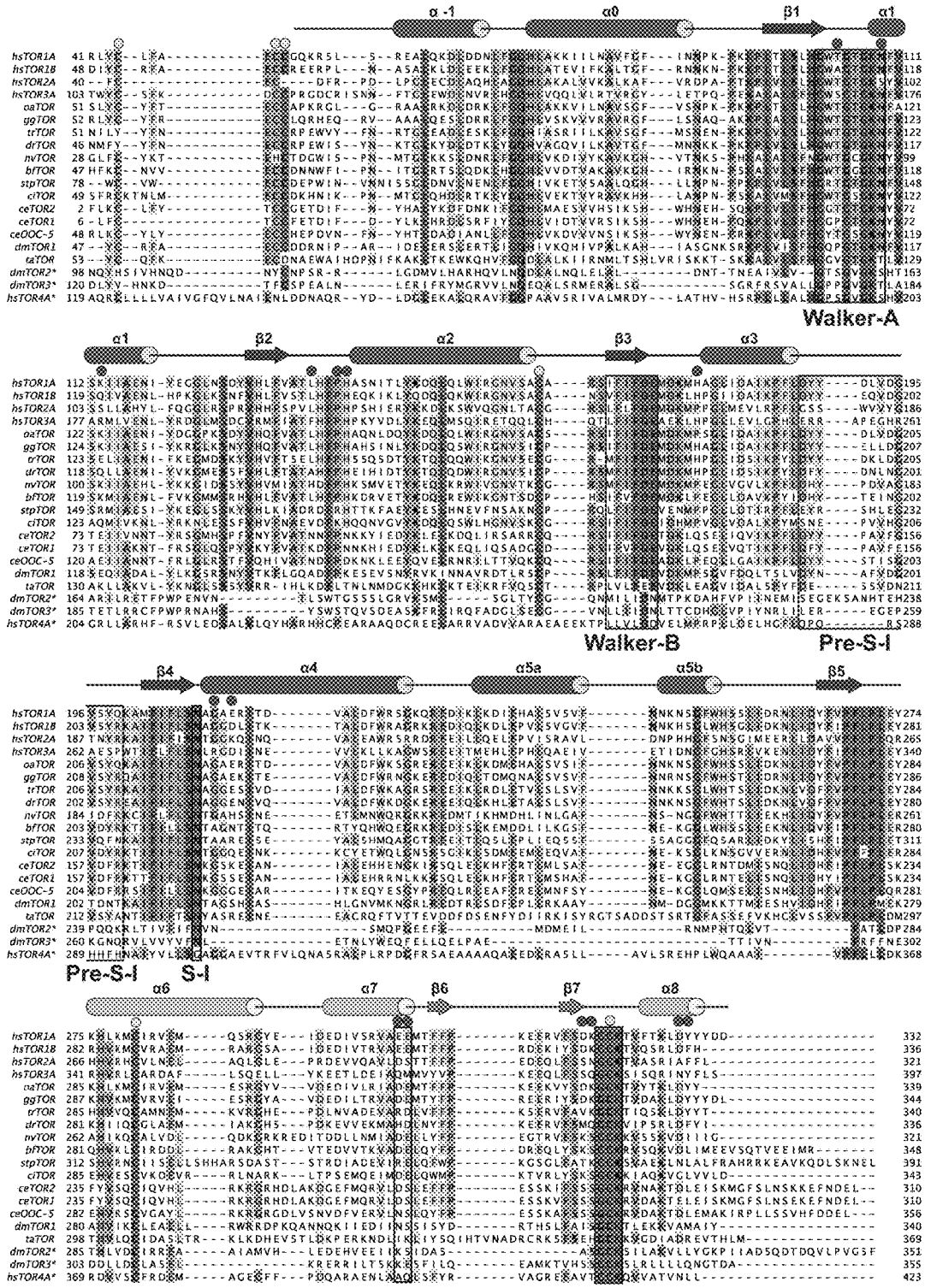
FIG. 13 shows phylogenetic analysis of Torsins. Maximally diverged torsins are aligned. Secondary structure elements of human TorsinA are displayed above the alignment. Important sequence motifs are boxed. LULL1 contacts, red circles, conserved cysteines, yellow circles. Proximal cysteines 280 and 319 connected with a dashed yellow line. Asterisk denotes putative torsin homologs based on sequence analysis. hs, *Homo sapiens*; oa, *Ornithorhynchus anatinus*; gg, *Gallus gallus*; tr, *Takifugu rubripes*; dr, *Danio rerio*; nv, *Nematostella vectensis*; bf, *Branchiostoma floridae*; stp, *Strongylocentrotus purpuratus*; ci, *Ciona intestinalis*; ce, *Caenorhabditis elegans*; dm, *Drosophila melanogaster*; ta, *Trichoplax adherens*. hsTOR1A (SEQ ID NO: 11); hsTOR1B (SEQ ID NO: 12); hsTOR2A (SEQ ID NO: 13); hsTOR3A (SEQ ID NO: 14); oaTOR (SEQ ID NO: 15); ggTOR (SEQ ID NO: 16); trTOR (SEQ ID NO: 17); drTOR (SEQ ID NO: 18); nvTOR (SEQ ID NO: 19); dfTOR (SEQ ID NO: 20); stpTOR (SEQ ID NO: 21); ciTOR (SEQ ID NO: 22); ceTOR2 (SEQ ID NO: 23); ceTOR1 (SEQ ID NO: 24); ceOOC-5 (SEQ ID NO: 25); dmTOR1 (SEQ ID NO: 26); taTOR (SEQ ID NO: 27); dmTOR2 (SEQ ID NO: 28); dmTOR3 (SEQ ID NO: 29); hsTOR4A (SEQ ID NO: 30).

AAA+ ATPases are organized into a number of structurally defined clades [12, 18], distinguished by shared structural elements. Comparison with other AAA+ ATPase structures shows that TorsinA fits best into a clade that also contains the bacterial proteins Hs1U, ClpA/B, ClpX, and Lon, all of which are involved in protein degradation or remodeling [13]. These AAA+ family members share a β-hairpin insertion that precedes the sensor-I region (FIG. 12). TorsinA also contains this structural element, but it adopts a distinctly different orientation compared to other members of the clade. However, the pre-sensor I region may be affected by crystal packing in our structure. Two other distinct regions are present. The protein degrading or remodeling AAA+ ATPases all form hexameric rings with a central pore [11,13], and 'pore loops' in each subunit, conserved elements positioned between strand β2 and helix α2, are critical for threading the protein substrates through the ring [19]. In Torsins, this pore loop is not conserved (FIG. 13). TorsinA has two cysteines (Cys280, and Cys 319 in close proximity in the sensor-II motif), positioned near the adenine base of the ATP molecule (FIG. 8). These cysteines do not form a disulfide bridge in our structure. However, the conservation of Cys280 and the Gly-Cys-Lys sensor-II motif at position 318-320 (FIG. 13) indicates an important functional role. A redox activity as part of the ATPase cycle therefore seems highly likely, as has been previously speculated [8, 20].

The interaction of TorsinA with its ATPase activators LULL1 and LAP1 is of particularly importance, as a prominent mutation causing primary dystonia—the deletion of glutamate 302 or 303—weakens these interaction [7-9]. But why and how? The TorsinA-LULL1 interface extends over an area of 1527 Å$^2$. The main structural elements involved in this interaction are the nucleotide-binding region as well as the small domain of TorsinA, and helices α0, α2, α4 and α5 of LULL1 (FIGS. 6-9, 13 and 14). The exact position of the small domain of TorsinA relative to the large domain is likely dictated by the sensor II motif, preceding α8, which directly contacts the γ-phosphate of ATP through Lys 320, thus serving as an anchor point. A switch to ADP presumably weakens this connection, such that the small domain would become more loosely attached to the large domain. This could explain the observed ATP-dependency of LAP1/LULL1 binding [7-9, 21]. Within the small domain, helix α7, the following loop, and the terminal helix α8 contain all the critical residues. Glutamate 302 and 303 are positioned at the very end of helix α7, and both are involved in TorsinA contacts. Specifically, Glu 303 forms a prominent charge interaction with Arg 276 of LULL1. TorsinA Lys113-LULL1 Glu385, TorsinA Asp316-LULL1 Arg419, TorsinA Lys317-LULL1 Glu415 are additional charge interactions.

Figure 9:
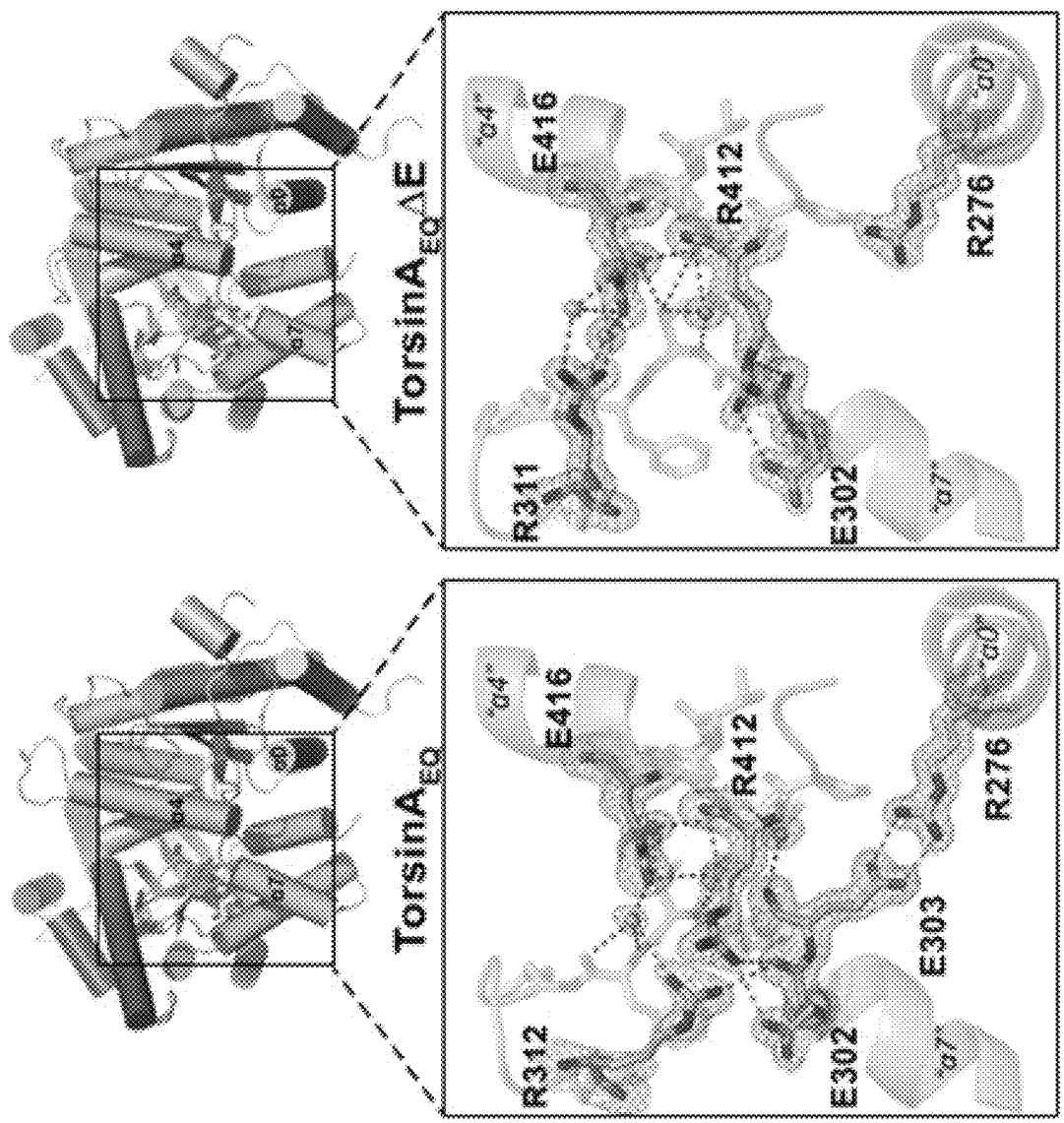
FIGS. 9, 10A and 10B are Analysis of the TorsinA-LULL1 interface.
Figure 10B:
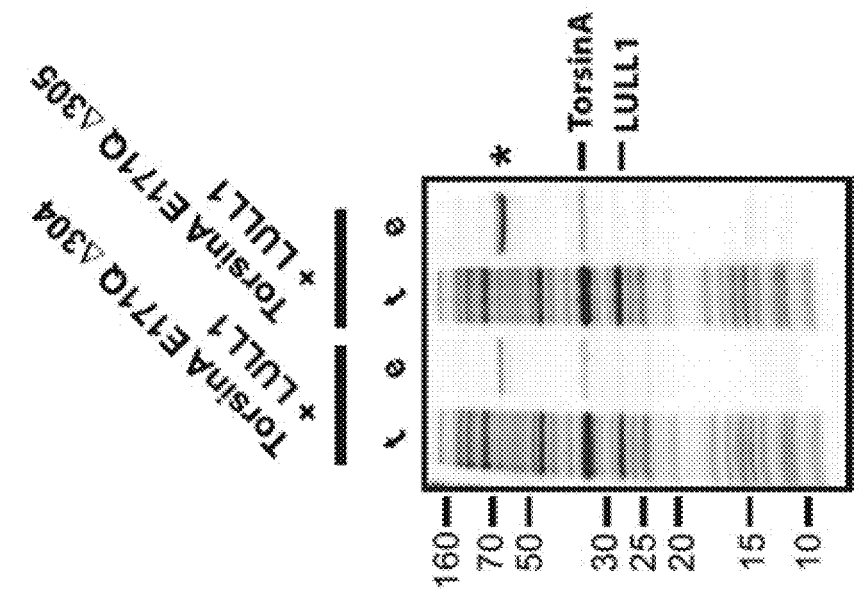
Figure 10A:
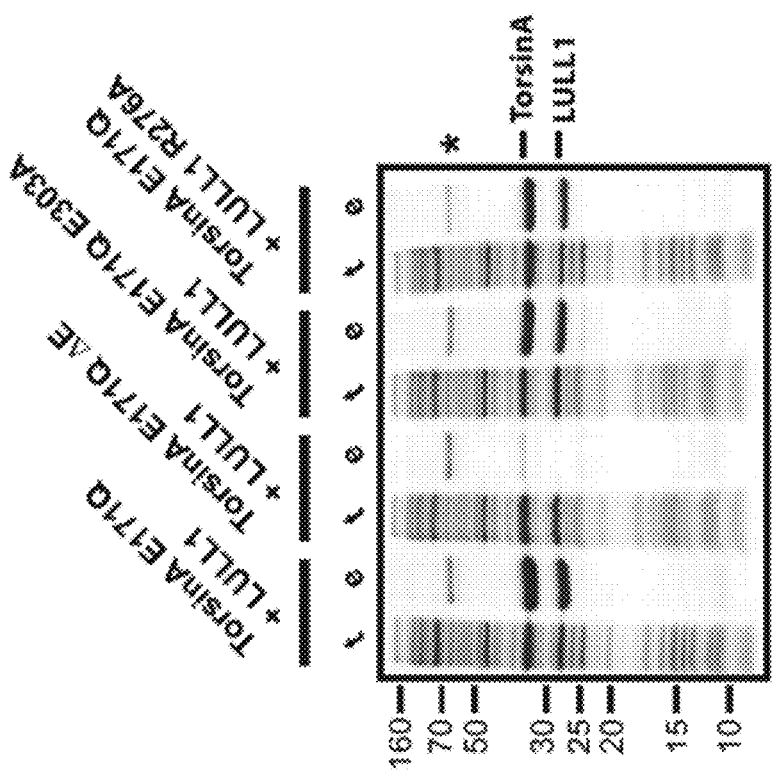

To investigate the atomic details of the weakened binding of TorsinAAE to LAP1/LULL1, and thus the molecular basis of primary dystonia, we made use of the observation that VHH-BS2 also stabilizes the TorsinA$_{EQ}$AE(ATP)-LULL1 interaction. We were able to crystallize TorsinA$_{EQ}$AE(ATP)-LULL1-VHH-BS2 and determine its structure at a resolution of 1.4 Å. Not surprisingly, the overall structure is almost identical to the wild type protein (0.34 Å rmsd over 274 Cα atoms for TorsinA, 0.26 Å rmsd over 229 Cα atoms for LULL1), except for critical differences in the TorsinA-LULL1 interface (FIG. 9). The principal difference is that helix α7 is shortened due to the missing Glu 303, with a slight—but significant—restructuring of the loop that follows to establish the connection with helix α8. For future reference, we suggest renaming the ΔE mutation ΔE303, rather than ΔE302/303, since the position of Glu 302 is effectively unchanged. In the dystonia mutant, the TorsinA Glu 303-LULL1 Arg 276 charge interaction is lost, and the hydrogen-bonding network involving TorsinA Glu 302, Phe 306 and Arg312, as well as LULL1 Arg412 and Glu416 is disrupted (FIG. 9). To determine the importance of different TorsinA residues for LULL1 binding, we performed a co-purification assay (FIGS. 10A and 10B). His-tagged, ATP-trapped TorsinAEQ (residues 51-332) and mutants thereof were recombinantly co-expressed with LULL1 (residues 233-470), but without VHH-BS2, in bacteria. Binding was tested in a co-purification assay using Ni-affinity. The Torsin$_{EQ}$ΔE303 mutation abolishes binding in this assay, as expected (FIG. 10A). Since unbound TorsinA$_{EQ}$ is largely insoluble, absence of binding is not registered as an appearance of TorsinA$_{EQ}$ alone, but rather as a lack of eluted protein complex altogether Eliminating the salt bridge between TorsinA Glu303 and LULL1 Arg276 does not disrupt the TorsinA-LULL1 interaction (FIG. 10A). However, ΔMet304 and ΔThr305 both phenocopy ΔE303 in abolishing LULL1 binding (FIG. 10B). This is in full agreement with published in vivo data using similar mutants [22]. The intricate network of interactions of the α7-α8 loop of TorsinA is crucial for LULL1 binding. Since the ΔE mutation results in a local change only of the surface of Torsin's small domain rather than protein misfolding, it may be possible to rescue binding by developing a small molecule that resurrect the weakened TorsinAΔE-LAP1/LULL1 interaction.

Figure 16:
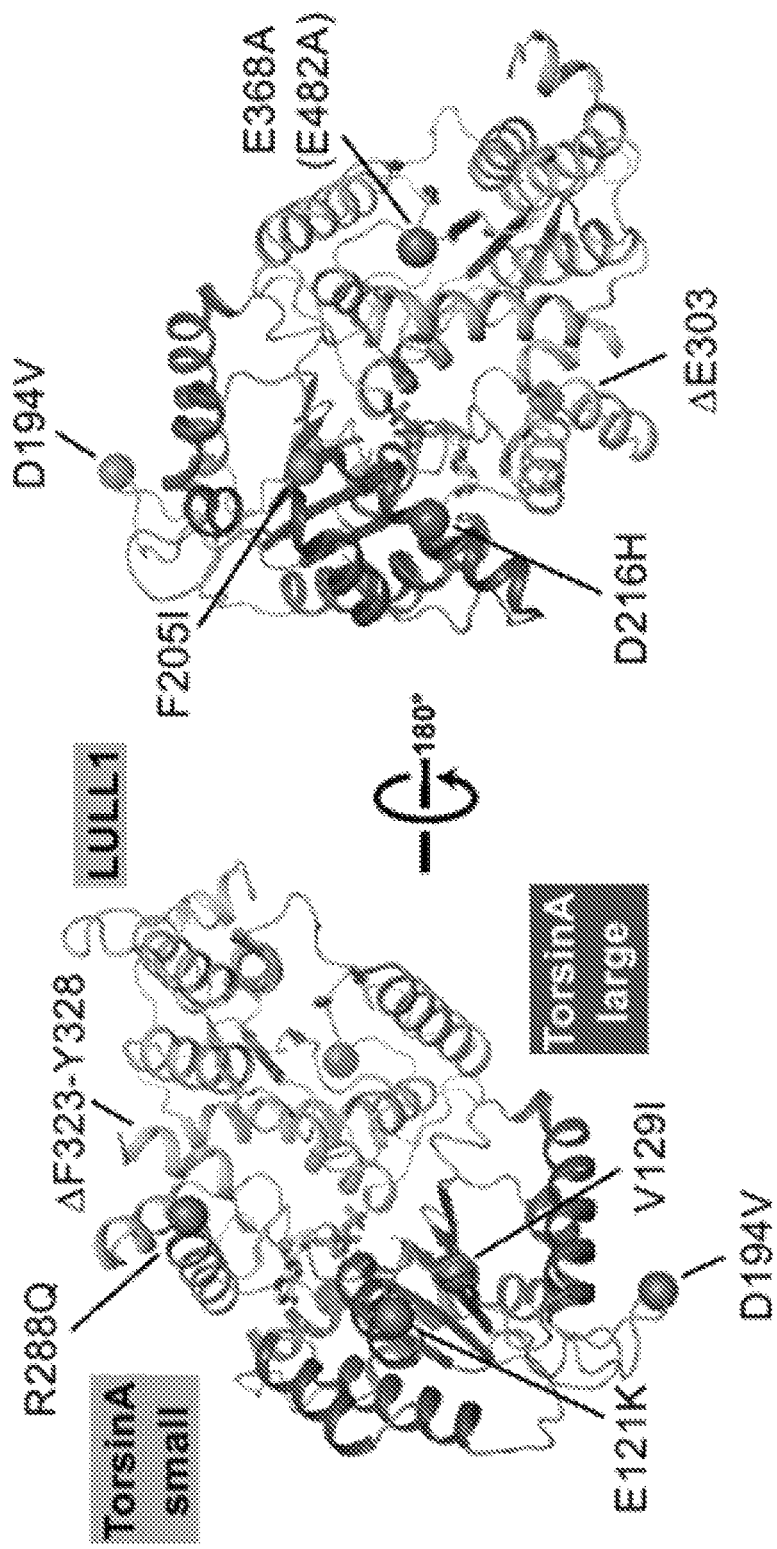
FIG. 16 shows dystonia mutations. All known point mutations and deletions that lead to dystonia are marked as green dots and shown in light green color, respectively, on the TorsinA-ATP-LULL1 structure. A modifier TorsinA mutation, D216H, is marked as a blue dot. The structural equivalent of the LAP1 missense mutation (E482A) would be the LULL1 E368A, marked as a green dot. See Table 2 in FIG. 18 for an explanation of the likely structural consequence.

Although TorsinAΔE303 is the most prevalent mutation that causes primary dystonia, it is not the only one [5, 6]. We examined the structural consequence of all known mutations (FIG. 18 Table 2, and FIG. 16). Most mutations appear to cause protein misfolding or weaken or abolish LAP1/LULL1 binding. Conversely, the two dystonia-mutations found in LAP1 likely affect Torsin interaction. Improper Torsin activation is therefore the likely cause of the disease [23].

The biological function of TorsinA remains enigmatic [24-28]. Because TorsinA belongs to the AAA+ ATPase superfamily, with specific homology to the bacterial proteins Hs1U, ClpX, ClpA/B and Lon, it is generally assumed that TorsinA is involved in protein remodeling or protein degradation [5, 6]. However, a substrate of TorsinA has yet to be identified.

Figures 11A, 11B:
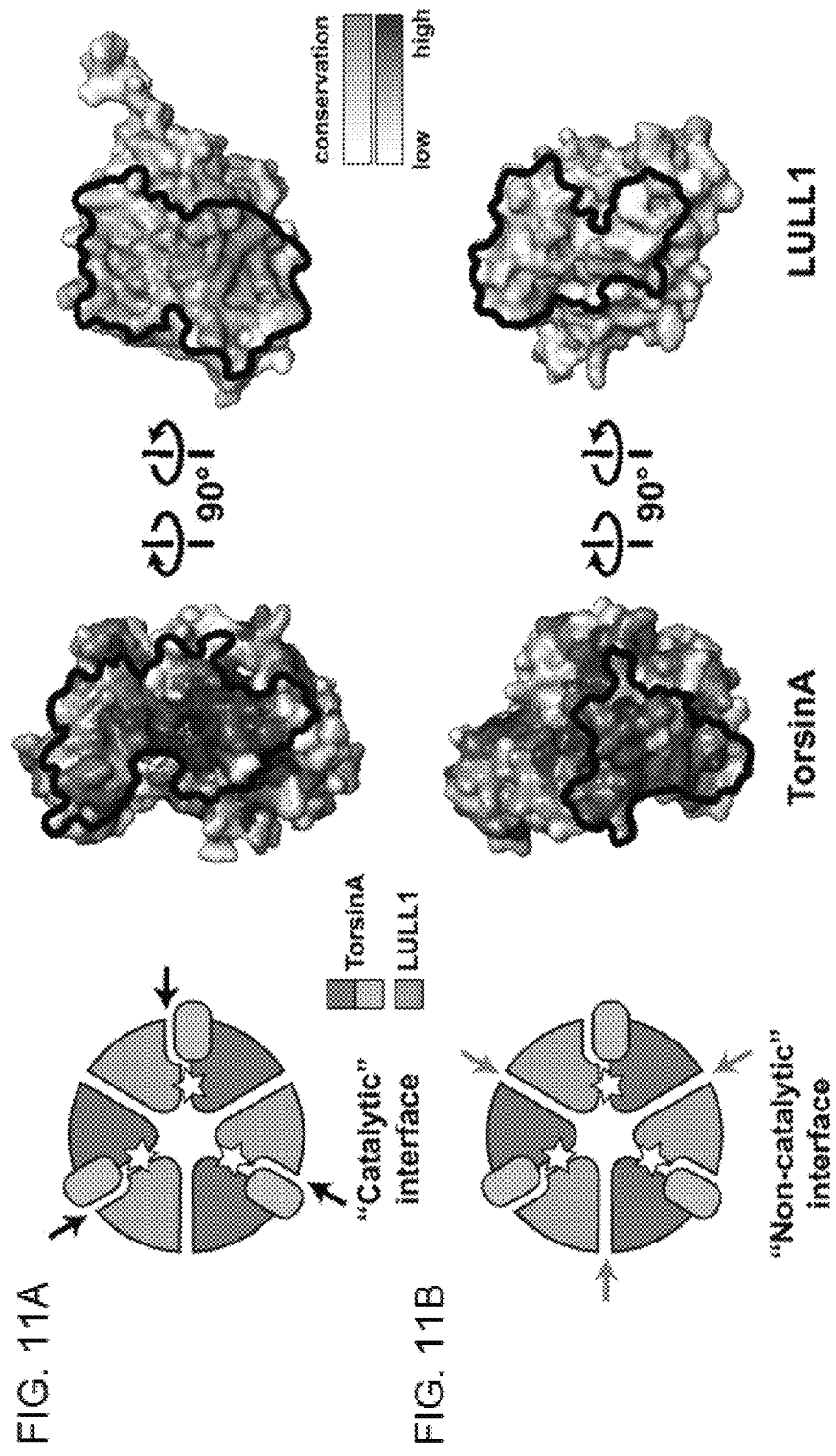
FIGS. 11A and 11B shows oligomerization of TorsinA-LULL1.
Figure 14:
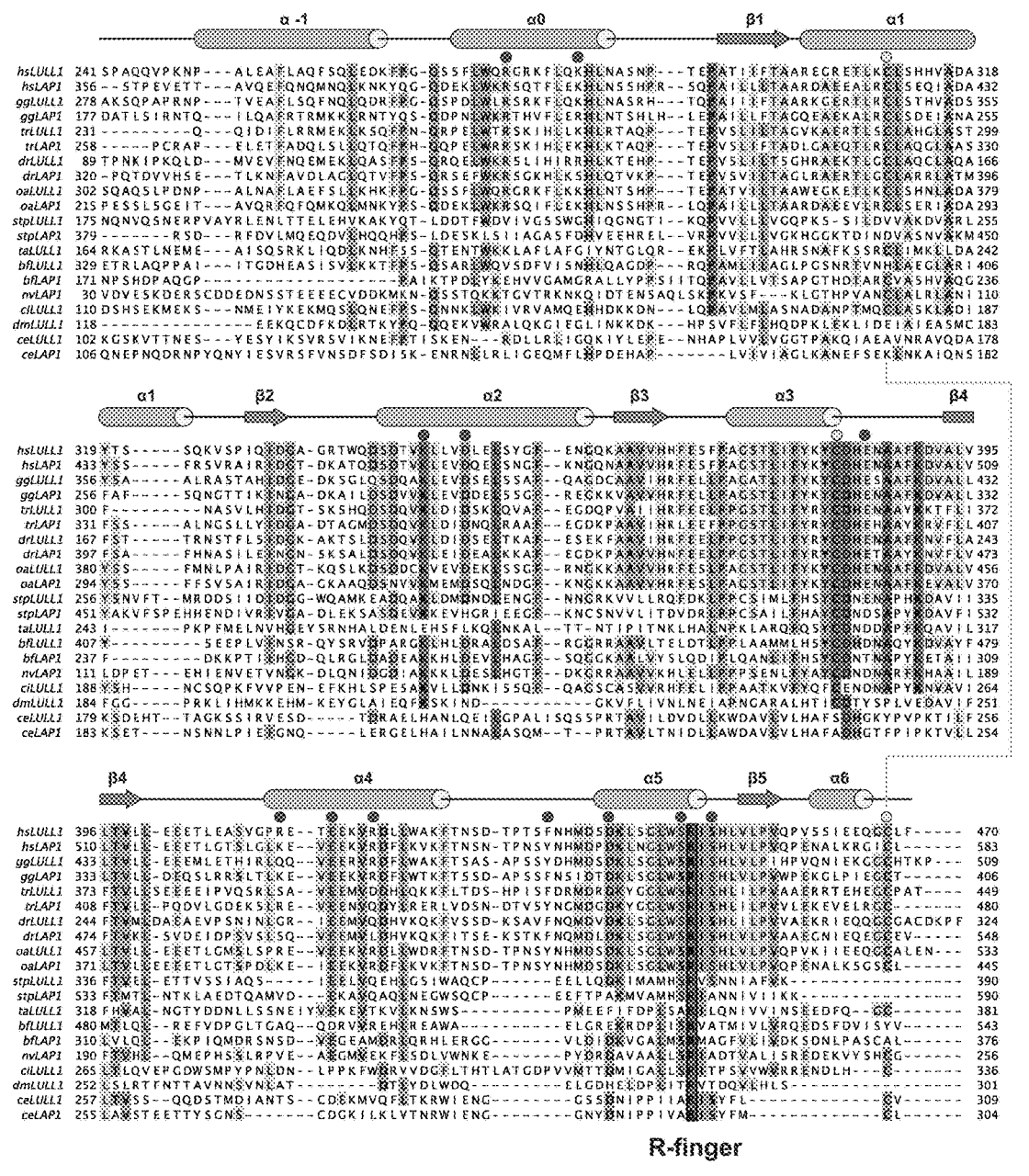

The TorsinA structure enables a more thorough comparison to other AAA+ ATPases. After the discovery that LAP1/LULL1 are Arg-finger containing TorsinA activators, it seemed reasonable to suggest that TorsinA and LAP1/LULL1 likely form heterohexameric rings ((TorsinA-ATP-LAP1/LULL1)$_3$) in order to function [14, 16]. However, the predominant oligomeric form of the TorsinA-ATP-LAP1/LULL1 complex in solution is largely heterodimeric, with the heterohexameric form present as only a small fraction [14, 16, 29-31]. Our structure now raises doubts about the physiological relevance of a heterohexameric ring (FIGS. 11A and 11B). First, we note that the small domain of TorsinA is essential for LAP1/LULL1 binding. Neither LAP1 nor LULL1 harbor a small domain, arguing against formation of a stable heteromeric ring, or, alternatively, suggesting a ring of substantially different architecture. Second, ring formation is important for AAA+ ATPases that thread their protein substrate through a central pore for refolding or for degradation. This central pore is lined with conserved 'pore loops' that are essential for function. Neither TorsinA and its homologs, nor LAP1/LULL1 have 'pore loop' equivalents (FIG. 14). TorsinA is therefore unlikely to actually employ a peptide threading mechanism that involves a central pore. Third, the surface conservation of LAP1/LULL1 also argues against a heteromeric ring assembly. Although the catalytic, ATP-containing interface with TorsinA is well-conserved, the presumptive non-catalytic, nucleotide-free interface is not (FIG. 3B). The same analysis for TorsinA shows that its 'backside' is conserved. TorsinA may therefore interact in homotypic fashion with TorsinA, with other Torsin homologs, or even with a third player. The physiologically relevant oligomeric state of TorsinA thus remains a matter of speculation. Given the unique properties of TorsinA, keeping an open-mind about TorsinA assembly into its functional state is called for, as it may well differ more than anticipated from well-studied AAA+ ATPase systems.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

REFERENCE LIST

The following references are incorporated herein by reference in their entirety for all purposes.

[1] Ozelius, L. J. et al. The early-onset torsion dystonia gene (DYT1) encodes an ATP-binding protein. Nat. Genet. 17, 40-48 (1997).
[2] Breakefield, X. O. et al. The pathophysiological basis of dystonias. Nat. Rev. Neurosci. 9, 222-234 (2008).
[3] Granata, A. & Warner, T. T. The role of torsinA in dystonia. Eur. J. Neurol. 17 Suppl 1, 81-87 (2010).
[4] McCullough, J. & Sundquist, W. I. Putting a finger in the ring. Nat. Struct. Mol. Biol. 21, 1025-1027 (2014).
[5] Rose, A. E., Brown, R. S. H. & Schlieker, C. Torsins: not your typical AAA+ ATPases. Crit. Rev. Biochem. Mol. Biol. 50, 532-549 (2015).
[6] Laudermilch, E. & Schlieker, C. TorsinATPases: structural insights and functional perspectives. Curr. Opin. Cell Biol. 40, 1-7 (2016).
[7] Naismith, T. V., Dalal, S. & Hanson, P. I. Interaction of torsinA with its major binding partners is impaired by the dystonia-associated DeltaGAG deletion. J. Biol. Chem. 284, 27866-27874 (2009).
[8] Zhu, L., Millen, L., Mendoza, J. L. & Thomas, P. J. A unique redox-sensing sensor II motif in TorsinA plays a critical role in nucleotide and partner binding. J. Biol. Chem. 285, 37271-37280 (2010).
[9] Zhao, C., Brown, R. S. H., Chase, A. R., Eisele, M. R. & Schlieker, C. Regulation of TorsinATPases by LAP1 and LULL1. Proc. Natl. Acad. Sci. U.S.A. 110, E1545-54 (2013).
[10] Goodchild, R. E., Kim, C. E. & Dauer, W. T. Loss of the dystonia-associated protein torsinA selectively disrupts the neuronal nuclear envelope. Neuron 48, 923-932 (2005).
[11] Hanson, P. I. & Whiteheart, S. W. AAA+ proteins: have engine, will work. Nat. Rev. Mol. Cell Biol. 6, 519-529 (2005).
[12] Erzberger, J. P. & Berger, J. M. Evolutionary relationships and structural mechanisms of AAA+ proteins. Annu Rev Biophys Biomol Struct 35, 93-114 (2006).
[13] Olivares, A. O., Baker, T. A. & Sauer, R. T. Mechanistic insights into bacterial AAA+ proteases and protein-remodelling machines. Nat. Rev. Microbiol. 14, 33-44 (2016).
[14] Sosa, B. A. et al. How lamina-associated polypeptide 1 (LAP1) activates Torsin. Elife 3, e03239 (2014).
[15] Wendler, P., Ciniawsky, S., Kock, M. & Kube, S. Structure and function of the AAA+ nucleotide binding pocket. Biochim. Biophys. Acta 1823, 2-14 (2012).
[16] Brown, R. S. H., Zhao, C., Chase, A. R., Wang, J. & Schlieker, C. The mechanism of TorsinATPase activation. Proc. Natl. Acad. Sci. U.S.A. 111, E4822-31 (2014).
[17] Muyldermans, S. Nanobodies: natural single-domain antibodies. Annu. Rev. Biochem. 82, 775-797 (2013).
[18] Iyer, L. M., Leipe, D. D., Koonin, E. V. & Aravind, L. Evolutionary history and higher order classification of AAA+ ATPases. J. Struct. Biol. 146, 11-31 (2004).
[19] Sauer, R. T. & Baker, T. A. AAA+ proteases: ATP-fueled machines of protein destruction. Annu. Rev. Biochem. 80, 587-612 (2011).
[20] Zhu, L., Wrabl, J. O., Hayashi, A. P., Rose, L. S. & Thomas, P. J. The torsin-family AAA+ protein OOC-5 contains a critical disulfide adjacent to Sensor-II that couples redox state to nucleotide binding. Mol. Biol. Cell 19, 3599-3612 (2008).
[21] Goodchild, R. E. & Dauer, W. T. The AAA+ protein torsinA interacts with a conserved domain present in LAP1 and a novel ER protein. J. Cell Biol. 168, 855-862 (2005).
[22] Goodchild, R. E. & Dauer, W. T. Mislocalization to the nuclear envelope: an effect of the dystonia-causing torsinA mutation. Proc. Natl. Acad. Sci. U.S.A. 101, 847-852 (2004).
[23] Kim, C. E., Perez, A., Perkins, G., Ellisman, M. H. & Dauer, W. T. A molecular mechanism underlying the neural-specific defect in torsinA mutant mice. Proc. Natl. Acad. Sci. U.S.A. 107, 9861-9866 (2010).
[24] Nery, F. C. et al. TorsinA binds the KASH domain of nesprins and participates in linkage between nuclear envelope and cytoskeleton. J. Cell. Sci. 121, 3476-3486 (2008).
[25] Granata, A., Koo, S. J., Haucke, V., Schiavo, G. & Warner, T. T. CSN complex controls the stability of selected synaptic proteins via a torsinA-dependent process. EMBO J. 30, 181-193 (2011).
[26] Nery, F. C. et al. TorsinA participates in endoplasmic reticulum-associated degradation. Nat Commun 2, 393 (2011).
[27] Jokhi, V. et al. Torsin mediates primary envelopment of large ribonucleoprotein granules at the nuclear envelope. Cell Rep 3, 988-995 (2013).
[28] Liang, C.-C., Tanabe, L. M., Jou, S., Chi, F. & Dauer, W. T. TorsinA hypofunction causes abnormal twisting movements and sensorimotor circuit neurodegeneration. J. Clin. Invest. 124, 3080-3092 (2014).
[29] Jungwirth, M., Dear, M. L., Brown, P., Holbrook, K. & Goodchild, R. Relative tissue expression of homologous torsinB correlates with the neuronal specific importance of DYT1 dystonia-associated torsinA. Hum. Mol. Genet. 19, 888-900 (2010).
[30] Vander Heyden, A. B., Naismith, T. V., Snapp, E. L., Hodzic, D. & Hanson, P. I. LULL1 retargets TorsinA to the nuclear envelope revealing an activity that is impaired by the DYT1 dystonia mutation. Mol. Biol. Cell 20, 2661-2672 (2009).
[31] Goodchild, R. E. et al. Access of torsinA to the inner nuclear membrane is activity dependent and regulated in the endoplasmic reticulum. J. Cell. Sci. 128, 2854-2865 (2015).
[32] Andersen, K. R., Leksa, N. C. & Schwartz, T. U. Optimized *E. coli* expression strain LOBSTR eliminates common contaminants from His-tag purification. Proteins 81, 1857-1861 (2013).
[33] Otwinowski, Z. & Minor, W. [20] Processing of X-ray diffraction data collected in oscillation mode. Methods in Enzymology 276, 307-326 (Elsevier, 1997).
[34] Morin, A. et al. Collaboration gets the most out of software. Elife 2, e01456 (2013).
[35] Adams, P. D. et al. PHENIX: a comprehensive Python-based system for macromolecular structure solution. Acta Crystallogr. D Biol. Crystallogr. 66, 213-221 (2010).

[36] Söding, J., Biegert, A. & Lupas, A. N. The HHpred interactive server for protein homology detection and structure prediction. Nucleic Acids Res. 33, W244-8 (2005).

[37] Chen, V. B. et al. MolProbity: all-atom structure validation for macromolecular crystallography. Acta Crystallogr. D Biol. Crystallogr. 66, 12-21 (2010).

[38] Emsley, P., Lohkamp, B., Scott, W. G. & Cowtan, K. Features and development of Coot. Acta Crystallogr. D Biol. Crystallogr. 66, 486-501 (2010).

[39] Altschul, S. F. et al. Gapped BLAST and PSI-BLAST: a new generation of protein database search programs. Nucleic Acids Res. 25, 3389-3402 (1997).

[40] Kelley, L. A. & Sternberg, M. J. E. Protein structure prediction on the Web: a case study using the Phyre server. Nat Protoc 4, 363-371 (2009).

[41] Tusnády, G. E. & Simon, I. The HMMTOP transmembrane topology prediction server. Bioinformatics 17, 849-850 (2001).

[42] Edgar, R. C. MUSCLE: a multiple sequence alignment method with reduced time and space complexity. BMC Bioinformatics 5, 113 (2004).

[43] Waterhouse, A. M., Procter, J. B., Martin, D. M. A., Clamp, M. & Barton, G. J. Jalview Version 2—a multiple sequence alignment editor and analysis workbench. Bioinformatics 25, 1189-1191 (2009).

[44] Glaser, F. et al. ConSurf: identification of functional regions in proteins by surface-mapping of phylogenetic information. Bioinformatics 19, 163-164 (2003).

[45] Crooks, G. E., Hon, G., Chandonia, J.-M. & Brenner, S. E. WebLogo: a sequence logo generator. Genome Res. 14, 1188-1190 (2004).

[46] Zeymer, C., Barends, T. R. M., Werbeck, N. D., Schlichting, I. & Reinstein, J. Elements in nucleotide sensing and hydrolysis of the AAA+ disaggregation machine ClpB: a structure-based mechanistic dissection of a molecular motor. Acta Crystallogr. D Biol. Crystallogr. 70, 582-595 (2014).

[47] Leung, J. C. et al. Novel mutation in the TOR1A (DYT1) gene in atypical early onset dystonia and polymorphisms in dystonia and early onset parkinsonism. Neurogenetics 3, 133-143 (2001).

[48] Zirn, B. et al. Novel TOR1A mutation p.Arg288Gln in early-onset dystonia (DYT1). J. Neurol. Neurosurg. Psychiatr. 79, 1327-1330 (2008).

[49] Calakos, N. et al. Functional evidence implicating a novel TOR1A mutation in idiopathic, late-onset focal dystonia. J. Med. Genet. 47, 646-650 (2010).

[50] Cheng, F.-B. et al. Combined occurrence of a novel TOR1A and a THAP1 mutation in primary dystonia. Mov. Disord. 29, 1079-1083 (2014).

[51] Vulinovic, F. et al. Unraveling cellular phenotypes of novel TorsinA/TOR1A mutations. Hum. Mutat. 35, 1114-1122 (2014).

[52] Dobričić, V. et al. Phenotype of non-c.907_909delGAG mutations in TOR1A: DYT1 dystonia revisited. Parkinsonism Relat. Disord. 21, 1256-1259 (2015).

[53] Kock, N. et al. Effects of genetic variations in the dystonia protein torsinA: identification of polymorphism at residue 216 as protein modifier. Hum. Mol. Genet. 15, 1355-1364 (2006).

[54] Kamm, C. et al. Susceptibility to DYT1 dystonia in European patients is modified by the D216H polymorphism. Neurology 70, 2261-2262 (2008).

[55] Kayman-Kurekci, G. et al. Mutation in TOR1AIP1 encoding LAP1B in a form of muscular dystrophy: a novel gene related to nuclear envelopathies. Neuromuscul. Disord. 24, 624-633 (2014).

[56] Dorboz, I. et al. Severe dystonia, cerebellar atrophy, and cardiomyopathy likely caused by a missense mutation in TOR1AIP1. Orphanet J Rare Dis 9, 174 (2014).

What is claimed is:

1. A protein composition, comprising: a target protein; a modulator of the target protein; and a nanobody comprising a polypeptide as set forth in SEQ ID NO: 5 or a portion thereof, wherein said nanobody or said portion thereof specifically binds to at least one of the target protein and the modulator.

2. The protein composition of claim 1, wherein the target protein is TorsinA, a mutant of TorsinA, or a portion thereof.

3. The protein composition of claim 2, wherein the target protein comprises an amino acid sequence as set forth in at least one of SEQ ID NO: 1-3 or a portion thereof.

4. The protein composition of claim 1, wherein the modulator is LULL1 or a portion thereof.

5. The protein composition of claim 4, wherein the modulator comprises the amino acid sequence set forth in the SEQ ID NO: 4.

6. The protein composition of claim 1, wherein the nanobody is specific for a complex comprising the target protein and the modulator.

7. The protein composition of claim 6, wherein the nanobody is obtained by immunization using the target protein comprising the amino acid sequence set forth in the SEQ ID NO: 2 and the modulator comprising the amino acid sequence set forth in the SEQ ID NO: 4.

8. The protein composition of claim 7, wherein the target protein comprises the amino acid sequence set forth in at least one of SEQ ID NO: 1-3 or a portion thereof, the modulator comprises the amino acid sequence set forth in the SEQ ID NO: 4 or a portion thereof, the nanobody comprises the amino acid sequence set forth in the SEQ ID NO: 5 or a portion thereof, and the protein composition is co-expressed, and optionally purified together.

* * * * *